(12) United States Patent
Sherr et al.

(10) Patent No.: US 6,586,203 B1
(45) Date of Patent: *Jul. 1, 2003

(54) ARF-P19, A NOVEL REGULATOR OF THE MAMMALIAN CELL CYCLE

(75) Inventors: Charles J. Sherr, Memphis, TN (US); Dawn Quelle, Coralville, IA (US); Martine F. Roussel; Frederique Zindy, both of Memphis, TN (US)

(73) Assignee: St. Jude Children's Research Hospital, Memphis, TN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/129,855

(22) Filed: Aug. 6, 1998

Related U.S. Application Data

(60) Continuation-in-part of application No. 08/954,470, filed on Oct. 20, 1997, now Pat. No. 5,876,965, which is a division of application No. 08/534,975, filed on Sep. 27, 1995, now Pat. No. 5,723,313.

(51) Int. Cl.[7] ............... C12P 21/06; C07K 14/00; C07H 17/00
(52) U.S. Cl. ............... 435/69.1; 514/12; 514/2; 514/44; 530/350
(58) Field of Search ............... 514/12, 2, 44; 530/350; 435/69.1

(56) References Cited

U.S. PATENT DOCUMENTS

| | | | |
|---|---|---|---|
| 4,965,188 A | 10/1990 | Mullis et al. | |
| 5,174,986 A | 12/1992 | Berns | |
| 5,185,260 A | 2/1993 | Crissman et al. | |
| 5,723,313 A | * 3/1998 | Sherr et al. | 435/69.1 |
| 5,739,027 A | 4/1998 | Kamb | |
| 5,876,965 A | * 3/1999 | Sherr et al. | 435/69.1 |

FOREIGN PATENT DOCUMENTS

| | | |
|---|---|---|
| WO | WO 92/20796 | 11/1992 |
| WO | WO 95/25429 | 9/1995 |
| WO | WO 95/28483 | 10/1995 |
| WO | WO97/12060 | 4/1997 |

OTHER PUBLICATIONS

Alcorta et al., Proc. Natl. Acad. Sci. USA, 93: 13742–13747 (1996).*
Baldin, V. et al., "Cyclin D1 is a nuclear protein required for cell cycle progression in $G_1$," Genes & Dev. 7: 812–821 (May 1993).*
Bates, S. et al., "Absense of cyclin D/cdk complexes in cell lacking functional retinoblastoma protein," Oncogene 9(6): 1633–1640 (Jun. 1994).*
Caldas et al., Nature Genet 8:27–32 (1994).*
Calnan, B.J. et al., Science 252: 1167–1171 (1991), and Erratum, 255:665 (1992).*
Chan et al., Mol. Cell. Biol. 15: 2682–2688 (1995).*
Cheng et al., Proc. Natl. Acad. Sci. USA 95; 1091–1096 (1998).*
Chen et al. Mol. Cell. Biol., 13: 4107–4114 (1993).*
Craven, M.G. et al., J. Bacteriol. 176: 1394–1404 (1994).*
Debbas and Whie, Genes Dev. 7; 546–554 (1993).*
Degregori et al., Proc. Natl. Acad. Sci. USA 94; 7245–7250 (1997).*
Donehower et al., Nature, 356: 215–221 (1992).*
Dowdy, S.F. et al., "Physical Interaction of the Retinoblastoma Protein with Human D Cyclins," Cell 73(3): 499–511 (May 1993).*
Duro, D. et al., "A new type of $p16^{ink4}$/MTS1 gene transcript expressed in B–cell malignancies," Oncogene 11: 21–29 (Jul. 1995).*
El–Deiry, W.S. et al., "WAF1, a Potential Mediator of p53 Tumor Suppression," Cell 75(4): 817–825 (Nov. 1993).*
Evan et al., Cell 69: 119–128 (1992).*
Ewen, M.E. et al., "Functional Interactions of the Retinoblastoma protein with Mammalian D–type Cyclins," Cell 73(3): 487–497 (May 1993).*
Fitzgerald et al., Proc. Natl. Acad. Sci. USA 93: 8541–8545 (1996).*
Friedlander et al., J. Biol. Chem. 271: 25468–25478 (1996).*
Fukusawa et al., Science, 271: 1744–1747 (1996).*
Gannon and Lane, Nature 349: 802–806 (1991).*
Gannon et al., EMBO J. 9: 1595–1602 (1990).*
Gottlieb and Oren, Biochem. Biophys. Acta, 1287: 77–102 (1996).*
Gu, Y. et al., "Inhibition of CDK2 activity in vivo by an associated 20K regulatory subunit," Nature 366: 707–710 (Dec. 1993).*
Guan, K.–L. Et al., "Growth suppression by p18, a $p16^{INK4/MTS1}$– and $p14^{INK4B/MTS2}$–related CDK6 inhibitor, correlates with wild–type pRb function," Genes & Dev. 8(24); 2932–2952 (Dec. 1994).*
Gutierres et al., Proc. Natl. Acad. Sci. USA 94: 3436–3440 (1997).*
Hainaut et al., Nucleic Acid Res., 25: 151–157 (1997).*
Hall and Peters, Adv. Cancer Res., 68: 67–108 (1996).*

(List continued on next page.)

Primary Examiner—Karen Cochrane Carlson
(74) Attorney, Agent, or Firm—Alston & Bird LLP

(57) ABSTRACT

The INK4A (MTS1, CDKN2) gene encodes a specific inhibitor (InK4a-p16) of the cyclin D-dependent kinases CDK4 and CDK6. InK4a-p16 can block these kinase from phosphorylating the retinoblastoma protein (pRb), preventing exit from the G1 phase of the cell cycle. Deletions and mutations involving the gene encoding InK4a-p16, INK4A, occur frequently in cancer cells, implying that INK4a-p16, like pRb, suppresses tumor formulation. However, a completely unrelated protein (ARF-p19) arises in major part from an alternative reading frame of the mouse INK4A gene. Expression of an ARF-p19 cDNA (SEQ ID NO:1) in rodent fibroblasts induces both G1 and G2 phase arrest. Economical reutilization of protein coding sequences in this manner is without precedent in mammalian genomes, and the unitary inheritance of INK4a-p16 and ARF-p19 may reflect a dual requirement for both proteins in cell cycle control.

18 Claims, 28 Drawing Sheets

OTHER PUBLICATIONS

Figure 2A:
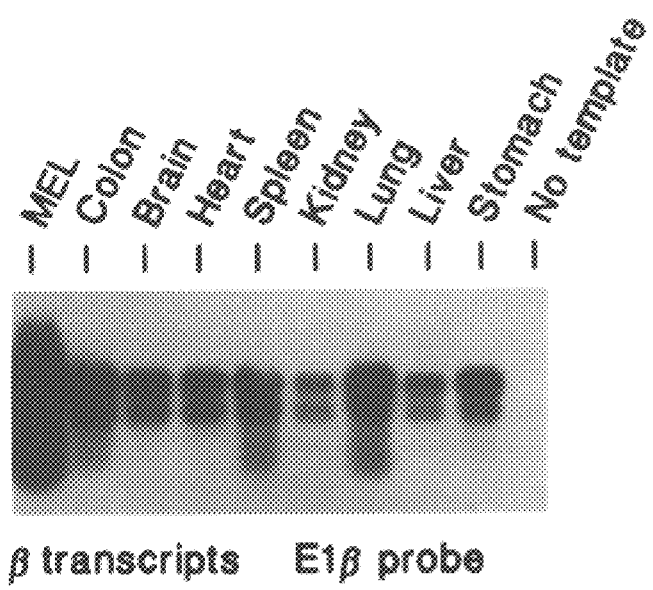

Hara et al., Mol. Cell. Biol., 16: 859–867 (1996).*
Hayashi et al., Biochem. Biophys. Res Commun. 202: 1426–1430 (1994).*
Hannon, G.J. and Beach, D., "p15$^{INK4B}$ is a potential effector of TGF–β–induced cell cycle arrest," Nature 371: 257–261 (Sep. 1994).*
Harper, J.W. et al., "The p21 Cdk–Interacting protein Cip1 Is a Potent Inhibitor of G1 Cyclin–Dependent Kinases," Cell 75(4): 805–816 (Nov. 1993).*
Harvey et al., Oncogene, 8: 2457–2467 (1993).*
Harvey and Levine, Genes Dev. 5: 2375–2385 (1991).*
Haupt et al., Nature 387: 296–299 (1997).*
Hermeking and Eick, Science 265; 2091–2093 (1994).*
Herzog wt al., Oncogene, 13: 1885–1891 (1996).*
Hirai, H. et al., "Novel INK4 Proteins, p19 and p18, Are Specific Inhibitors of the Cyclin D–Dependent Kinases CDK4 and CDK6," Mol. Cell. Biol. 15(5): 2672–2681 (May 1995).*
Hirama and Koeffler, Blood 86: 841–854 (1995).*
Honda et al., FEBS Lets. 420: 25–27 (1997).*
Hunter and Pines, Cell 79: 573–582 (1994).*
Hussussian et al., Nature Genet 8: 15–21 (1994).*
Jacks et al., Curr. Biol. 4: 1–7 (1994).*
Jones et al., Nature 387: 299–303 (1997).*
Kamb, A. et al., Nature Genet 8: 22–26 (1994b).*
Kamb, A. et al., "A Cell Cycle Regulator Potentially Involved in Genesis of Many Tumor Types," Science 264: 436–440 (Apr. 1994).*
Kamijo, T. et al., "Tumor Suppression at the Mouse INK4a Locus Mediated by the Alternative Reading Frame product p19ARF," Cell 91(11): 641–659 (Nov. 1997).*
Kato, J.–Y. Et al., "Direct binding of cyclin D to the retinoblastoma gene product (pRb) and pRb phosphorylation by the cyclin D–dependent kinase CDK4," Genes & Dev. 7(3): 331–342 (Mar. 1993).*
Kemp et al., Nat. Genetics 8; 66–69 (1994).*
Ko and Prives, Genes Dev., 10:1054–1072 (1996).*
Koh et al., Nature 375: 506–510 (1995).*
Kowalik et al., J. Virol. 69: 2491–2500 (1995).*
Kubbutat et al., Nature 387: 299–303 (1997).*
Kubo et al., Biochem. Biophys. Res. Commun. 232: 38–41 (1997).*
Lazinski, D., Cell 59: 207–218 (1989).*
Lin et al., Genes Dev., 8; 1235–1246 (1994).*
Lloyd et al., Genes Dev., 11: 663–667 (1997).*
Lowe and Ruley, Genes Dev. 7; 535–545 (1993).*
Lukas, J. et al., Nature 375: 503–506 (1995).*
Lukas, J. et al., "DNA Tumor Virus Oncoproteins and Retinoblastoma Gene Mutations Share the Ability to Relieve the Cell's Requirement for Cyclin D1 Function in G1," J. Cell Biol. 125(3): 625–638 (May 1994).*
Mao, L. et al., "A Novel p16$^{INK4A}$ Transcript," Cancer Res. 55; 2995–2997 (Jul. 1995).*
Matsushime, H. et al., "Colony–Stimulating Factor 1 Regulates Novel Cyclins during the G1 Phase of the Cell Cycle," Cell 65(4): 701–713 (May 1991).*
Matsushime, H. et al., "Identification and properties of an Atypical Catalytic Subunit (p34$^{PSK\_J3}$/cdk4) for Mammalian D Type G1 Cyclins," Cell 71(2): 323–334 (Oct. 1992).*
Matsushime, H. et al., "D–Type Cyclin–Dependent Kinase Activity in Mammalian Cells," Mol. Cell. Biol. 14(3): 2066–2076 (Mar. 1994).*
Medema et al., Proc. Natl. Acad. Aci. USA 92: 6289–6293 (1995).*
Merlo et al., Nature Med. 1; 686–692 (1995).*

Meyerson, M. and Harlow, E., "Identification of $G_1$ Kinase Activity for cdk6, a Novel Cyclin D Partner," Mol. Cell. Biol. 14(3): 2077–2086 (Mar. 1994).*
Momand et al, Cell 69: 1237–1245 (1992).*
Montes de Oca Luna et al., Nature 378: 203–206 (1995).*
Morgenbesser et al., Nature 371; 72–74 (1994).*
Mori et al., cancer Res. 4: 3396–3397 (1994).*
Nasmyth, K. and Hunt, T., "Dams and sluices," Nature 366: 634–635 (Dec. 1993).*
Noble et al., Oncogene, 13; 1259–1268 (1996).*
Nobori, T. et al., "Deletions of the cyclin–dependent kinase–4 inhibitor gene in multiple human cancers," nature 368: 753–756 (Apr. 1994).*
Ohta et al., Cancer Res 54: 5269–5272 (1994).*
Okamoto, A. et al., "Mutations and altered expression of p16$^{INK4}$ in human cancer," Proc. Natl.. Acad. Sci. USA 91: 11045–11049 (Nov. 1994).*
Okuda, T., et al., Genomics, 29: 623–630 (1995).*
Okuda, T., et al., Blood 85: 2321–2330 (1995).*
Oliner et al., Nature 362: 857–860 (1993).*
Otterson et al., Oncogene 9: 3375–3378 (1994).*
Parry and Peters, Mol. Cell. Biol. 16: 3844–3852 (1996).*
Peters, G., "Stifled by inhibitions," Nature 371; 204–205 (Sep. 1994).*
Polyak, K. et al., "p27$^{Kip1}$, a cyclin–Cdk inhibitor, links transforming growth factor–β and contact inhibition to cell cycle arrest," Genes & Dev. 8(1): 9–22 (Jan. 1994).*
Polyak, K. et al., "Cloning of p27$^{Kip1}$, a Cyclin–Dependent Kinase Inhibitor and a Potential Mediator of Extracellular Antimitogenic signals," Cell 78(1); 59–66 (Jul. 1994).*
Pollock et al., Genes Chrom. Cancer, 15: 77–88 (1996).*
Pomerantz et al., Cell 92: 713–723 (1998).*
Qin et al., Proc. Natl. Acad. Sci. USA, 91: 18918–19022 (1994).*
Quelle, D.E. et al., "Overexpression of mouse D–type cyclins accelerates $G^1$ phase in rodent fibroblasts," Genes & Dev. 7(8); 1559–1571 (Aug. 1993).*
Quelle, D.E. et al., "Cloning and characterization of murine p16$^{INK4a}$ and p15$^{INK4b}$ genes," Oncogene 11: 635–645 (Aug. 1995).*
Quelle, D.E. et al., "Alternative Reading Frames of the INK4a Tumor Suppressor Gene Encode Two Unrelated Proteins Capable of Inducing Cell Cycle Arrest," Cell 83: 993–1000 (Dec. 1995).*
Quelle, D.E. et al., "Cancer–associated mutations at the INK4a locus cancel cell cycle arrest by p16$^{INK4a}$ but not by the alternative reading frame protein p19$^{ARF}$," Proc. Natl. Acad. Sci. USA 94: 669–673 (Jan. 1997).*
Reznikoff, et al., Cancer Res. 56: 2886–2890 (1996).*
Rittling and Denhardt, Oncogene 7: 935–942 (1992).*
Raymond and Brent, Oncogene 11: 1173–1178 (1995).*
Ranade et al., Nature Genetics 10: 114–116 (1995).*
Rogen et al., Mol. Cell. Biol. 15: 4745–4753 (1995).*
Roth et al., EMBO J. 17: 554–564 (1998).*
Serrano, M. et al., Cell 88: 593–602 (1997).*
Serrano, M. et al., Cell 85: 27–37 (1996).*
Serrano, M. et al., "A new regulatory motif in cell–cycle control causing specific inhibition of cyclin D/CDK4," Nature 366: 704–707 (Dec. 1993).*
Shan and Lee, Mol. Cell Biol. 14; 8166–8173 (1994).*
Shapiro et al., Cancer Res. 55: 6200–6209 (1995).*

Shaulsky et al., Oncogene 6: 2055–2065 (1991).*
Sheaff and Roberts, Curr. Biol. 5: 28–31 (1994).*
Sherr, C.J., science 274: 1672–1677 (1996).*
Sherr, C.J. et al., Genes Devel. 9: 1149–1163 (1995).*
Sherr, C.J., "Mammalian $G_1$ Cyclins," Cell 73: 1059–1065 (Jun. 1993).*
Shieh et al., Cell 91: 325–334 (1997).*
Siliciano et al. Genes Dev. 11: 3471–3481 (1997).*
Stone, S. et al., "Complex Structure and Regulation of the P16 (MTS1) Locus," Cancer Res. 55 2988–2994 (Jul. 1995).*
Swafford et al., Mol. Cell. Biol., 17: 1366–1374 (1997).*
Tam, S.W. et al., "Differential expression and regulation of Cyclin D1 protein in normal and tumor human cells: association with Cdk4 is required for Cyclin D1 function in G1 progression," Oncogene 9(9); 2663–2674 (Sep. 1994).*
Tanaka et al., Ing. J. Cancer 70: 473–442 (1997).*
Tao, J. et al., Proc. Natl. Acad. Sci. (USA) 89: 2723–2726 (1992).*
Todaro and Green, J. Cell Biol. 17: 299–313 (1963).*
Toyoshima, H. and Hunter, T., "p27, a Novel Inhibitor of G1 Cyclin–Cdk protein Kinase Activity, Is Related to p21," Cell 78(1): 67–74 (Jul. 1994).*
Wagner et al., Genes Dev. 8: 2817–2830 (1994).*
Weinberg, Cell, 88: 573–575 (1997).*
Weinberg, Cell 81: 323–330 (1995).*
Wick et al., Oncogene, 11: 2013–2019 (1995).*
Wu et al., Genes Dev., 7: 1126–1132 (1993).*
Wu and Levine, Proc. Natl. Acad. Sci. USA 91; 3602–3606 (1994).*
Xiong, Y. et al., "Subunit rearrangement of the cyclin–dependent kinases is associated with cellular transformation," Genes & Dev. 798); 1572–1583 (Aug. 1993).*
Xiong, Y. et al., "p21 is a universal inhibitor of cycling kinases," Nature 366: 701–704 (Dec. 1993).*
Yang et al., Cancer Res., 55: 2503–2506 (1995).*
Yewdell et al., J. Virol., 59: 444–452 (1986).*
Zhang et al., Cell 92: 725–734 (1998).*
Zhang et al., Cancer Res 54: 5050–5053 (1994).*
Zindy et al., Ibcifebem 15: 203–211 (1997).*
Kamijo et al., 1998, PNAS USA, 95:8292–7.
De Stanchina et al., 1998, Genes & Deve. 12:2434–42.
Chin et al., 1998, Tibs 23(8):291–6.
Sharpless et al., 1999, Curr. Opin. Genet. Dev. 9:22–30.

* cited by examiner

SEQ. ID NO:1:

```
EXON 1b                              27                                              54
GTC ACA GTG AGG CCG CCG CTG AGG GAG TAC AGC AGC GGG AGC ATG GGT CGC AGG
                                            SEQ ID NO:2:  M   G   R   R
5'PRIMER FOR RT-PCR                  81                                             108
TTC TTG GTC ACT GTG AGG ATT CAG CGC GCG GGC CGC CCA CTC CAA GAG AGG GTT
 F   L   V   T   V   R   I   Q   R   A   G   R   P   L   Q   E   R   V
                                    135                                             162
TTC TTG GTG AAG TTC GTG CGA TCC CGG AGA CCC AGG ACA GCG AGC TGC GCT CTG
 F   L   V   K   F   V   R   S   R   R   P   R   T   A   S   C   A   L
                                    189                                             216
GCT TTC GTG AAC ATG TTG TTG AGG CTA GAG AGG ATC TTG AGA AGA GGG CCG CAC
 A   F   V   N   M   L   L   R   L   E   R   I   L   R   R   G   P   H
                ▼ EXON 2             243                                             270
CGG AAT CCT GGA CCA GGT GAT GAT GAT GGG CAA CGT TCA CGT AGC AGC TCT TCT
 R   N   P   G   P   G   D   D   D   G   Q   R   S   R   S   S   S   S
            SEQ ID NO:5:  M   M   M   G   N   V   H   V   A   A   L   L
                                    297                                             324
GCT CAA CTA CGG TGC AGA TTC GAA CTG CGA GGA CCC CAC TAC CTT CTC CCG CCC
 A   Q   L   R   C   R   F   E   L   R   G   P   H   Y   L   L   P   P
 L   N   Y   G   A   D   S   N   C   E   D   P   T   T   F   S   R   P
                                    351                                             378
GGT GCA CGA CGC AGC GCG GGA AGG CTT CCT GGA CAC GCT GGT GGT GCT GCA CGG
 G   A   R   R   S   A   G   R   L   P   G   H   A   G   G   A   A   R
 V   H   D   A   A   R   E   G   F   L   D   T   L   V   V   L   H   G
```

FIG. 1A

```
                                    405                                              432
GTC AGG GGC TCG GCT GGA TGT GCG CGA TGC CTG GGG TCG CCT GCC GCT CGA CTT

V   R   G   S   A   G   C   A   R   C   L   G   S   P   A   A   R   L
 S   G   A   R   L   D   V   R   D   A   W   G   R   L   P   L   D   L
                                    459                                              486
GGC CCA AGA GCG GGG ACA TCA AGA CAT CGT GCG ATA TTT GCG TTC CGC TGG GTG

G   P   R   A   G   T   S   R   H   R   A   I   F   A   F   R   W   V
 A   Q   E   R   G   H   Q   D   I   V   R   Y   L   R   S   A   G   C
                                    513                                              540
CTC TTT GTG TTC CGC TGG GTG GTC TTT GTG TAC CGC TGG GAA CGT CGC CCA GAC

L   F   V   F   R   W   V   V   F   V   Y   R   W   E   R   R   P   D
 S   L   C   S   A   G   W   S   L   C   T   A   G   N   V   A   Q   T
                                    567                                              594
CGA CGG GCA TAG CTT CAG CTC AAG CAC GCC CAG GGC CCT GGA ACT TCG CGG CCA

R   R   A   ***
 D   G   H   S   F   S   S   S   T   P   R   A   L   E   L   R   G   Q
     3'PRIMER FOR RT-PCR            621                                              648
ATC CCA AGA GCA GAG CTA AAT CCG GCC TCA GGC CGC CTT TTT CTT CTT AGC TTC

S   Q   E   Q   S   ***
                                    675                                              702
ACT TCT AGC GAT GCT AGC GTG TCT AGC ATG TGG CTT TAA AAA ATA CAT AAT AAT
GCT TTT TTT TT
```

FIG. 1B

β transcripts    E1β probe

β transcripts    Exon2 probe

α transcripts    E1α probe

α transcripts    Exon2 probe

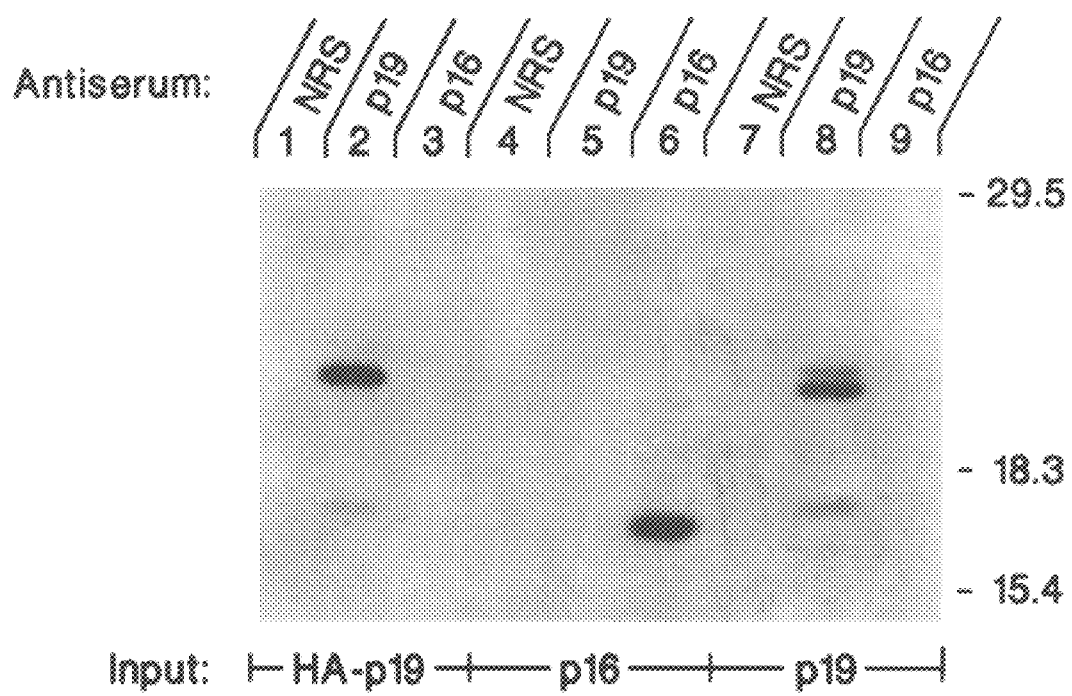

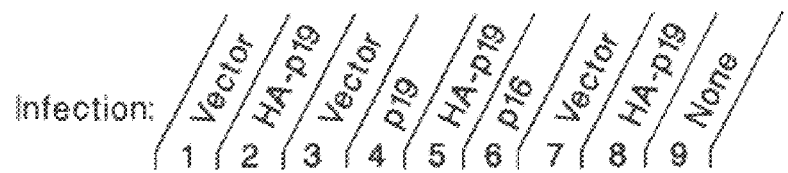

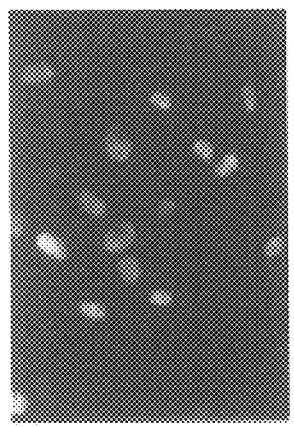
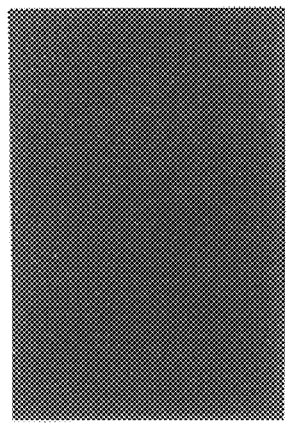
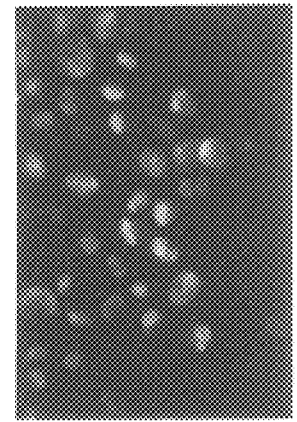
FIG. 5A  Anti-p19
FIG. 5B  Anti-p19 + Peptide
FIG. 5C  Anti-HA

```
                    70           80           90
Mouse  DDDGQR  SRSSSSAQLR  CRFELRGPHY
Human  HDDGQR  PSGGAAAAPR  RGAQLRRPRH
         ■■    T*■V2     ■  HV   R Q
         L3      L
```

```
              100         110          121
LLPPGARRSA  GRLPGHAGGA  ARVRGSAGCAR
SHPTRARRCP  GGLPGHAGGA  APGRGAAGRAR
 ■ S*  V2     E   ■R  D      AL3  ■■2T3*
   L7  Q3         S*              L
   ■   P          A
       L
```

FIG. 6

SEQ ID NO:3:

```
              27                                                           54
    CGC GCC TGC GGG GCG GAG ATG GGC AGG GGG CGG TGC GTG GGT CCC AGT CTG CAG 81                                                          108
    TTA AGG GGG CAG GAG TGG CGC TGC TCA CCT CTG GTG CCA AAG GGC GGC GCA GCG 135                                      162
    GCT GCC GAG CTC GGC CCT GGA GGC GGC GAG AAC ATG GTG CGC AGG TTC TTG GTG
arf                              SEQ ID NO:4:  M   V   R   R   F   L   V 189                                                         216
    ACC CTC CGG ATT CGG CGC GCG TGC GGC CCG CCG CGA GTG AGG GTT TTC GTG GTT
arf  T   L   R   I   R   R   A   C   G   P   P   R   V   R   V   F   V   V 243                                                         270
    CAC ATC CCG CGG CTC ACG GGG GAG TGG GCA GCG CCA GGG GCG CCC GCC GCT GTG
arf  H   I   P   R   L   T   G   E   W   A   A   P   G   A   P   A   A   V 297                                                         324
    GCC CTC GTG CTG ATG CTA CTG AGG AGC CAG CGT CTA GGG CAG CAG CCG CTT CCT
arf  A   L   V   L   M   L   L   R   S   Q   R   L   G   Q   Q   P   L   P 351                                                         378
    AGA AGA CCA GGT CAT GAT GAT GGG CAG CGC CCG AGT GGC GGA GCT GCT GCT GCT
arf  R   R   P   G   H   D   D   G   Q   R   P   S   G   G   A   A   A   A
p16                      M   M   M   G   S   A   R   V   A   E   L   L   L   L 405                                                         432
    CCA CGG CGC GGA GCC CAA CTG CGC CGA CCC CGC CAC TCT CAC CCG ACC CGT GCA
arf  P   R   R   G   A   Q   L   R   R   P   R   H   S   H   P   T   R   A
p16  H   G   A   E   P   N   C   A   D   P   A   T   L   T   R   P   V   H 459                                                         486
    CGA CGC TGC CCG GGA GGG CTT CCT GGA CAC GCT GGT GGT GCT GCA CCG GGC CGG
arf  R   R   C   P   G   G   L   P   G   H   A   G   G   A   A   P   G   R
p16  D   A   A   R   E   G   F   L   D   T   L   V   V   L   H   R   A   G 513                                                         540
    GGC GCG GCT GGA CGT GCG CGA TGC CTG GGG CCG TCT GCC CGT GGA CCT GGC TGA
arf  G   A   A   G   R   A   R   C   L   G   P   S   A   R   G   P   G   *
p16  A   R   L   D   V   R   D   A   W   G   R   L   P   V   D   L   A
```

FIG. 7

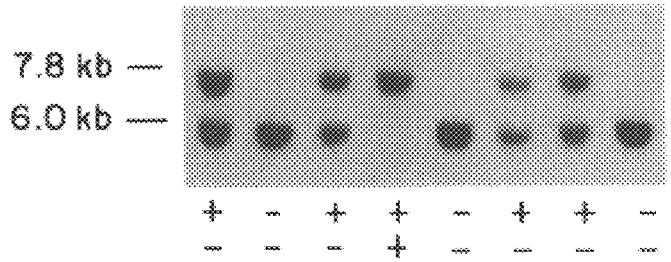
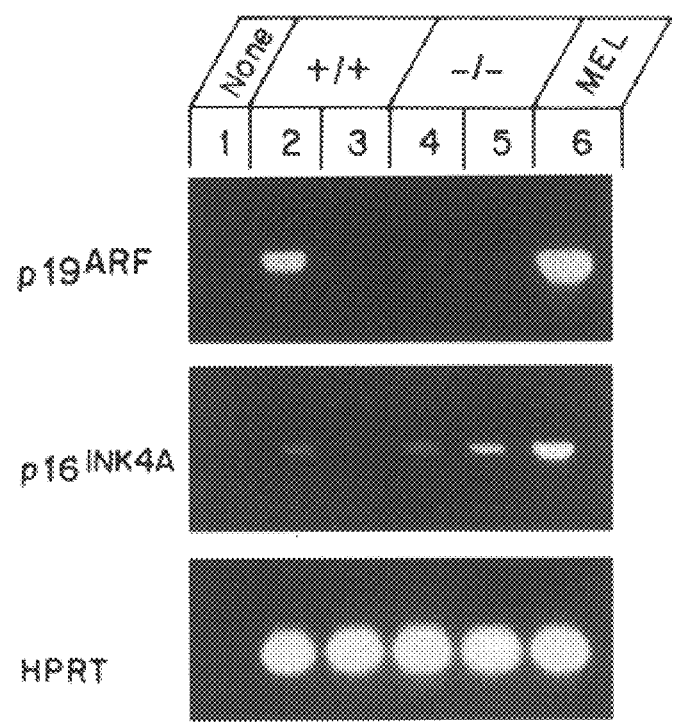

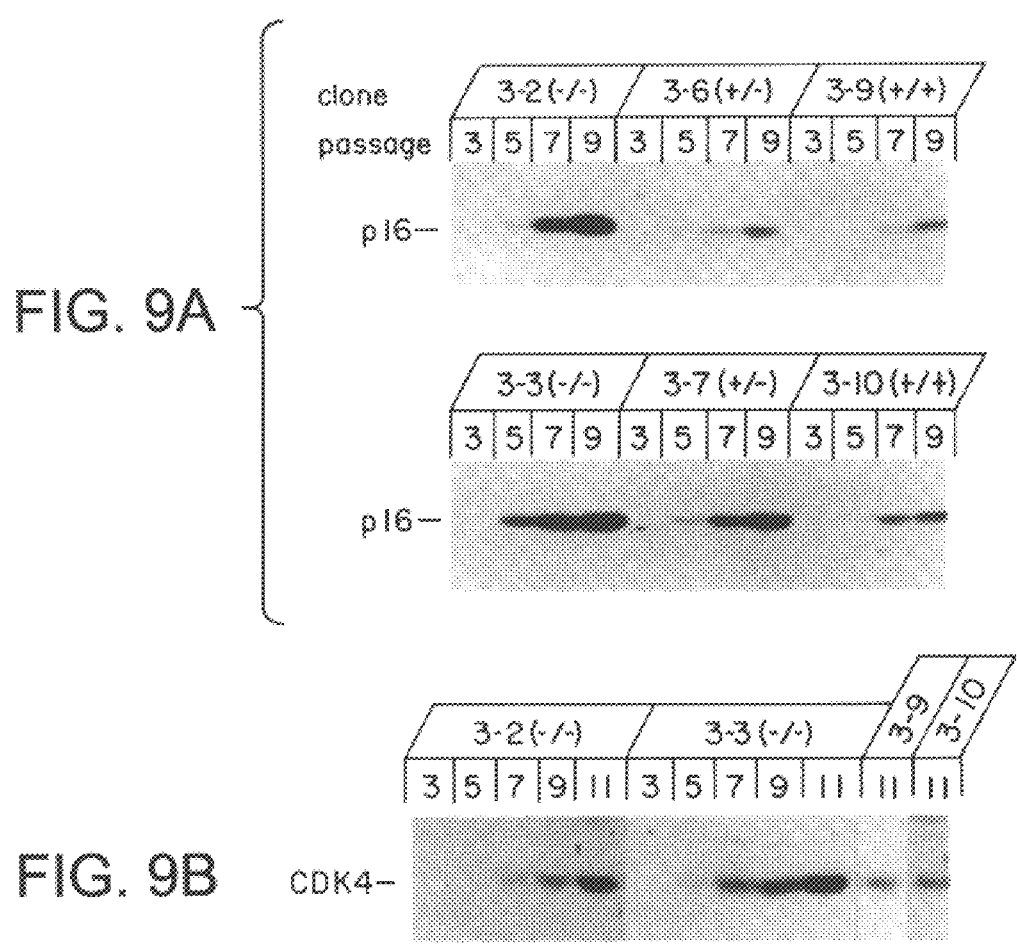

Wild-Type p53

Mutant p53

Triple Infection

FIG. 19
p19ARF
Passage: 2 3 4 5 6 7
wild-type
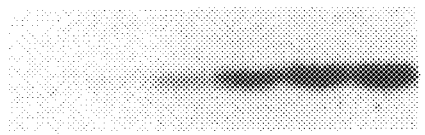
p53-null
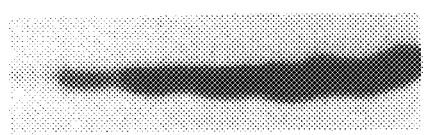
p21-null
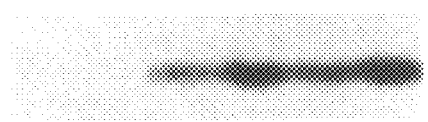
Rb-null

ARF-P19, A NOVEL REGULATOR OF THE MAMMALIAN CELL CYCLE

CROSS-REFERENCE TO RELATED APPLICATIONS

The present Application is a Continuation-In-Part of U.S. Ser. No. 08/954,470 filed Oct. 20, 1993, now U.S. Pat. No. 5,876,965, issued Mar. 2, 1999 which is a Divisional of U.S. Ser. No. 08/534,975 filed on Sep. 27, 1995 now U.S. Pat. No. 5,723,313, issued Mar. 3, 1998, the disclosures of which are hereby incorporated by reference in their entireties. Applicants claim the benefit of these Applications under 35 U.S.C. §120.

STATEMENT AS TO RIGHTS TO INVENTIONS MADE UNDER FEDERALLY-SPONSORED RESEARCH AND DEVELOPMENT

This invention was made with U.S. Government support under Cancer Center CORE grant 5P30CA21765-18, awarded by the National Cancer Institute. The U.S. Government has certain rights in this invention. Support for this invention was also provided by the Howard Hughes Medical Institute and the American Lebanese Syrian Associated Charities of St. Jude Children's Research Hospital.

FIELD OF THE INVENTION

This invention relates to cancer detection and treatment and, more particularly, to a novel protein called "$p19^{ARF}$ protein," "$p19^{ARF}$," "$^{ARF}p19$" or simply "ARF" that is involved in regulation of the eukaryotic cell cycle. Protein ARF-p19 is encoded by a nucleic acid derived from the gene, INK4A, which also encodes an inhibitor of D-type cyclin-dependent kinases called "$p16^{InK4a}$ protein," "$p16^{InK4a}$" or simply "InK4a-p16."

Transcripts encoding InK4a-p16 originate from a first promoter, E1a; the present invention is based on the observation that some INK4A transcripts initiate from a second promoter, E1b, and contain an Alternative Reading Frame, ARF, which overlaps the INK4a-p16 reading frame to some degree. ARF transcripts direct the production of a protein that has ARF-p19 amino acid sequences instead of the previously-known InK4a-p16 sequences. Like InK4a-p16, ARF-p19 regulates the eukaryotic cell cycle. When overexpressed, ARF-p19 inhibits cells from proceeding past both the G1 and G2 phases of the cell cycle. However, the mechanism(s) by which ARF-p19 acts are unlike those of InK4a-p16, which acts by directly and specifically interacting with CDK (cyclin D-dependent kinase) proteins and thus preventing CDK-cyclin D interactions.

In addition to (1) ARF-p19 proteins, this invention further relates to (2) nucleic acids that encode ARF-p19 isolated from mice, humans and other mammals; (3) antibodies that specifically bind ARF-p19 protein or polypeptides derived therefrom; (4) methods for detecting one or more nucleic acids encoding ARF-p19, or alterations in such nucleic acids; (5) methods for producing ARF-p19 proteins using nucleic acids that encode ARF-p19; (6) purified ARF-p19 proteins, or fusion proteins derived from the joining of an ARF-p19 polypeptide sequence with a second polypeptide sequence; (7) methods of treating cancer using purified ARF-p19 proteins or fusion proteins derived therefrom; (8) methods of inducing cell cycle arrest using ARF-p19 proteins or nucleic acids encoding ARF-p19 proteins; (9) methods for detecting ARF-p19 proteins using antibodies that specifically bind ARF-p19 proteins; (10) methods of selectively killing cells having uncontrolled growth using antibodies that specifically bind ARF-p19 proteins, or conjugates derived from such antibodies; (11) methods of stimulating cell growth using antibodies that specifically bind ARF-p19 proteins, or fragments derived from such antibodies; and (12) transgenic non-human animals that have a genetically engineered alteration in one or more nucleic acids encoding ARF-p19 proteins but which express normal levels of wild-type InK4a-p16 protein, or which overexpress human ARF-p19 or mutant forms of ARF-p19.

BACKGROUND OF THE INVENTION

Neoplasia, the pathological process by which tumors develop, necessarily involves unregulated, or at best misregulated, cellular growth and division. The molecular pathways that regulate cellular growth must inevitably intersect with those that regulate the cell cycle. The cell cycle consists of a cell division phase and the events that occur during the period between successive cell divisions, known as interphase. Interphase is composed of successive G1, S, and G2 phases, and normally comprises 90% or more of the total cell cycle time. Most cell components are made continuously throughout interphase; it is therefore difficult to define distinct stages in the progression of the growing cell through interphase. One exception is DNA synthesis, since the DNA in the cell nucleus is replicated only during a limited portion of interphase. This period is denoted as the S phase (S=synthesis) of the cell cycle. The other distinct stage of the cell cycle is the cell division phase, which includes both nuclear division (mitosis) and the cytoplasmic division (cytokinesis) that follows. The entire cell division phase is denoted as the M phase (M=mitotic). This leaves the period between the M phase and the start of DNA synthesis, which is called the G1 phase (G=gap), and the period between the completion of DNA synthesis and the next M phase, which is called the G2 phase (Alberts, B. et al., *Molecular Biology of the Cell*, Garland Publishing, Inc., New York & London (1983), pages 611–612).

Progression through different transitions in the eukaryotic cell cycle is positively regulated by a family of master enzymes, the cyclin-dependent kinases (reviewed by Sherr, C.J., *Cell* 73:1059–1065 (1993)). These holoenzymes are composed of two proteins, a regulatory subunit (the cyclin), and an associated catalytic subunit (the actual cyclin-dependent kinase or CDK), the levels of which vary with different phases of the cell cycle (Peters, O., *Nature* 371:204–205 (1994)). Both cyclins and CDKs represent molecular families that encompass a variety of genetically related but functionally distinct proteins. Generally, different types of cyclins are designated by letters (i.e., cyclin A, cyclin B, cyclin D, cyclin E, etc.); CDKs are distinguished by numbers (CDK1, CDK2, CDK3, CDK4, CDK5, etc.; CDK1 is a.k.a. CDC2).

CDK-cyclin D complexes regulate the decision of cells to replicate their chromosomal DNA (Sherr, *Cell* 73:1059–1065 (1993)). As cells enter the cycle from quiescence, the accumulation of CDK-cyclin D holoenzymes occurs in response to mitogenic stimulation, with their kinase activities being first detected in mid-G1 phase and increasing as cells approach the G1/S boundary (Matsushime et al., *Mol. Cell. Biol.* 14:2066–2076 (1994); Meyerson and Harlow, *Mol. Cell. Biol.* 4:2077–2086 (1994)). The cyclin D regulatory subunits are highly labile, and premature withdrawal of growth factors in G1 phase results in a rapid decay of CDK-cyclin D activity that correlates with the failure to enter S phase. In contrast, removal of growth factors late in G1 phase, although resulting in a similar collapse of CDK-cyclin D activity, has no effect on further progression through the cell cycle (Matsushime et al., *Cell* 65:701–713 (1991)). Microinjection of antibodies to cyclin D1 into fibroblasts during G1 prevents entry into the S phase, but injections performed at or after the G1→S transition are without effect (Baldin et al., *Genes & Devel.* 7:812–821 (1993); Quelle et al., *Genes & Devel.* 7:1559–1571 (1993)). Therefore, CDK-cyclin D complexes execute their critical functions at a late G1 checkpoint, after which cells become independent of mitogens for completion of the cycle.

In mammals, cells enter the cell cycle and progress through G1 phase in response to extracellular growth signals which trigger the transcriptional induction of D-type cyclins. The accumulation of D cyclins leads to their association with two distinct catalytic partners, CDK4 and CDK6, to form kinase holoenzymes. Several observations argue for a significant role of the cyclin D-dependent kinases in phosphorylating the retinoblastoma protein, pRb, leading to the release of pRB-associated transcription factors that are necessary to facilitate progression through the G1→S transition. First, CDK-cyclin D complexes have a distinct substrate preference for pRb but do not phosphorylate the canonical CDK substrate, histone H1 (Matsushime et al., *Cell* 71:323–334 (1992); Matsushime et al., *Mol. Cell. Biol.* 14:2066–2076 (1994); Meyerson and Harlow, *Mol. Cell. Biol.* 14:2077–2086 (1994)). Their substrate specificity may be mediated in part by the ability of D-type cyclins to bind to pRb directly, an interaction which is facilitated by a Leu-X-Cys-X-Glu pentapeptide that the D cyclins share with DNA oncoproteins that also bind pRb (Dowdy et al., *Cell* 73:499–511 (1993); Ewen et al., *Cell* 73:487497 (1993); Kato et al., *Genes & Devel.* 7:331–342 (1993)). Second, cells in which pRb function has been disrupted by mutation, deletion, or after transformation by DNA tumor viruses are no longer inhibited from entering S phase by microinjection of antibodies to D cyclin, indicating that they have lost their dependency on the cyclin D-regulated G1 checkpoint (Lukas et al., *J. Cell. Biol.* 125:625–638 (1994); Tam et al., *Oncogene* 9:2663–2674 (1994)). However, introduction of pRb into such cells restores their requirement for cyclin D function (Lukas et al., *J. Cell. Biol.* 125:625–638 (1994)). Third, pRb-negative cells synthesize elevated levels of a 16 kDa polypeptide inhibitor of CDK4, "p16$^{InK4a}$" (aka. "InK4a-p16" or simply "p16"), which is a member of a recently discovered class of cell cycle regulatory proteins (Nasmyth and Hunt, *Nature* 366:634–635 (1993); Peters, C., *Nature* 371:204–205 (1994)) and which is found in complexes with CDK4 at the expense of D-type cyclins during G1 phase (Bates et al., *Oncogene* 9:1633–1640 (1994); Serrano et al., *Nature* 366:704–707 (1993); Xiong et al., *Genes & Devel.* 7:1572–1583 (1993)). The fact that such cells cycle in the face of apparent CDK4 inhibition again implies that D-type cyclins are dispensable in the Rb-negative setting.

The InK4 gene family ("InK4" signifies Inhibitors of CDK4) is known to include at least three other low molecular weight polypeptides, InK4b-p15, induced in human epithelial cells treated with transforming growth factor-β (TGF-β) (Hannon, G.J., and Beach, D., *Nature* 371:257–261 (1994)), InK4d-p19 (Hirai, H., et al., *Mol. Cell. Biol.* 15:2672–2681 (1995)) and InK4c-p15 (Guan et al., *Genes & Develop.* 8:2939–2952 (1994); Hirai, H., et al., *Mol. Cell. Biol.* 15:2672–2681 (1995)). InK4d-p19 and InK4c-p18 are described in detail in Ser. No. 08/384,106, filed Feb. 6, 1995, which is hereby incorporated by reference.

Members of the InK4 family are typically composed of repeated ankyrin motifs, each of about 32 amino acids in length. All known members of the InK4 family act to specifically inhibit enzymatic activities of D-type cyclin-dependent kinases such as CDK4 and CDK6. Unlike other universal CDK inhibitors, such as p21$^{Cip1/Waf1}$ (El-Deiry et al., *Cell* 75:817–825 (1993); Gu et al., *Nature* 366:707–710 (1993); Harper et al., *Cell* 75:805–816 (1993); Xiong et al., *Nature* 366:701–704 (1993)) and p27$^{Kip1}$ (Polyak et al., *Genes & Devel.* 8:9–22 (1994); Polyak et al., *Cell* 78:59–66 (1994); Toyoshima and Hunter, *Cell* 78:67–74 (1994)), the InK4 proteins selectively inhibit the activities of CDK4 and CDK6, but do not inhibit the activities of other CDKs Guan et al., *Genes & Devel.* 8:2939–2952 (1994); Hannon and Beach, *Nature* 371:257–261 (1994); Serrano et al., *Nature* 366:704–707 (1993)).

Like many CDK inhibitors (CKIs) (Nasmyth and Hunt, *Nature* 366:634–635 (1993)), InK4 family members negatively regulate progression through the mammalian cell cycle, in part in response to anti-proliferative extracellular signals. The InK4 proteins, by inhibiting the activities of a specific class of the D-type cyclin-dependent kinases (i.e., CDK4 and/or CDK6), arrest cell cycle progression in G1 phase and thus prevent cells from replicating their chromosomal DNA. Thus, in contradistinction to the positive regulation of D-type cyclin synthesis by growth factors, extracellular inhibitors of G1 progression can negatively regulate the activity of D-type cyclin-dependent kinases by inducing InK4 proteins.

RELATED ART

Mullis et al., U.S. Pat. No. 4,965,188 (Oct. 23, 1990), describe methods for amplifying nucleic acid sequences using the polymerase chain reaction (PCR).

Beach, published PCT patent application WO 92/20796 (Nov. 26, 1992), describes genes encoding D cyclins and uses thereof.

Berns, U.S. Pat. No. 5,174,986 (Dec. 29, 1992), describes methods for determining the oncogenic potential of chemical compounds using a transgenic mouse predisposed to develop T-cell lymphomas.

Crissman et al., U.S. Pat. No. 5,185,260 (Feb. 9, 1993), describe methods for distinguishing and selectively killing transformed (neoplastic) cells using synthetic G1 kinase inhibitors.

Stone, S., et al., *Cancer Research* 55:2988–2994 (1995), describe two cDNAs derived from the human INK4A gene, including an "a form," encoding InK4a-p16 and a "b form" that includes an open reading frame (designated "ORF 2") that overlaps the reading frame encoding the ARF-p19 protein described herein. Stone et al. state that it "is unknown if ORF 2 encodes a protein" (legend to FIG. 1, page 2990) and indicate that "ORF 2 has not been selectively maintained and probably does not encode a protein" (page 2989, column 2, lines 20–21).

Mao, L., et al., *Cancer Research* 55:2995—2997 (1995), describe two transcripts and corresponding cDNAs derived from the human INK4A gene, designated "p16" and "p16b." The p16 transcript is stated to encode the InK4a-p16 protein, while the p16b transcript is stated to contain a "theoretical open reading frame" (page 1996, column 1, line 47) that is not further defined, and suggest this sequence "probably represents an untranslated open reading frame" (page 2997, column 2, lines 9–10). Mao et al., state that the in vitro transcription and translation (TNT) product of the p16b cDNA is recognized by an antibody to InK4a-p16 polypeptide sequences (page 2997, column 1, lines 6), suggesting that the p16b transcript encodes an amino-terminal truncated InK4a-p16 polypeptide rather than a protein having, as ARF-p19 does, an amino acid sequence unrelated to that of InK4a-p16. However, Mao et al. also state that, using InK4a-p16 antiserum, they are unable to identify, an amino-terminal truncated p16b protein in cell lines (page 2997, column 2, lines 1–2). Thus, Mao et al. are silent regarding the ARF-p19 protein described herein.

SUMMARY OF THE INVENTION

The present invention relates to the discovery in mammalian cells of a novel cell cycle regulatory protein, having a predicted molecular mass of 19 kDa, here designated "ARF-p19 protein", "ARF-p19" or simply "ARF". In particular, the invention relates to ARF-p19 proteins isolated from cells derived from a mouse or a human. Although derived from the gene encoding the previously-known InK4a-p16 protein, ARF-p19 arises by differential transcription and translation of InK4a-p16 sequences. That is, ARF-p19 is encoded by an alternative reading frame (ARF) and the full length protein has an amino acid sequence (SEQ ID NO:2; SEQ ID NO:4) that is wholly unrelated to that of InK4a-p16. Surprisingly, however, ARF-p19 protein functions to regulate the cell cycle in a similar but less specific manner than, and by a mechanism distinct from that of InK4a-p16 protein.

Thus, one aspect of the invention is directed to methods of using the ARF-p19 proteins or active fragments thereof (such as the peptide encoded by exon 1β) of the invention to inhibit the growth of cancer cells and/or to prevent cancer cells from replicating their chromosomal DNA. Both InK4-p16 and InK4-p15 appear to act as tumor suppressors (Nobvri, T. et al., Nature 368:752–756 (1994); Kamb, A. et al., Science 264:436–440 (1994)). The genes encoding p16 and p15 map in a tandem array to the short arm of human chromosome 9 within a region that is frequently deleted in cancer cells, and the resulting loss of their anti-proliferative functions can contribute to tumorigenesis (Noburi et al., Nature 368:753–756 (1994); Okuda, T., et al., Blood 85:2321–2330 (1995)). The novel ARF-p19 protein described herein (1) plays a role in preventing the G1→S and G2→M phase transitions in normal mammalian cells, and (2) if having reduced or altered activity due to one or more mutations affecting the alternative reading frame encoding ARF-p19, could contribute to oncogenesis in some cancers, even if such mutations have no effect on the reading frame encoding InK4a-p16. Indeed, as described herein, ARF-p19 and active fragments thereof can act as tumor suppressors.

In another aspect, the invention provides nucleic acid sequences encoding ARF-p19 polypeptides and active fragments thereof from mice, humans and other mammals. The nucleic acid sequences of the invention may be expressed in the form of isolated nucleic acids, such as cDNA clones, genomic DNA clones, mRNA transcribed from either cDNA or genomic DNA clones, synthetic oligonucleotides, and/or synthetic amplification products resulting from PCR, and may be single-stranded or double-stranded.

In a related aspect, the invention provides methods for detecting nucleic acids encoding wild-type or mutant ARF-p19 proteins and active fragments thereof using the nucleic acid sequences of the invention described above. The detection of point mutations, deletions of, or other mutations in, the reading frame encoding ARF-p19 is predictive of a predisposition to, or diagnostic of, certain types of cancer.

In another related aspect the DNA molecules of the invention described above may be cloned into expression vectors and placed in an appropriate host in order to produce ARF-p19 proteins, active fragments thereof or fusion proteins containing ARF-p19 polypeptide sequences or active fragments thereof. When placed in an animal that has cancer, this aspect of the invention relates to gene therapy for certain types of cancers.

In another aspect, the invention provides antibody compositions that bind specifically to ARF-p19 proteins and/or polypeptides derived therefrom. The antibody compositions of the invention may be polyclonal, monoclonal, or mono-specific. Although all of the antibody compositions of the invention bind specifically to ARF-p19, some compositions bind to a specific epitope of ARF-p19 and thereby inhibit a specific function of ARF-p19.

In a related aspect, the invention provides methods for detecting ARF-p19 proteins using the antibody compositions described above. The detection of reduced amounts of, or altered forms of, ARF-p19 proteins is predictive of a predisposition to, or diagnostic of, certain types of cancer.

In another aspect the invention provides transgenic non-human animals which have one or more mutations in the endogenous reading frame encoding ARF-p19, wherein said mutation results in the production of a mutant ARF-p19 protein or results in a loss of ARF-p19 expression but does not significantly affect the InK4a-p16 gene product or expression thereof. Additionally or alternatively, the transgenic non-human animals of the invention express a human wild-type or mutant ARF-p19. Because of the transgene(s) introduced into the genome of the non-human animals of the invention, the animals have a reduced and/or altered ARF-p19 activity compared to wild-type animals, and consequentially develops certain types of cancers, particularly melanomas, in a reproducible and thus predictable manner.

In a related aspect, compositions are evaluated for their potential to enhance or inhibit certain types of cancers, particularly melanomas, using the transgenic non-human animals of the invention.

In addition the present invention provides a complex, preferably an isolated complex, comprising p53, or a fragment thereof, bound to a ARF-p19 peptide or protein comprising at least 10, preferably at least 25, and more preferably at least 62 contiguous amino acid residues of the amino acid sequence of SEQ ID NO:2 or SEQ ID NO:4. In a related embodiment, the complex comprises p53, or a fragment thereof, bound to a peptide or protein comprising at least 10, preferably at least 25, and more preferably at least 62 contiguous amino acid residues of the amino acid sequence of amino acids 1–84 of SEQ ID NO:2 or amino acids 1–84 of SEQ ID NO:4. In still another embodiment the complex comprises p53, or a fragment thereof, bound to a peptide or protein comprising at least 10, preferably at least 25, and more preferably 62 contiguous amino acid residues of the amino acid sequence of amino acids 1–62 of SEQ ID NO:2 or amino acids 1–62 of SEQ ID NO:4. In yet another embodiment, the complex comprises p53, or a fragment thereof bound to the peptide encoded by exon 1β of the INKa-ARF locus of the mouse ARF-p19 (SEQ ID NO:2) or the human ARF-p19 (SEQ ID NO:4). In a particular embodiment the complex further comprises mdm2 and/or an oligonucleotide. p53 or the p53 fragment, or the ARF-p19 peptide or protein also can be a part of a fusion protein. In addition, any of the proteins and peptides included in the complexes can be recombinant proteins.

The present invention also provides methods of identifying an agent that modulates the binding of ARF-p19 and p53. One such method comprises contacting ARF-p19 or an ARF-p19 fragment with p53 or p53 fragment in the presence of a candidate agent, and determining the binding of p53 or the p53 fragment with ARF-p19 or the ARF-p19 fragment. The ARF-p19 fragment binds to p53 in the absence of the agent, and the p53 fragment binds to ARF-p19 in the absence of the agent. Preferably, the ARF-p19 fragment binds to the p53 fragment in the absence of the agent. When the binding of p53 or the p53 fragment with ARF-p19 or the ARF-p19 fragment is modulated, a candidate agent is identified as an agent that modulates the binding of ARF-19 with p53. In one such embodiment, when the modulation of the binding of p53 or the p53 fragment with ARF-p19 or the ARF-p19 fragment leads to a decrease in the binding affinity, the agent is identified as an inhibitor of p53 binding with ARF-p19. In another such embodiment, when the modulation of the binding of p53 or the p53 fragment with ARF-p19 or the ARF-p19 fragment leads to an increase in the binding affinity, the agent is identified as an agonist of p53 binding with ARF-p19. In a particular embodiment the ARF-p19 fragment is a peptide comprising at least 10, preferably at least 25, and more preferably at least 62 contiguous amino acid residues of the amino acid sequence of SEQ ID NO:2 or SEQ ID NO:4. In another embodiment the ARF-p19 fragment is encoded by exon 1β of the INKa-ARF locus of the mouse ARF-p19 (SEQ ID NO:2) or the human ARF-p19 (SEQ ID NO:4). In a related embodiment the ARF-p19 or ARF-p19 fragment is part of a fusion protein. In addition, any of the proteins and peptides can be recombinant proteins.

The present invention further provides methods of preventing abnormal cell growth. In one such embodiment the method comprises administering an effective amount of ARF-p19 or a ARF-p19 fragment that can act as a tumor suppressor in a cell. In a preferred embodiment, the cell is responding to an hyperproliferative signal and the cell contains a functional (e.g., a wildtype) p53. In one embodiment of this type the hyperproliferative signal is due to an oncogene. In a particular embodiment of this type the oncogene is MYC. In one embodiment the ARF-p19 fragment is a peptide comprising at least 10, preferably at least 25, and more preferably at least 62 contiguous amino acid residues of the amino acid sequence of SEQ ID NO:2 or SEQ ID NO:4. In another embodiment the ARF-p19 fragment is encoded by exon 1β of the INKa-ARF locus of the mouse ARF-p19 (SEQ ID NO:2) or the human ARF-p19 (SEQ ID NO:4). In a related embodiment the ARF-p19 or ARF-p19 fragment is part of a fusion protein. In addition, any of the proteins and peptides can be recombinant proteins. The ARF-p19 or ARF-p19 fragment can be administered to the cell either by contacting the protein or peptide to the cell, or alternatively by introducing an expression vector into the cell that encodes the ARF-p19 or ARF-p19 fragment and that expresses an effective amount of the protein or peptide.

The present invention also provides methods of treating an animal (preferably a mammal) that has a tumor and/or cancer. One such method includes administering an effective amount of a pharmaceutical composition that comprises a pharmaceutically acceptable carrier and ARF-p19 on ARF-p19 fragment that can act as a tumor suppressor in the cell. In a preferred embodiment, the animal contains a cell that is responding to an hyperproliferative signal and the cell contains a functional (e.g., a wildtype) p53. In one embodiment of this type the hyperproliferative signal is due to an oncogene. In a particular embodiment of this type the oncogene is MYC. In one embodiment the ARF-p19 fragment is a peptide comprising at least 10, preferably at least 25, and more preferably at least 62 contiguous amino acid residues of the amino acid sequence of SEQ ID NO:2 or SEQ ID NO:4. In another embodiment the ARF-p19 fragment is encoded by exon 1β of the INKa-ARF locus of the mouse ARF-p19 (SEQ ID NO:2) or the human ARF-p19 (SEQ ID NO:4). In a related embodiment the ARF-p19 or ARF-p19 fragment is part of a fusion protein. In addition, any of the proteins and peptides can be recombinant proteins. The present invention also provides corresponding pharmaceutical compositions comprising an ARF-p19 or an ARF-p19 fragment that can act as a tumor suppressor; and a pharmaceutically acceptable carrier. Alternatively the ARF-p19 or ARF-p19 fragment can be administered by introducing an expression vector into the animal that encodes the ARF-p19 or ARF-p19 fragment and expresses an effective amount of the protein or peptide.

Also part of the present invention is an in vitro method for monitoring a therapeutic treatment of a tumor and/or cancer in an animal, preferably a mammalian subject. One such embodiment comprises evaluating the levels of ARF-p19 or an active ARF-p19 fragment in a series of biological samples obtained at different time points from a mammalian subject undergoing a therapeutic treatment for the tumor or cancer.

The present invention further provides methods of identifying an agent that can act as a tumor supressor in a cell. In one such embodiment the agent is contacted with the cell and the amount of cellular proliferation is determined. A decrease in cellular proliferation of the cell in the presence of the agent is indicative that the agent is a tumor suppressor. In a particular embodiment of this type the cell contains an homozygous disruption in its endogenous exon 1β of the INK4a-ARF locus. In one such embodiment the INK4a exon 1α and the tandemly linked INK4b locus remain intact, so that the cell does not express endogenous exon 1β, but can express $p16^{INK4a}$ and functional (e.g., wildtype)p53). In a preferred embodiment, the animal contains a cell that is responding to an hyperproliferative signal. In one embodiment of this type the hyperproliferative signal is due to an oncogene. In a particular embodiment of this type the oncogene is MYC.

The present invention further provides a method of identifying an agent that can stimulate the apoptosis of cells. One such method comprises culturing the cells in a serum-free medium in the presence and absence of the agent and determining the amount of apoptosis of the cells. An agent is selected as stimulating apoptosis when the amount of apoptosis in the presence of the agent is greater than in its absence. In a particular embodiment of this type the cell contains an homozygous disruption in its endogenous exon 1β of the INK4a-ARF locus. In one such embodiment the INK4a exon 1α and the tandemly linked INK4b locus remain intact, so that the cell does not express endogenous exon 1β, but can express $p16^{INK4a}$ and functional (e.g., wildtype) p53. In a preferred embodiment, the animal contains a cell that is responding to an hyperproliferative signal. In one embodiment of this type the hyperproliferative signal is due to an oncogene. In a particular embodiment of this type the oncogene is MYC. In a preferred embodiment of this type the method further comprises the step of introducing the oncogene into the cells by a viral vector. In a related embodiment the method further includes the step of inducing the expression of the oncogene by culturing the cells containing the viral vector with an inducer of the expression of the oncogene prior to culturing the cells in a serum-free medium.

As indicated above, the present invention provides transgenic knockout animals which are missing a functional ARF-p19. One such embodiment comprises a homozygous disruption in the endogenous exon 1β of the INK4a-ARF locus of the animal. The resulting knockout animal is particularly susceptible to developing spontaneous tumors. In one such embodiment the INK4a exon 1α and the tandemly linked INK4b locus remain intact, so that the cell does not express endogenous exon 1β, but can express p16$^{INK4a}$ and functional (e.g., wildtype) p53. In a particular embodiment the transgenic knockout animal is a knockout mouse. The present invention also provides cultured cell lines derived from the knockout animals of the present invention. In addition, the present invention provides an embryo fibroblast comprising a homozygous disruption in its endogenous exon 1β of the INK4a gene. In one such embodiment the INK4a exon 1α and the tandemly linked INK4b locus remain intact, so that the cell does not express endogenous exon 1β, but can express p16$^{INK4a}$ and functional (e.g., wildtype) p53. In a preferred embodiment of this type the embryo fibroblast is a mouse embryo fibroblast.

The present invention further provides a method for diagnosing a cell sample comprising a cell suspected of being cancerous or prone to becoming cancerous due to a mutation, deletion, or insertion in an endogenous nucleic acid encoding ARF-p19. One such embodiment comprises preparing a nucleotide sample from the cell and detecting the mutation, the deletion, or the insertion with a test nucleic acid having the nucleotide sequence of SEQ ID NO:1 or a portion thereof, or SEQ ID NO:3 or a portion thereof. When the mutation, the deletion, or the insertion is detected, the presence of the mutation, the deletion, or the insertion of the endogenous nucleic acid encoding ARF-p19 is diagnosed. In one embodiment a DNA sample is prepared. In a related embodiment an RNA sample is prepared. In a preferred embodiment the portion of the nucleotide sequence of SEQ ID NO:1 or SEQ ID NO:3 is derived from a nucleotide sequence that is not found in p16InK4a mRNAs. In one embodiment, the test nucleic acid is a nucleotide probe that can be used to hybridize with the nucleotide sample. In another embodiment, the test nucleic acid is a nucleic acid primer that can he used in PCR analysis. In a preferred embodiment the cell is suspected of responding to an hyperproliferative signal. In one embodiment of this type the hyperproliferative signal is suspected to be due to an oncogene. In a particular embodiment of this type the oncogene is MYC.

BRIEF DESCRIPTION OF THE FIGS.

FIG. 1 shows the sequence of a murine cDNA molecule (SEQ in No:1) homologous to human INK4A b transcripts and the sequence of the polypeptide, ARF-p19 (SEQ ID NO:2), encoded thereby; the partial carboxy-terminal amino acid sequence of InK4a-p16 (SEQ ID NO:5), encoded by exons 2 and 3 in INK4A a transcripts, is also indicated. Sequences from exon 1β (nucleotides 1–232) are spliced to exon 2 to create an open reading frame capable of encoding a novel 169 amino acid protein (ARF-p19). The initiator codon for ARF-p19 occurs at nucleotides 43–45, and a putative UAG stop codon is found at nt 550–552. Nucleotides 436–438 (double underlined CCA) are replaced by a TGA termination codon in corresponding position in the human INK4A gene (Serrano et al., Nature 366:704–707 (1993)); accordingly, the human ARF-p19 protein is truncated relative to the murine ARF-p19 protein. Unrelated sequences from exon 1β (not shown) are spliced to the same exon 2 acceptor site to open another reading frame that encodes InK4a-p16. Exon 2-coded InK4a-p16 amino acid sequences are shown below those of ARF-p19. The carboxyl terminus of mouse InK4a-p16 is 20 residues longer than the human polypeptide (Quelle et al., Oncogene 11:635–645 (1995)), with the last four amino acids of the latter encoded by a third exon (Kamb, A. et al., Science 264:436–440 (1994a)). The location of residues corresponding to the primers used to specifically amplify β transcripts by RT-PCR (FIG. 2) are underlined.

FIG. 2 (panels A–D) shows the results of RT-PCR assays of INK4A α and β mRNA transcripts in mouse tissues and the mouse MEL cell line. Equivalent quantities of RNA from the indicated tissues were amplified in parallel by RT-PCR using 5' primers specific for α or β transcripts and a common 3' primer (FIG. 1). Products from β (panels A, B) and α (panels C, D) RT templates were hybridized with specific exon 1β (panel A), exon 1α (panel C), or exon 2 probes (panels B, D). Autoradiographic exposure times were 2 hrs.

FIG. 3 shows the results of immunoassays using antibodies to the carboxyl-terminal portion of ARF-p19 (p19 antiserum) or antibodies to InK4a-p16 (p16 antiserum) and the detection of InK4a-p16 (p16), ARF-p19 (p19) or ARF-p19 tagged with hemagglutinin (HA-p19). cDNAs encoding InK4a-p16, ARF-p19, and HA-tagged ARF-p19 (as indicated below the panel) were transcribed and translated in vitro. Proteins labeled with [$^{35}$S]-Methionine, normalized for equal input of radioactivity, were precipitated with nonimmune rabbit serum (NRS) or with antisera to InK4a-p16 or ARF-p19 (as indicated at the top) and separated on denaturing gels. The positions of marker proteins of known molecular mass are indicated at the right.

FIG. 4 (panels A–C) shows the results of immunoassays using antibodies specific for ARF-p19. InK4a-p16, or hemagglutinin (HA). Cell lysates (indicated at the bottom of panel C) were divided into three equal aliquots, separated on denaturing gels, and immunoblotted with antibodies specific for ARF-p19 (panel A), HA (panel B) or InK4a-p16 (panel C). The cell lines indicated on the bottom of the FIG. (Sf9=insect cells in which baculoviral expression occurs; N3T3-d=NIH-3T3 cells genetically engineered to overexpress cyclin D1; B3T3=derivative of Balb-3T3 cells; MEL= mouse erythroleukemia cells) were either uninfected ("none") or infected with appropriate expression constructs expressing ARF-p19 ("p19"), ARF-p19 tagged with hemagglutinin ("HA-p19"), or InK4a-p16 ("p16"). Cells were infected for 48 hrs before lysis with control vectors lacking inserts (lanes 1, 3, and 7) or containing the indicated cDNAs (top, panel A). The positions of marker proteins are shown at the left and positions of ARF-p19 or InK4a-p16 at the right and by arrowheads in panels A and B. Blots were developed using enhanced fluorography (exposure time, 3 secs), allowing only approximate comparisons of signal intensities between the different panels.

FIG. 5 (panels A–C) shows the localization of ARF-p19 and p19-hemagglutinin fusion proteins to cellular nuclei. Cytospin preparations of NIH-3T3 cells infected for 48 hrs with a vector encoding HA-tagged ARF-p19 were fixed and stained with antiserum to ARF-p19 (panel A), anti-ARF-p19 plus cognate peptide (panel B), or anti-HA serum (panel C). Matched exposures are shown at 600X magnification. The addition of polypeptides having ARF-p19 sequences blocks the signal produced by the antibodies specific for ARF-p19 (panel B).

FIG. 6 summarizes mutant amino acid residues in ARF-p19 predicted from mutations in the gene that encodes both p16-InK4a and ARF-p19 compiled from data from primary tumors, xenografts, and established cell lines. The majority of INK4A mutations so far described target the 5' portion of INK4A exon 2 (Hirama and Koeffler, *Blood* 86:841–854 (1995)), which encodes portions of both InK4a-p16 and ARF-p19. Comparison of the mouse (upper) and human (lower) ARF-p19 amino acid sequences defines conserved residues (bold type). Residues in the human gene that have sustained mutations in cancer cells are doubly underlined and the mutant amino acids are indicated below them. Mutations that are silent with regard to the InK4a-p16 coding frame but which are predicted to affect the primary structure of ARF-p19 are indicated by asterisks (e.g., P71T*). Superscripts note multiple substitutions of the same residue (e.g. G68L$^3$ was independently observed in 3 cases), and closed squares define microdeletions plus frame shifts. No nonsense mutations were found. All mutations were detected in sporadic cancers except for R114L (G101W in p16), which has been genetically implicated in familial melanoma in 3 of 9 kindreds (Hussussian et al., *Nature Genet* 8:15–21 (1994); Kamb et al., *Nature Genet* 8:22–26 (1994b)). Known sequence polymorphisms have been excluded, The remaining data were taken from Caldas et al., *Nature Genet* 8:27–32 (1994), Hayashi et al., *Biochem. Biophys. Res Commun.* 202:1426–1430 (1994), Kamb, A. et al., *Science* 264:436–440 (1994), Mori et al., *Cancer Res.* 54:3396–3397 (1994), Ohta et al., *Cancer Res* 54:5269–5272 (1994), and Zhang et al., *Cancer Res* 54:5050–5053 (1994). Numbering of InK4a-p16 amino acid sequences in the text is based on the corrected N-terminus (Hannon and Beach, *Nature* 371:257–261 (1994)) which includes 8 residues beyond those originally identified (Serrano et al., *Nature* 366:704–707 (1993)).

FIG. 7 shows the sequence of a human cDNA molecule (SEQ ID NO:3; see also Mao et al., *Cancer Research* 55:2995–2997 (1995)) corresponding to human INK4A b transcripts and the sequence of the polypeptide, ARF-p19 (SEQ ID NO:4, denoted "arf" in the Figure), which is (as described herein) encoded thereby. The partial carboxyl-terminal amino acid sequence of human InK4a-p16 ("p16") is also indicated.

Figure 8A:
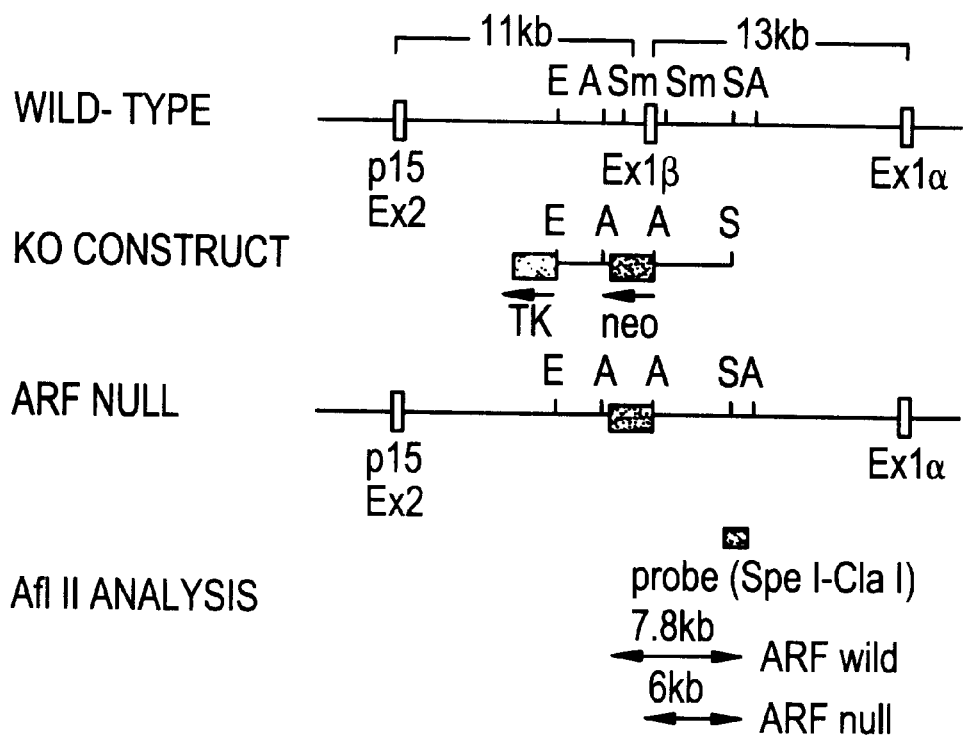

FIGS. 8A–8C shows the loss of p19$^{ARF}$ and expression of p16$^{INK4a}$ mRNA in ARF-null mice. FIG. 8A depicts a schematic representation of the INK4a locus and ARF targeting vector. Open boxes denote exons with the 3' end INK4b to the left and the 5' end of INK4a to the right. AflII sites (FIG. 8A) important for analysis of deletions are indicated, with the predicted sizes of the fragments containing intact exon 1β or neo noted below. FIG. 8B shows the Southern blot analysis of tail DNA from F2 animals with ARF genotype noted. The sizes of the AflII fragments predicted in panel A are indicated. FIG. 8C shows the RT-PCR amplification of RNA from the testis (lanes 2 and 4) and liver (lanes 3 and 5) of ARF(+/+) (lanes 2 and 3) and (−/−) (lanes 4 and 5) mice. Lane 1 shows results with no templates, and lane 6 shows products recovered from equal amounts of MEL, cell RNA used as a positive control. Amplification of hypoxanthyl phosphoribosyl transferase mRNA (HPRT) was used to demonstrate integrity of templates from all samples.

FIGS. 9A–9B shows the expression of p16$^{INK4a}$ in MEFs. FIG. 9A shows MEFs from six embryo strains were assayed at indicated passage numbers for p16$^{INK4a}$ expression by sequential precipitation and immunoblotting with antiserum to the mouse p16 C-terminus. Top and bottom panels were taken from parallel gels, shown with matched exposures. All precipitations were performed using an excess of titered antibody with equal protein inputs per sample. FIG. 9B shows p16 immunoprecipitates as in FIG. 9A were separated on gels and blotted with antiserum directed to CDK4. Because p16 levels are relatively low in ARF(+/+) cells but increase as cells are passaged, results for coprecipitating CDK4 are shown with strains 3–9 and 3–10 at passage 11. Exposures in FIGS. 9A and 9B are matched.

Figure 10A:
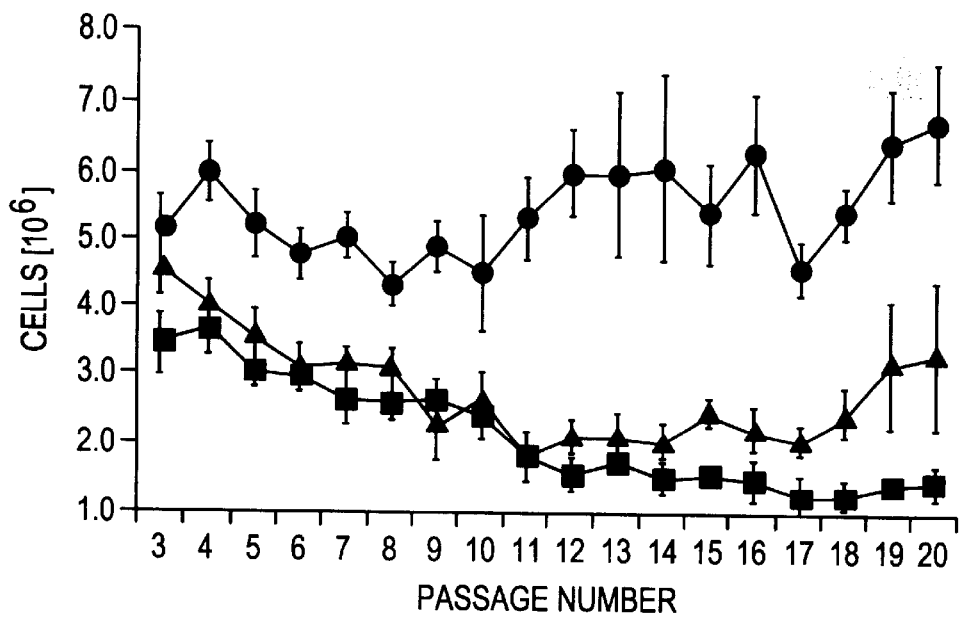
Figure 10B:
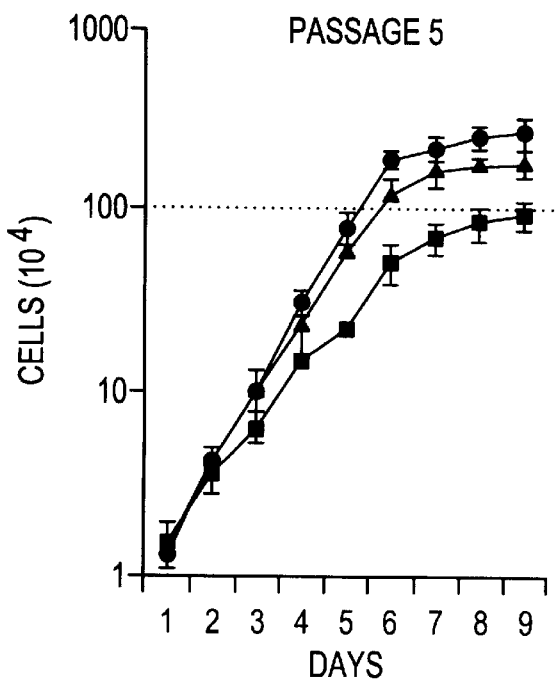
Figure 10C:
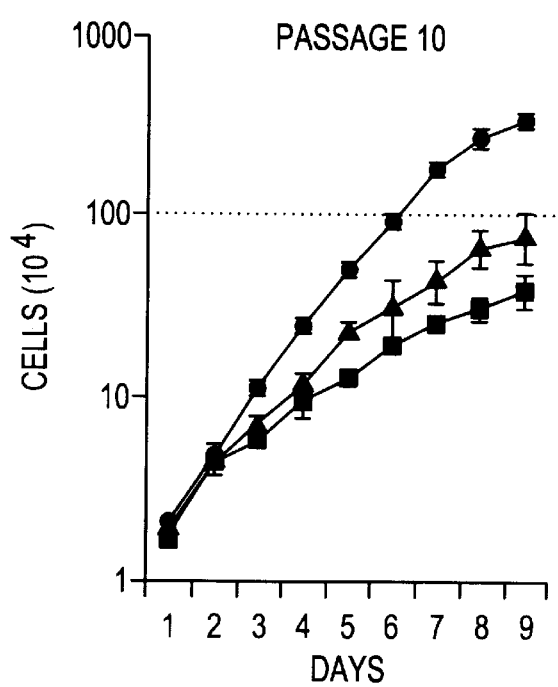
Figure 10D:
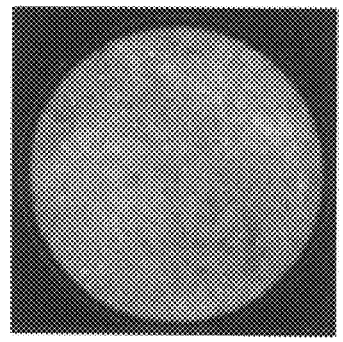
Figure 10E:
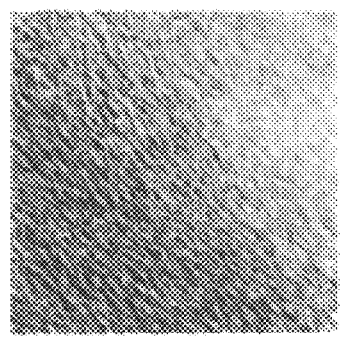
Figure 10F:
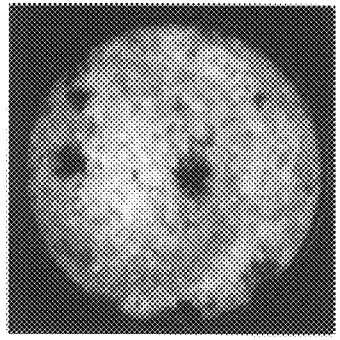
Figure 10G:
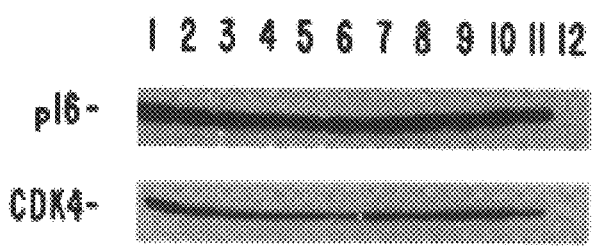

FIGS. 10A–10G show the kinetics of MEF growth and ras transformation. FIG. 10A shows cell proliferation on a 3T9 protocol. At 3 day intervals, the total numbers of cells per culture (ordinate) were determined prior to re-dilution of the cells to 9×10$^5$ per 60 mm diameter dish for re-passage. Data were pooled from 6–8 embryos of each genotype (total MEF strains=20): ARF(−/−), (circles); ARF(+/−), (triangles); ARF (+/+), (squares). Bars indicate standard errors from the mean. FIG. 10B shows cells from 3 ARF(−/−) (circles), 3 ARF(+/−) (triangles), and 3 ARF(+/+) (squares) MEF strains at passages 5 or 10 were seeded at 2×10$^4$ per culture in 20 replicate 60 mm, diameter dishes. Duplicate dishes were harvested at daily intervals, and the total numbers of cells per culture (log scale ordinate) was determined. Data from different strains of the same genotype were pooled. Error bars indicate standard deviations (2σ) from the mean. FIG. 10C shows the MEF monolayer from ARF(−/−) cells transformed by ras versus a control plate transfected with the naked vector (FIG. 10A). Macroscopic foci of transformed cells (FIGS. 10B and C) are heavily stained with Giemsa. In FIGS. 10D–G, lysates from 11 independently expanded foci (lanes 1–11) were precipitated with anti-p16$^{INK4a}$, transferred to nitrocellulose after electrophoresis on denaturing gels, and probed with the same antibody (top) or with antiserum to CDK4 (bottom) as indicated in the left margin. Lane 12 shows results with NIH-3T3 cells that lack the INK4a locus. Exposures are matched.

Figure 11A:
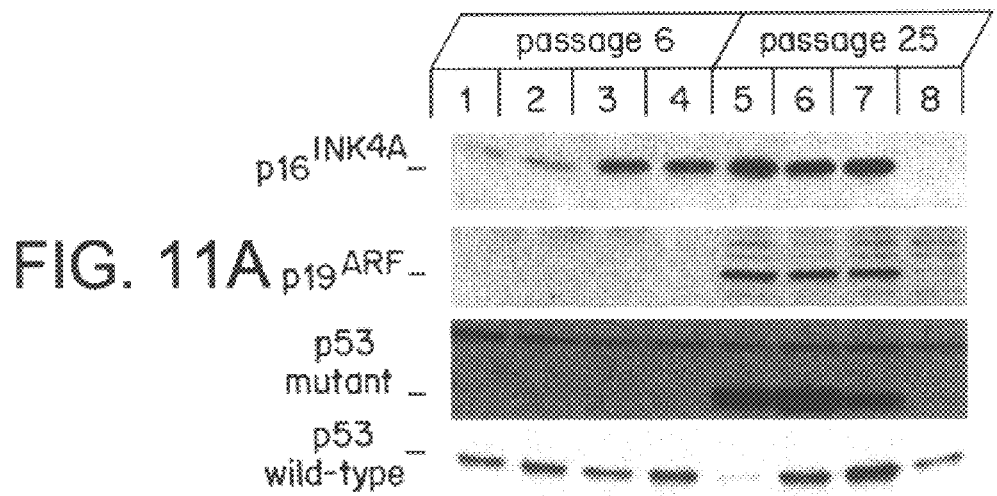
Figure 11B:
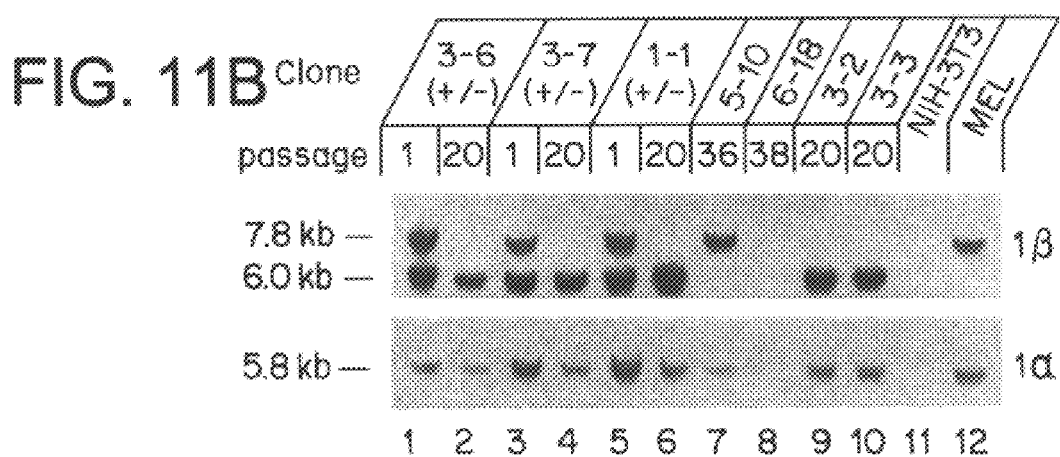
Figure 11C:
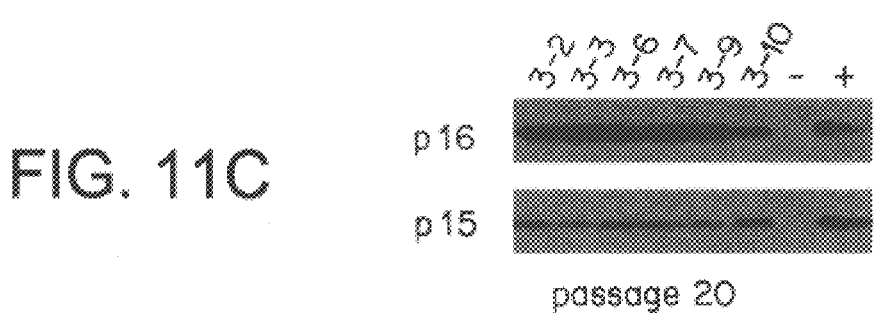

FIGS. 11A–11C show the expression of p16$^{INK4a}$, p19$^{ARF}$, and p53 in MEF stratins and established lines derived from them. FIG. 11A shows the expression of p16$^{INK4a}$ and p19$^{ARF}$ as documented by immunoprecipitation and immunoblotting as performed in FIG 9. The same cells were metabolically labeled with [$^{35}$S]-methionine and precipitated with monoclonal antibodies to wild-type or mutant p53 as indicated. Wild-type MEFs included clones 5–9 (lanes 1 and 5), 5–10 (lanes 2 and 6), 6–14 (lanes 3 and 7), and 6–18 (lanes 4 and 8). FIG. 11B shows the Southern blot analysis of ARF exon 1β and INK4a exon 1α sequences. DNAs digested with AFlII (top) or EcoRI (bottom) were hybridized with exon 1β genomic or exon 1α cDNA probes, respectively. Positions of diagnostic fragments containing (7.8 kh) or lacking (6.0 kh) exon 1β indicated to at the left of the top panel. Clones 3–6, 3–7, and 1–1 (lanes 1–6) were derived from mice hemizygous for ARF exon 1β. Clone 6–18 (lane 8) and NIH-3T3 cells (lane 11) originated from wild-type MEFs that sustained bi-allelic deletions of the entire INK4a locus, including intron sequences recognized by the probe. Clones 3–2 and 3–3 (lanes 9 and 10) were established from ARF-null animals that retained p16$^{INK4a}$ coding sequences (FIG. 9A). MEL cells (lane 12) do not express p53, and late passage clone 5–10 MEFs (lane 7) express a mutant form of the protein (FIG. 12). FIG. 11C shows MEFs at passage 20 that were scored for INK4 protein expression by immunoblotting. Lysates from clone 6–18 and 5–10 cells were used as negative (−) and positive (+) controls.

Figure 12A:
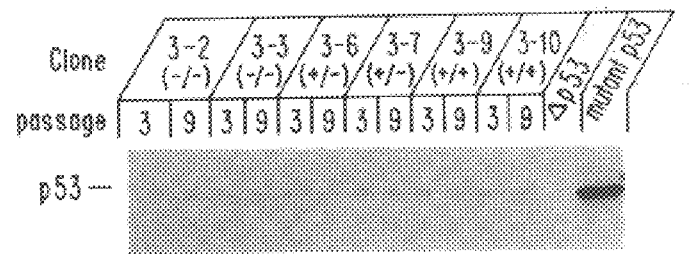
Figure 12B:
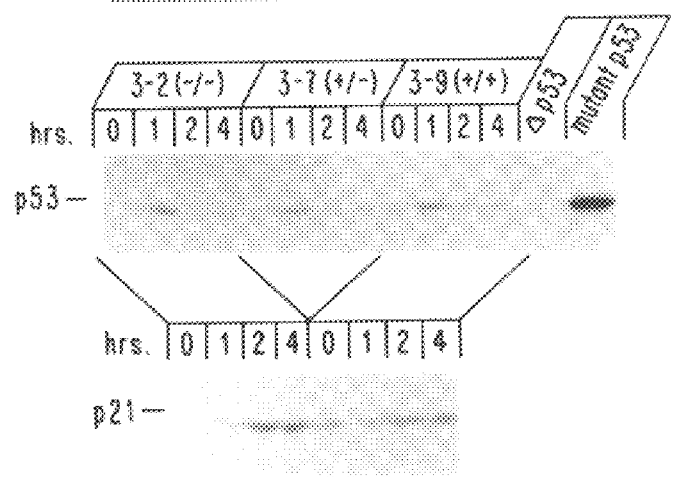
Figure 12C:
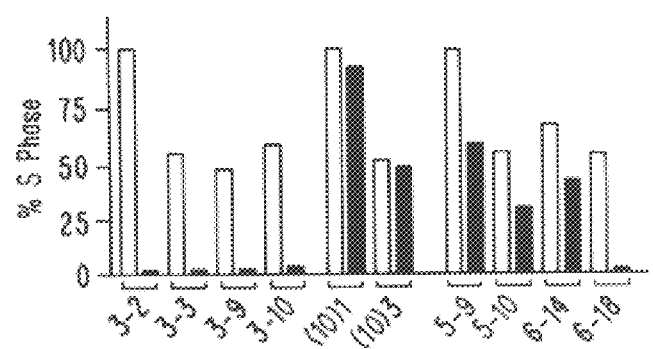
Figure 12D:
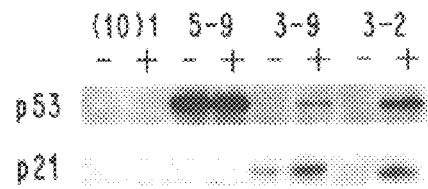

FIGS. 12A–12D ARF and p53 interactions in MEFs. FIG. 12A depicts lysates from MEFs with different ARF genotypes that were analyzed for p53 status by immunoblotting with an antibody that recognizes both wild-type and mutant p53. No mutant p53 was detected by precipitation with PAb240, whereas the wild-type form was again detected with PAb246. FIG. 12B shows cells with the indicated ARF genotype that were irradiated with 5 Gy, and p53 and p21 that were measured by immunoblotting at the indicated times (hr) after exposure. Lysates of clone 5–10 cells were used to document higher levels of mutant p53 expression on a per protein basis. Balb-3T3 (10)1 cells null for p53 (Δp53) were used as a negative control. FIG. 12C shows MEF strains (clones 3–2, 3–3, 3–9, and 3–10 at passage 12), established MEF cell lines (clones 5–9, 5–10, 6–14, and 6–18 at passage 26), and Balb-3T3 derivatives lacking p53 that were infected with an ARF-retrovirus (filled bars) or with the naked control vector (open bars). Cells were labeled for 24 hr with [$^3$H]thymidine 48 hrs post-infection. Results with MEF strains, Balb-3T3 derivatives, and established MEF lines were normalized to values (set to 100%) obtained with 3–2, 10–1, and 5–9 cells, respectively, infected with the control vector. Standard deviations were less than ±10% of the mean. FIG. 12D shows cells that were infected with ARF-retrovirus (+) or with vector alone (−) and were lysed 24 hours post-infection. Gel separated proteins were immunoblotted for p53 and p21.

Figure 13A:
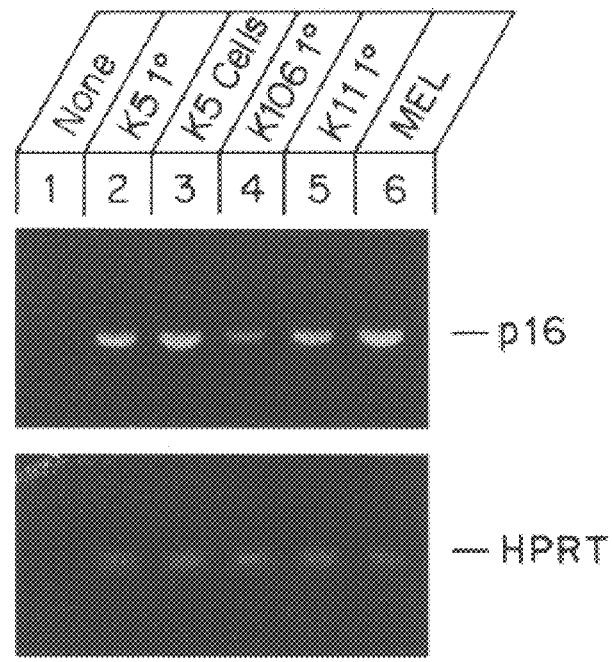
Figure 13B:
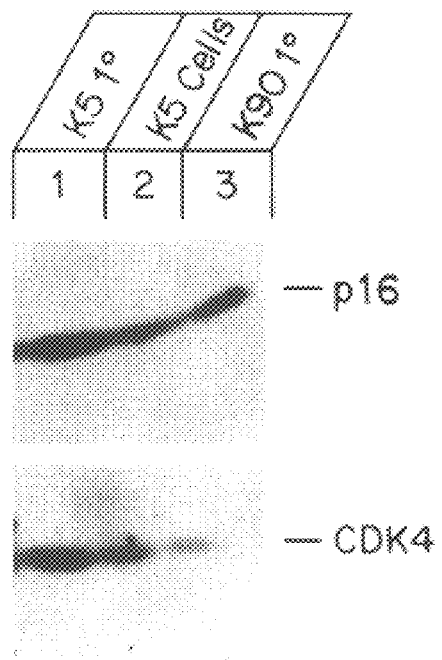

FIGS. 13A–13B shows the expression of p16$^{INK4a}$ in mouse tumors. FIG. 13A shows RT-PCR analysis of tumor tissue. Total mRNAs extracted directly from the K5 fibrosarcoma (1°), a cell line established from it (K5 cells), and directly from the K11 lymphoma (1°) were amplified using p16 and HPRT primers as in FIG. 8C. Lanes 1 and 6 show results with no template and MEL cell mRNA, respectively. FIG. 13B shows cell lysates (800 μg protein pet lane) from the K5 and K90 primary tumors (1°) and from the established K5 cell line that were precipitated with antibodies to the p16$^{INK4a}$ C-terminus, and proteins were separated on denaturing gels and blotted with the same antibody (top) or with rabbit antiserum to CDK4 (bottom).

Figure 14A:
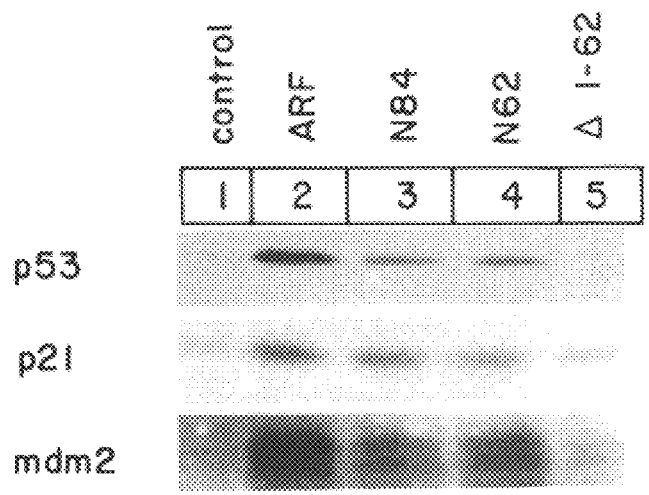
Figure 14B:
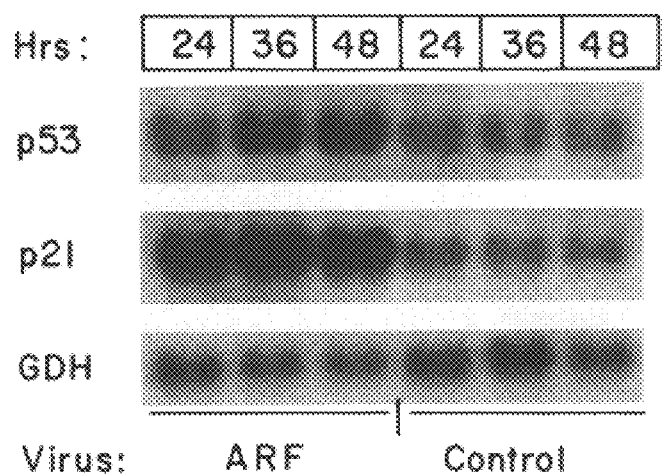
Figure 14C:
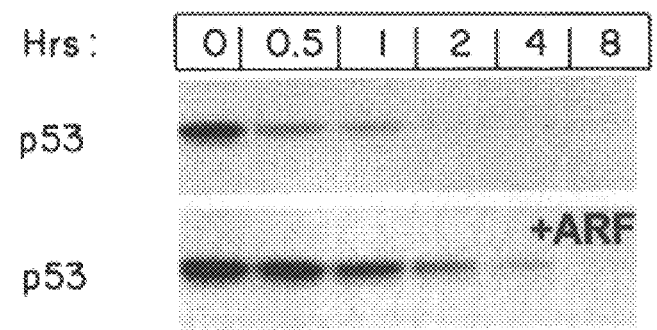

FIGS. 14A–14C shows that ARF-stabilizes p53 and induces p53-dependent gene expression. FIG. 14A shows MEFs that were lysed 48 hrs after infection with retroviruses encoding either p19$^{ARF}$, C-terminally truncated p19$^{ARF}$ mutants (N84, N62), or an N-terminally truncated ARF mutant (Δ1–62). Proteins were detected by direct immunoblotting using antibodies to p53, p21$^{Cip1}$, and mdm2 as indicated in the left margin. FIG. 14B shows Northern blot analysis of RNA extracted from MEFs that were infected for the indicated times with p19$^{ARF}$ or control retrovirus vectors. Uninfected proliferating cells express levels of p53, p21$^{Cip1}$, and glyceraldehyde 3-phosphate dehydrogenase (CDH) RNAs equal to those detected in cells infected with the control vector. FIG. 14C shows ARF-null MEFs that were pulsed for 1 hr with [$^{35}$S]- methionine and chased in medium containing excess unlabeled precursor following a 36 hour infection with either a control (top) or p19$^{ARF}$ retrovirus (bottom). Precipitated p53 from cells lysed at the indicated times after labeling was resolved on denaturing gels.

Figure 15A:
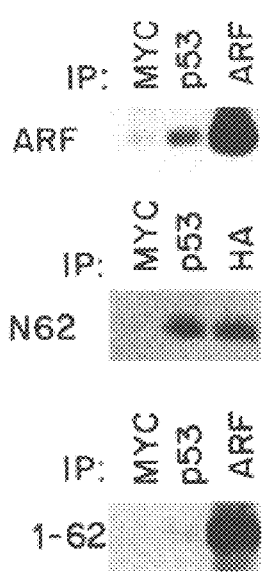
Figure 15B:
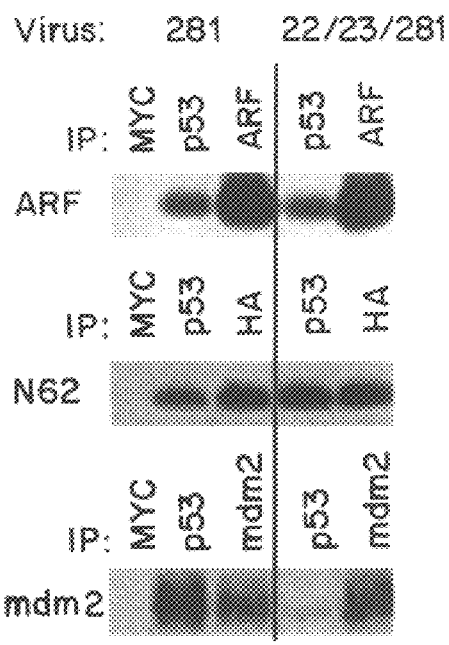
Figure 15C:
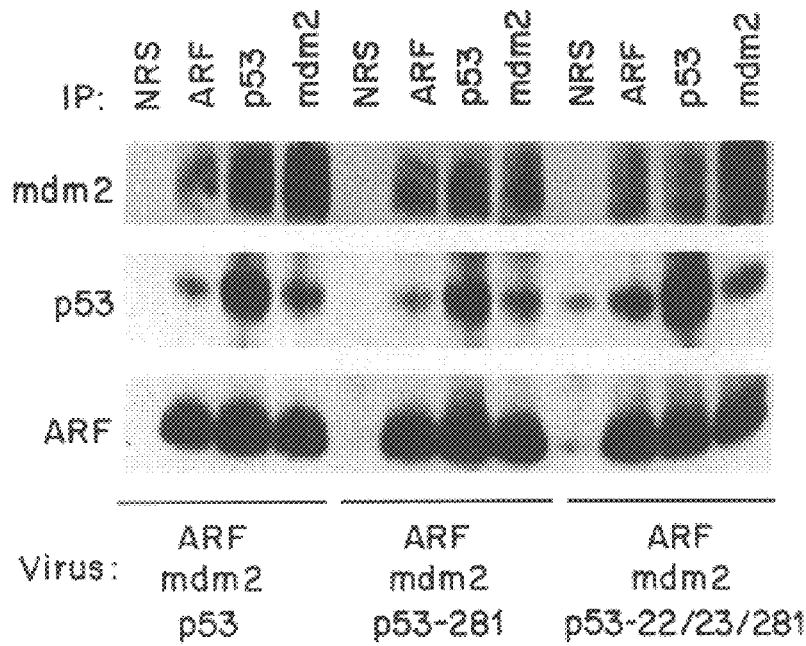

FIGS. 15A–15C shows that functional p19$^{ARF}$ binds to both mdm2 and p53 and can form ternary complexes. FIG. 15A depicts Sf9 cells that were co-infected for 48 hrs with baculoviruses encoding wild-type p53 and either p19$^{ARF}$ or the indicated p19$^{ARF}$ mutants that were lysed and precipitated with control antibody to myc (9E10), p53 (PAb 421), affinity-purified antibody to the ARF C-terminus, or anti-HA (to detect HA-tagged N62). Proteins in immune complexes separated on denaturing gels were transferred to filters and detected by immunoblotting with anti-ARF or anti-HA (for N62). FIG. 15B depicts similar experiments to those shown in FIG. 15A which were performed using the indicated p53 mutants (top 2 panels). Sf9 cells were also co-infected with the indicated p53 mutants and mdm2 (lower panel) to document the inability of the 22/23/281 mutant to bind mdm2. Proteins precipitated with PAb421 or antibody 2A10 to mdm2 were electrophoretically resolved, transferred and blotted with 2A10. FIG. 15C depicts Sf9 cells that were infected with the viruses indicated below each panel and were lysed and incubated with nonimmune serum (NRS), antibodies to the ARF C-terminus, PAb421 (p53), or antibody 2A10 (mdm2) as indicated at the top of each lane. Resolved proteins were blotted with antibodies to mdm2 (top), p53 (middle) or ARF (bottom) as above.

Figure 16A:
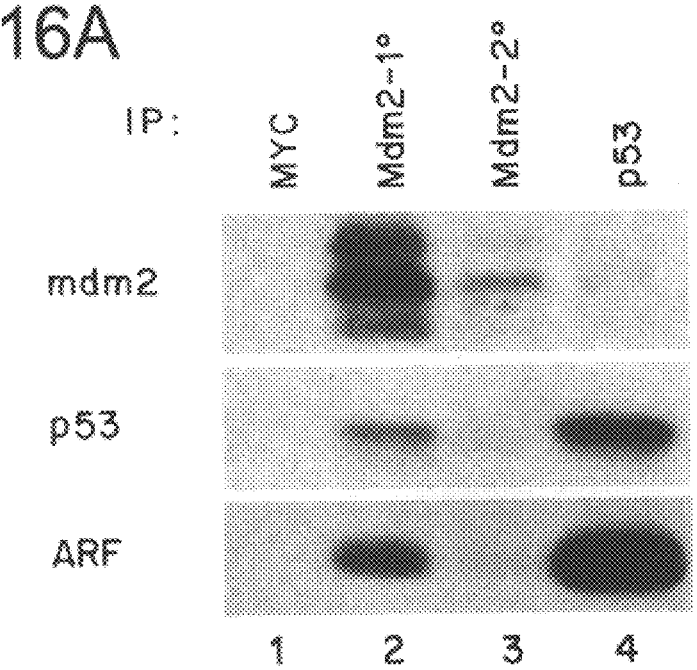
Figure 16B:
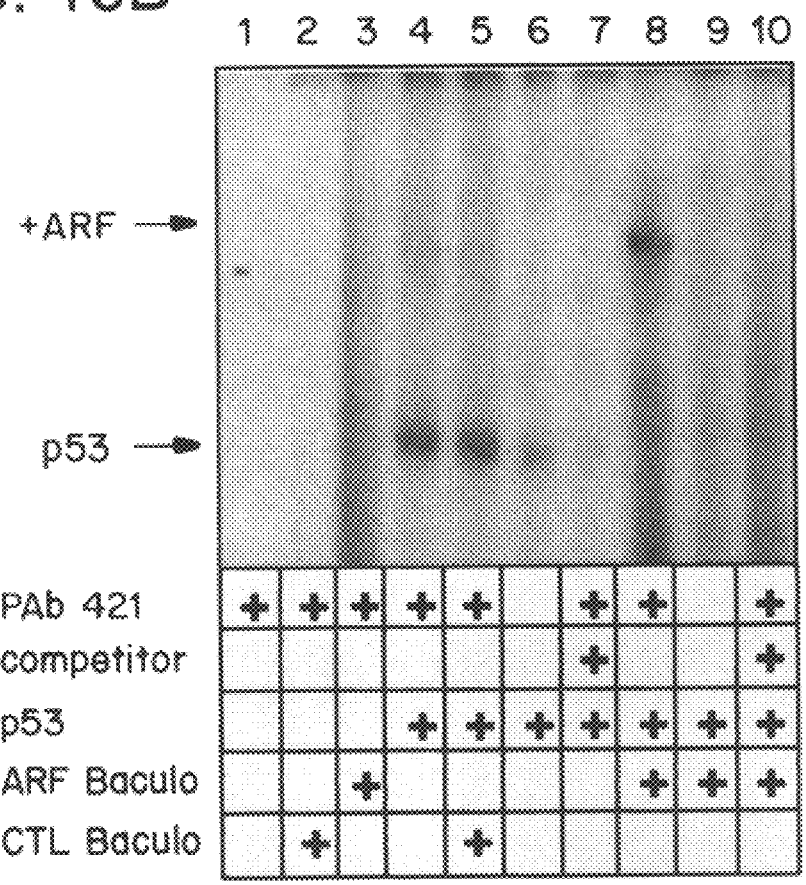

FIGS. 16–16B show the direct interactions of p19$^{ARF}$ and p53. FIG. 16A shows the sequential precipitations [(IP), lanes 1 through 4] of lysates from NIH-3T3 cells infected with ARF virus which were performed with the indicated antibodies. Precipitated proteins were separated and blotted with antibodies to mdm2, p53, and ARF. FIG. 16B shows EMSA that was performed with an end-labeled oligonucleotide containing two consensus p53 binding sites [Friedlander et al., J. Biol. Chem., 271:25468–25478 (1996)]. Additions to the binding reactions are indicated below the lanes and included activating antibody PAb-421, ten-fold excess cold unlabeled oligonucleotide (competitor), purified recombinant p53, and Sf9 extracts from cells infected with baculovirus vectors encoding ARF or no recombinant protein (CTL). Arrows indicate positions of the p53-oligonucleotide complex and of that supershifted by ARF.

Figure 17:
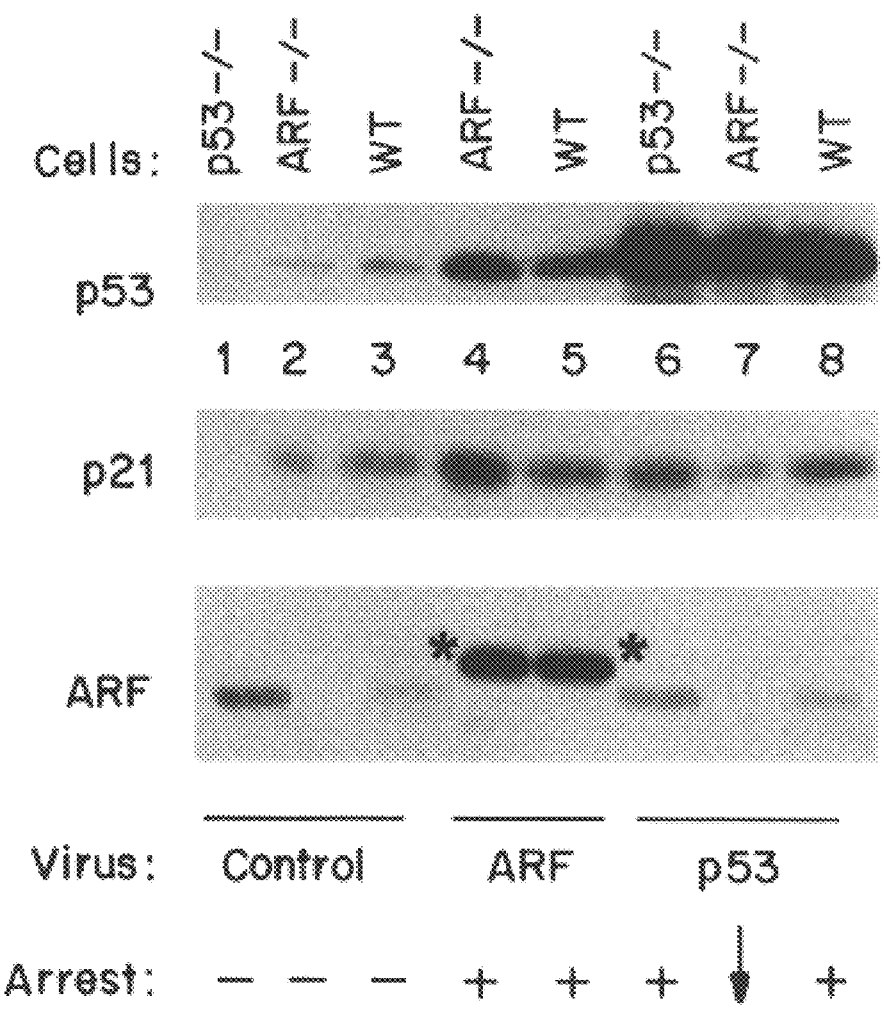

FIG. 17 shows the inductio of p21 $^{Cip1}$ by ARF or p53 retroviral vectors. Cells infected with vector alone (lanes 1–3), a retrovirus encoding HA-tagged p19$^{ARF}$ (lanes 4 and 5), or a vector encoding wild-type p53 (lanes 6–8) that were lysed 48 hrs after infection. Proteins separated on gels were immunoblotted for p53 (top), p21$^{Cip1}$ (middle) and p19$^{ARF}$ (bottom) as indicated at the left. Infected cells included p53-null early passage MEFs (lanes 1 and 6), wild-type MEFs (lanes 3, 5. and 8), or early passage ARF-null MEFs (lanes 2, 4, and 7). Endogenous p19$^{ARF}$, elevated in p53-null cells (lane 1), is repressed after infection with p53 virus (lane 6). HA-tagged ARF (indicated by asterisks) migrates slower than the endogenous protein. Growth arrest was assayed at 48 hrs by incorporation of [$^3$H]-thymidine in replica plates.

Figure 18A:
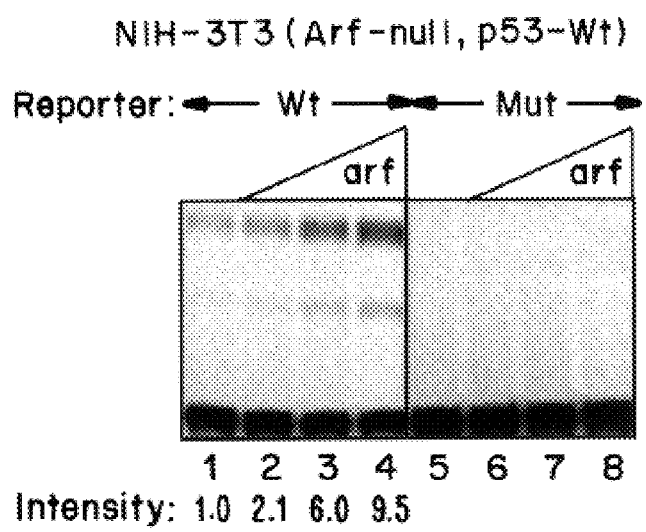
Figure 18B:
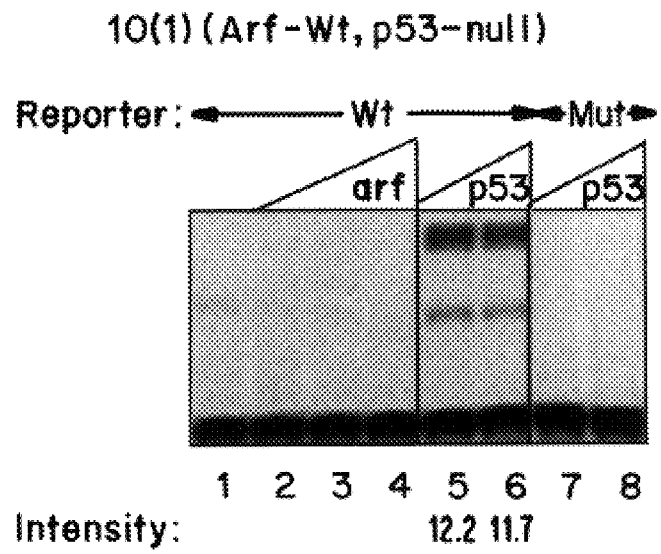
Figure 18C:
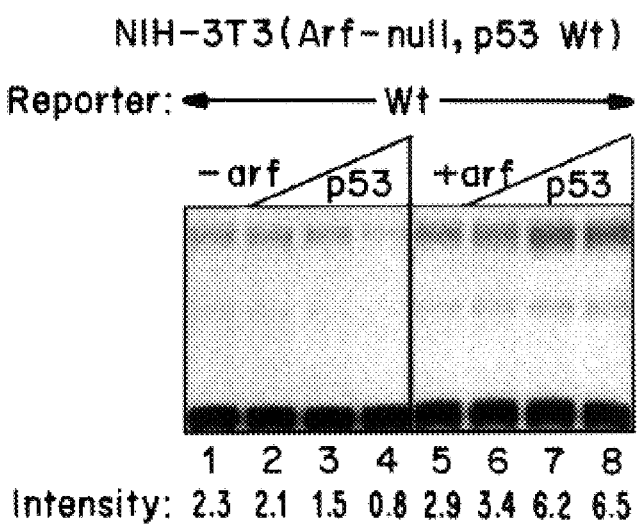

FIGS. 18A–18C shows the transactivation by ARF and p53. NIH-3T3 or 10 (1) fibroblasts were transiently transfected with wild-type PG13-CAT (WT) or mutant MG15-CAT (Mut) and increasing amounts p19$^{ARF}$ or p53. In FIGS. 18A and 18B, the ARF plasmid inputs in lanes 2–4 and 6–8 were 1, 2, and 5 μg DNA, whereas only 10 and 100 ng of p53 plasmid were used in FIG. 18H (lanes 5–8). Tn FIG. 18C, cells received no ARF DNA (lanes 1–4) or 1 μg ARF plasmid (lanes 5–8) plus 1, 2, or 5 μg p53 plasmid (lanes 2–4 and 6–8, respectively). Cell lysates prepared 48 hours after transfection were analyzed for CAT activity. The mono-and diacetylated species are at the middle and top of the plate, respectively. Signal intensities for diacetylated forms computed by densitometry and indicated below the lanes were normalized to 1.0 (FIG. 18A, lane 1).

FIG. 19 shows the expression of p19$^{ARF}$ in early-passage, primary MEF strains. MEFs of the indicated genotypes (left) propagated on a 3T9 protocol were harvested at passage numbers given at the top of panel, lysed and immunoblotted for p19$^{ARF}$ protein expression. Equal quantities of protein (200 μg) were loaded per lane.

Figure 20A:
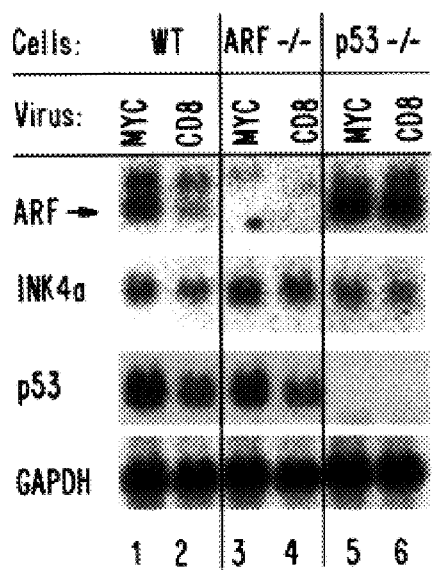
Figure 20B:
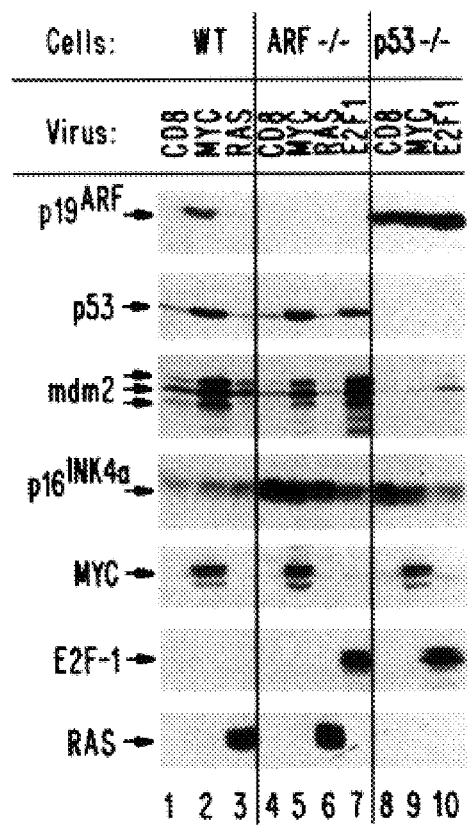

FIGS. 20–20B show the expression of ARF, p53, and p53 targets in virus-infected MEFs. FIG. 20A shows wild-type (WT), ARF-null, or p53-null MEFs (indicated at top) which were infected with either a control (CD8) or MYC-expressing retrovirus. 48 hours post-infection, total RNA was isolated from infected cells, electrophoretically separated, blotted to filters and hybridized sequentially with specific [$^{32}$P]-labeled probes specific for ARF (exon 1β), INK4a (exon 1α), p53, and glyceraldehyde 3-phosphate dehydrogenase (GAPDH). FIG. 20B shows replicate cultures infected with CD8 or MYC viruses, or infected with RAS or E2F-1 vectors (indicated at the top on the panel) which were lysed 48 hours post-infection and immunoblotted using antibodies directed to the proteins indicated in the left margin. Wild-type cells infected with the E2F-1 virus died and could not be analyzed (see text). Because a smaller fraction of cells from other MYC-infected and E2F-1 infected cultures underwent apoptosis, equal quantities of protein were loaded per lane to provide valid comparisons.

Figure 21:
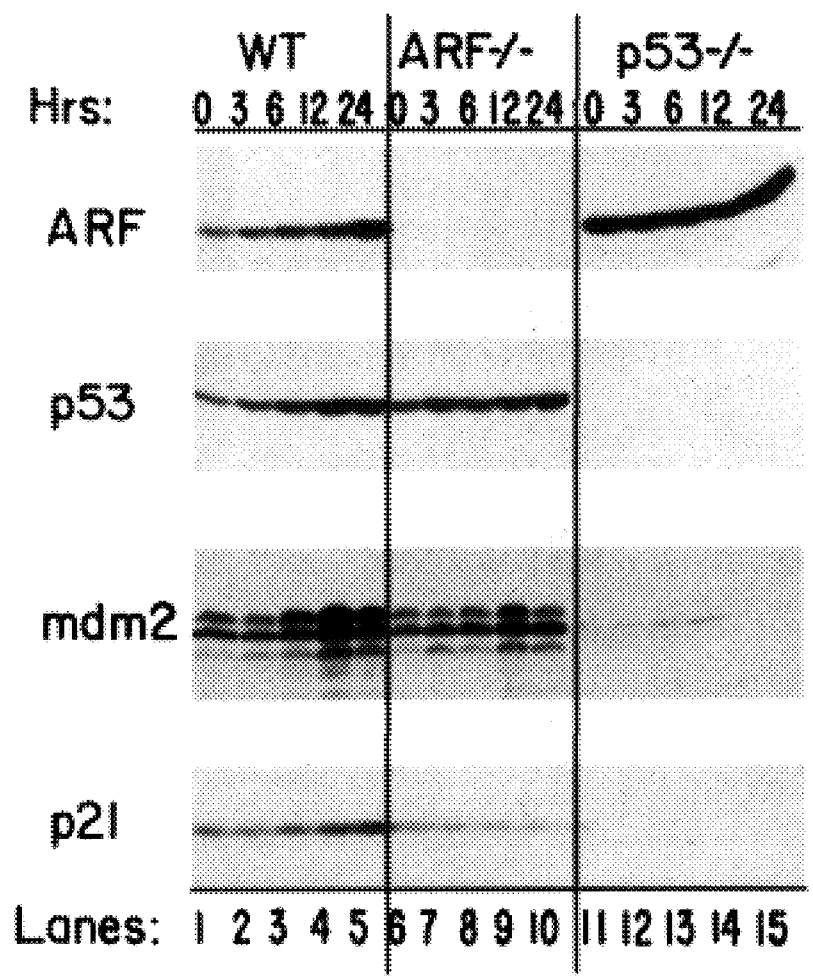

FIG. 21 shows induction of ARF, p53, mdm2, and p21$^{Cip1}$ by MYC-ER™. MEFs of the indicated genotypes (top) infected with a MYC-ER™ virus were treated with 4-hydroxytamoxifen for the indicated intervals (hrs), and cell lysates were immunoblotted with antibodies directed to the proteins indicated in the left margin. Levels Of MYC-ER™ expressed in the three cell types were comparable.

Figure 22A:
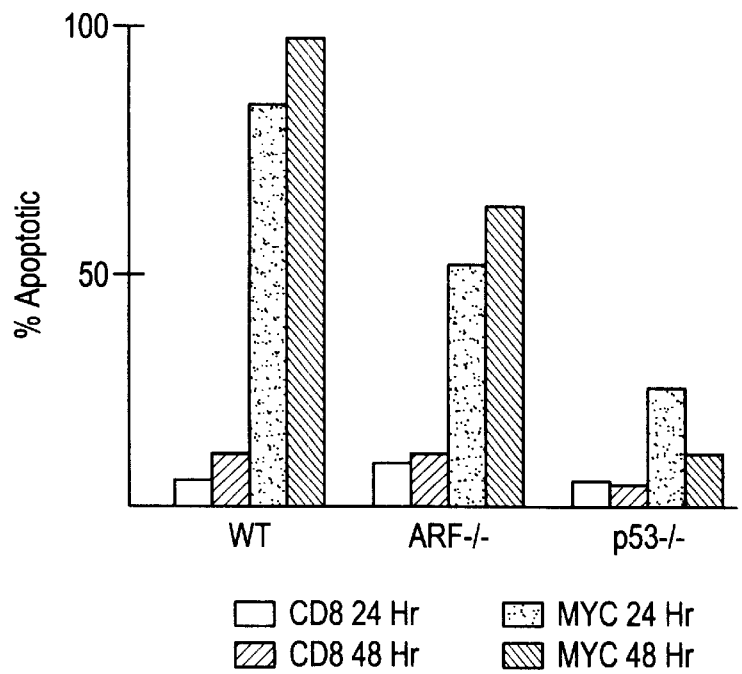
Figure 22B:
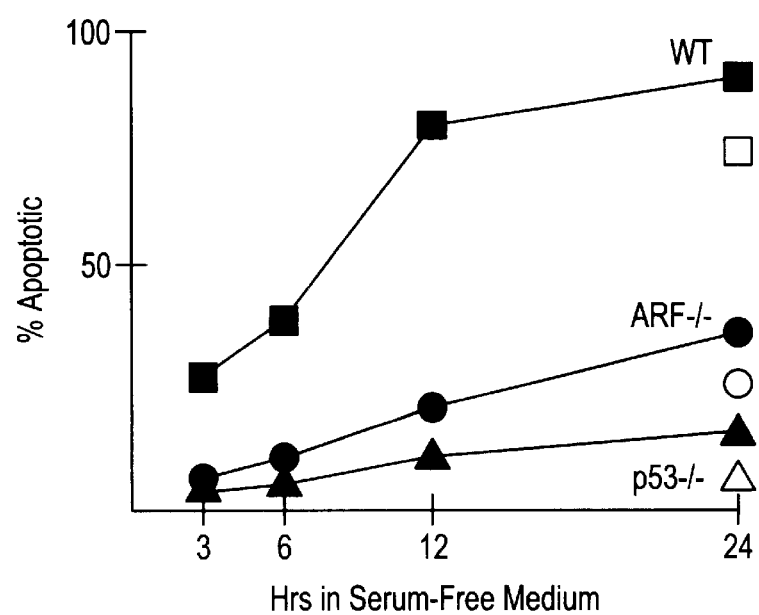

FIGS. 22A–22B shows MYC induced apoptosis. FIG. 22A shows MEFs of the indicated genotypes infected with MYC or CD8 virus for 48 hrs (the same populations as in FIG. 20) were cultured for two more days and then transferred into serum-free medium for an additional 48 hrs. Apoptosis was scored using a propidium iodide-based FACS assay to quantitate cells with subdiploid DNA content 24 and 48 hrs after serum starvation. Viruses and times of infection are indicated by the legend at the upper right of the panel. All standard deviations were within 10% of the means shown. FIG. 22B shows cells of the indicated genotypes infected with MYC-ER™ virus and pretreated with 4-hydroxytamoxifen for 24 hours (the same populations as in FIG. 21) were shifted into serum-free medium (closed symbols), and apoptosis was scored by propidium iodide FACs assay at the indicated times (abscissa). Untreated, viable cells were also shifted into serum-free medium containing 4-hydroxytamoxifen and scored 24 hours later (open symbols).

Figure 23C:
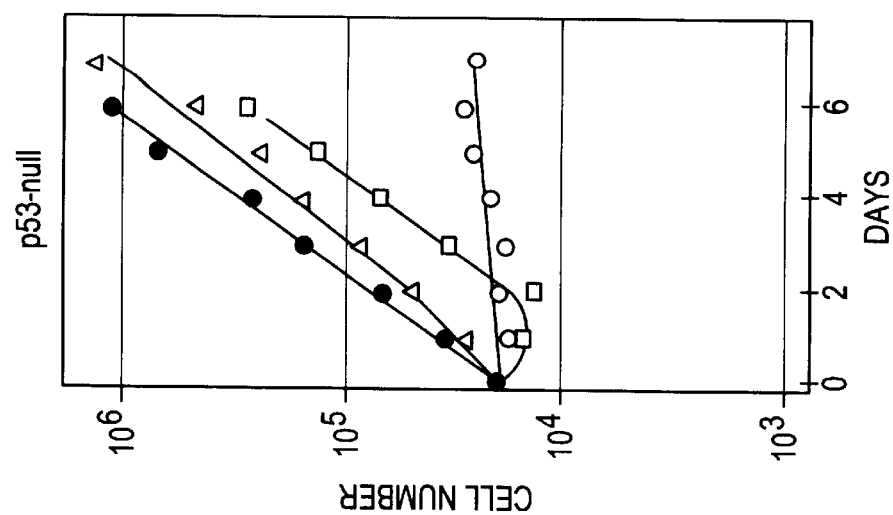
Figure 23B:
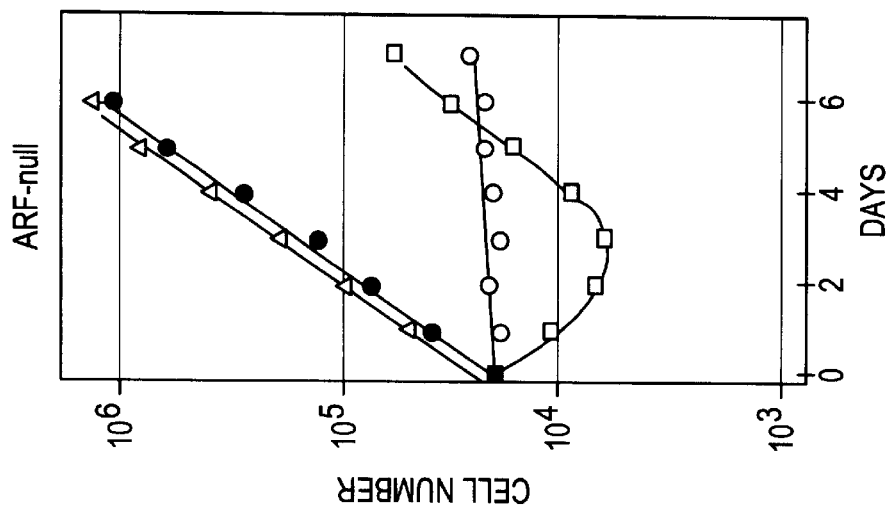
Figure 23A:
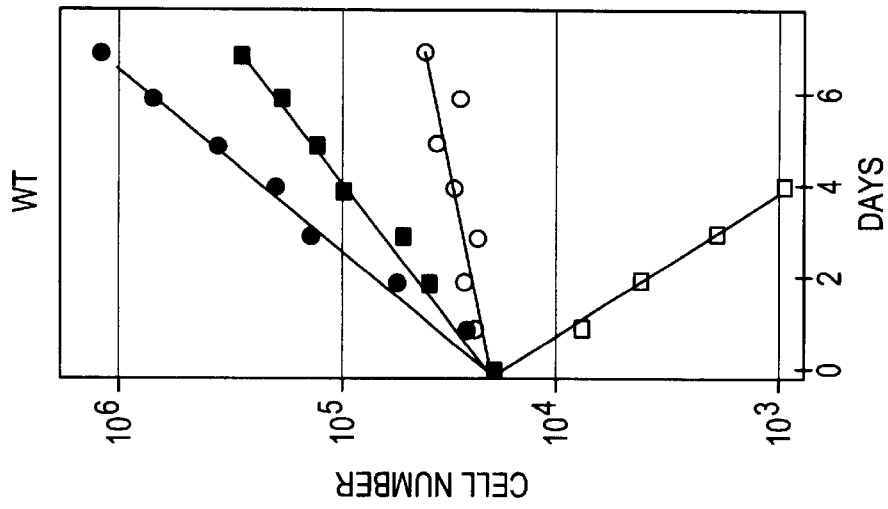

FIGS. 23A–23C show the rates of proliferation of virus-infected MEFs. Wild-type (FIG. 23A), ARF-null (FIG. 23B), and p53-null (FIG. 23C) MEFs infected with control CD8 virus were transferred to serum-containing (closed circles) or defined serum-free (open circles) media 4 days post-infection and counted every day thereafter. Wild-type cells infected with MYC virus grew more slowly in serum-containing medium (FIG. 23A, closed squares) and died in medium lacking serum (FIG. 23A, open squares). A significant number of MYC-infected ARF-null and p53-null cells survived in serum-free conditions (FIGS. 23B and 23C, open squares). When reseeded 14 days post-infection, these MYC-infected cells grew continuously in serum-free medium (FIGS. 23B and 23C, open triangles). All data points represent averages of 6–8 determinations using at least 3 independently derived MEF strains with standard deviations being less than ±25% of the mean (highly significant on log scale).

Figure 24A:
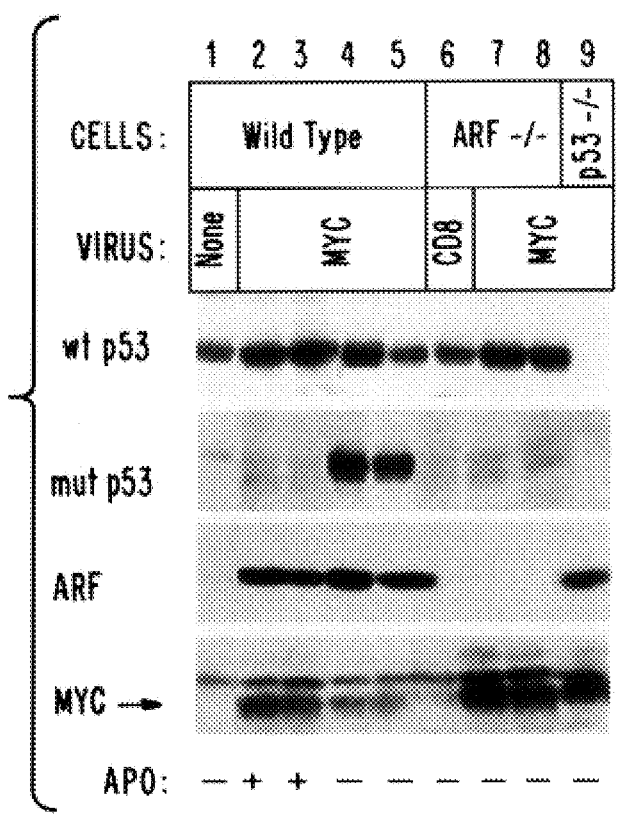
Figure 24B:

FIGS. 24A–24B MYC-"immortalized" MEFs lose p53 or ARF function. FIG. 24A shows MEFs of the indicated genotype were infected with CD8 or MYC retroviruses at passage 5 after explantation and propagated on a 3T9 protocol. Wild-type cells tested 7–10 days after MYC virus infection (lanes 2 and 3) expressed relatively high levels of p19$^{ARF}$ and wild-type (wt) p53, and were initially sensitive to apoptosis (APO +) when transferred into serum-free medium (see text). However, by 14–21 days post-infection, rapidly growing derivatives were isolated that could grow under serum-free conditions (APO −) and expressed mutant (mut) p53 (lanes 4 and 5). ARF-null cells infected at passage 5 and transferred 14 days after selection in serum-free medium were resistant to apoptosis but expressed only wild-type p53 (wt) (lanes 7 and 8). Note that MYC protein levels were significantly higher in ARF-null (lanes 7 and 8) and p53-null (lane 9) cells, than in wild-type MEFs (lanes 2–5). Apoptosis was determined by FACS analysis of propidium iodide- and Hoescht 33342-stained cells. FIG. 24B shows cells containing a single wild-type ARF allele which were infected with MYC virus for 4 days and transferred into serum free medium for 2 days to select for variants resistant to apoptosis. Surviving cells were diluted in microtiter wells and subclones were expanded from single cells in serum-containing medium. Lysates were then blotted for p19$^{ARF}$ and p53. Results with 13 clones (designated A-M) are compared with those obtained with wild-type (wt) uninfected MEFs.

Figure 25:
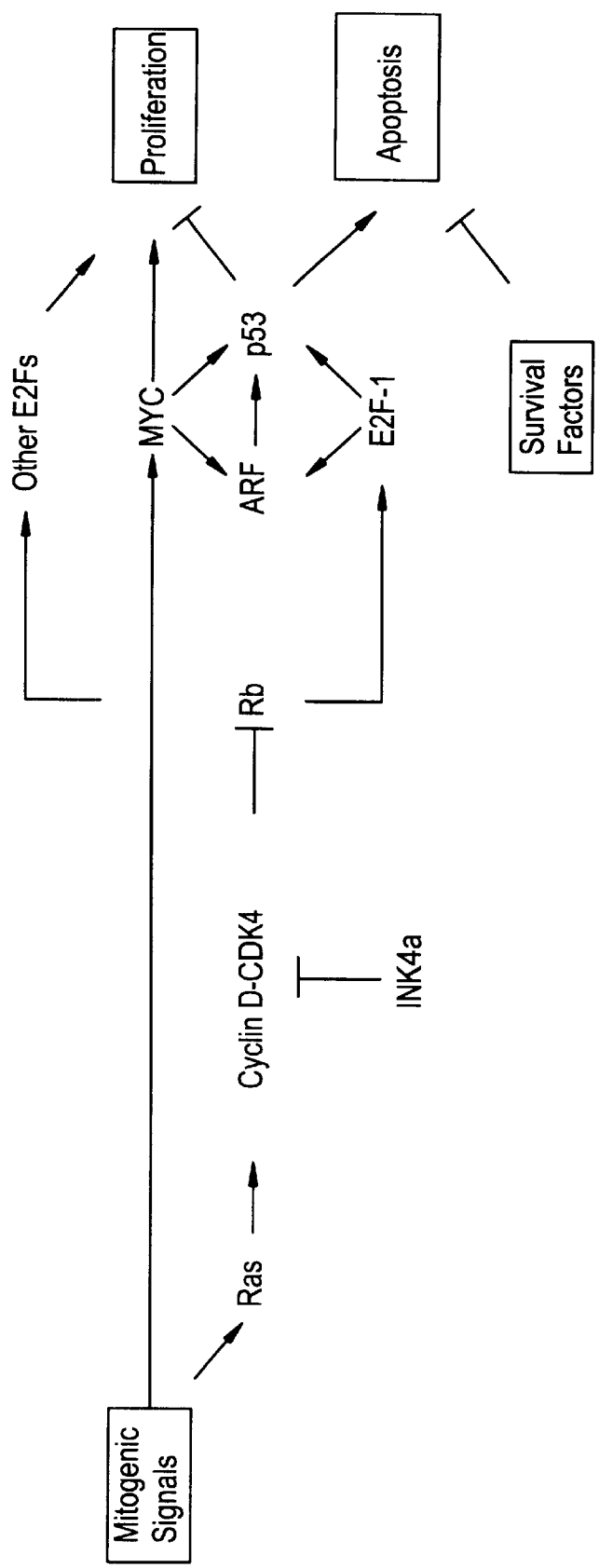

FIG. 25 depicts a model for ARF signaling. ARF is activated via MYC and E2F-1 and acts in turn to trigger p53-dependent cell cycle arrest or apoptosis, depending upon the presence of extracellular survival factors. Ras acts through cyclin D-dependent kinases to stimulate Rb phosphorylation, resulting in release of E2F from Rb constraint and activation of E2F-responsive genes. Activation of ARF by MYC and E2F-1 need not be direct, although both transcription factors have been demonstrated to increase ARF mRNA levels (see text). Like MYC, different E2F isoforms are proposed to regulate both cell growth and cell death. In inhibiting cyclin D-dependent kinases, p16$^{INK4a}$ can modulate certain growth promoting functions of Ras. Other functions of MYC and Ras are not detailed in the schematic.

DETAILED DESCRIPTION OF THE DISCLOSURE

Terms and Symbols

For purposes of this disclosure, the following abbreviations and definitions are used herein unless otherwise indicated.

The following list indicates the correspondence between the one-letter amino acid code (used e.g. in FIGS. 1, 6 and 7 and Example 6) and the three-letter amino acid code (used elsewhere herein, in accordance with 37 C.F.R. § 1.822, revised as of Jul. 1, 1994):

| | | | | |
|---|---|---|---|---|
| A = Ala | C = Cys | D = Asp | E = Glu | F = Phe |
| G = Gly | H = His | I = Ile | K = Lys | L = Leu |
| M = Met | N = Asn | P = Pro | Q = Gln | R = Arg |
| S = Ser | T = Thr | V = Val | W = Trp | Y = Tyr |

| ABBREVIATIONS | | |
|---|---|---|
| CDK | = | cyclin-dependent kinase (protein); cdk = gene |
| cDNA | = | complementary deoxyribonucleic acid |
| DNA | = | deoxyribonucleic acid |
| DMEM | = | Dulbecco's modified Eagle's medium |
| EDTA | = | ethylenediamine tetraacetic acid |
| ES | = | embryonic stem |
| FISH | = | fluorescent in situ hybridization |

| | | |
|---|---|---|
| InK | = | inhibitor of DCK (protein);<br>INK = gene |
| kb | = | kilobase(s) |
| kDa | = | kilodalton(s) |
| MEL | = | mouse erythroleukemia (cell line) |
| nt | = | nucleotide(s) |
| PBS | = | phosphate-buffered saline |
| PCR | = | polymerase chain reaction |
| pRB | = | retinoblastoma protein |
| RT | = | reverse transcriptase |
| SDS | = | sodium dodecyl sulfate |
| Sf9 | = | *Spodoptera frugiperda* (cell line) |
| Tg | = | transgenic |
| TK | = | thymidine kinase |

Throughout the disclosure, abbreviations for nucleotide residues present in nucleic acid sequences are as described in 37 C.F.R. §1.822, revised as of Jul. 1, 1994.

Glossary

"Active fragment" of an ARF-p19 is a peptide or polypeptide that comprises a fragment of the ARF-p19 and retains at least one physiological activity of the ARF-p19 e.g. by acting as a tumor suppressor and/or having the ability to bind to p53. An example of an active fragment of ARF-p19 is a peptide encoded by exon 1β, e.g. amino acids 1–62 of SEQ ID NO:4.

Amino acid sequences: The sequence of a polypeptide given in the order of from amino terminal (N-terminal), to carboxyl terminal (C-terminal). Synonymous with "polypeptide sequence," "peptide sequence," "protein sequence" or "primary protein sequence."

Animals: (1) Excludes human beings, individually and collectively, in all stages of development, including embryonic and fetal stages, unless otherwise indicated; and (2) includes all other vertebrate animals, including an individual animal in any stage of development, including embryonic and fetal stages. "Non-human animal" has the same meaning as "animal."

Animal model: A non-human animal that faithfully mimics a human disease and in which potential therapeutic compositions or potentially harmful compositions may be evaluated for their effect on the disease.

Antibody: A protein molecule synthesized by a B-cell upon exposure to antigen capable of combining specifically with that antigen. Synonymous with immunoglobulin (Ig).

Antibody, polyclonal: A composition that comprises an assortment of different antibodies that all recognize a particular antigen.

Antibody, monoclonal: A unique, isolated antibody molecule produced by a hybridoma.

Antibody, monospecific: A polyclonal antibody produced in immunological response to a single or few epitopes found in (1) a short, isolated, synthetic antigen or (2) a short, isolated, carrier-bound hapten.

Antigen: A molecule or composition of matter which (1) induces an immune response in an animal, and (2) interacts specifically with antigen-recognizing components of an immune animal's immune system.

Asyntactic: Not having the same arrangement (syntax); "out of register." In particular, note that fusion proteins cannot result from the asyntactic linkage of two (or more) open reading frames.

Carrier: A molecule required in combination with a hapten in order for an immune response to the hapten to occur. That is, a molecule which puts a hapten in a molecular context in which the hapten has enhanced immunogenicity.

Detectable label: A chemical moiety that is coupled to a biomolecule to enable detection of the biomolecule and which may be selected from the group consisting of a radiolabel, an enzyme such as horseradish peroxidase or alkaline phosphatase, streptavidin, biotin, an epitope recognized by an antibody, and equivalents thereof.

Detectably labeled: A state of a biomolecule in which the biomolecule has covalently attached to it a detectable label.

Disease: (1) Excludes pregnancy per se but not autoimmune and other diseases associated with pregnancy; (2) includes any abnormal condition of an organism or part, especially as a consequence of infection, inherent weakness, environmental stress, that impairs normal physiological functioning; and (3) includes cancers and tumors.

DNA sequence: The sequence of contiguous nucleotide bases of a strand of DNA as read from 5' to 3'. Synonymous with "DNA molecule."

Enzyme: Protein that is a catalyst for a specific chemical reaction, often one involving one or more biomolecules as substrates and/or products. Unlike non-biologically derived catalysts, enzymes may recognize a substrate with stereospecificity, i.e., some enzymes are capable of recognizing, and thus catalyzing the chemical reaction of, only one of a pair of L- and D-enantiomers.

Epitope: A part of an antigen that interacts specifically with antigen-recognizing components of an animal's immune system. In a polypeptidic antigen, epitopes may correspond to short sequences of contiguous amino acids; the remainder of the antigen is called the carrier. Synonymous with antigenic determinant.

Expression vector: An artificial DNA sequence, or a naturally-occurring DNA sequence that has been artificially modified, into which foreign or abnormal genes can be inserted and that contains transcription and translation signals that direct the expression of the inserted genes in host cells appropriate for the expression vector, and the DNA of which is replicated, either extra- or intra-chromosomally, in such appropriate host cells.

Expression construct: A construct consisting essentially of an expression vector and one or more foreign or abnormal genes inserted therein in such a manner that the expression vector's transcription and translation signals are operably linked to the inserted gene(s).

Foreign or abnormal: Not endogenous to a healthy, wild-type organism. "Foreign or abnormal genes" designates nucleic acid sequences that are not endogenous to an organism's genome, or originally endogenous nucleic acid sequences that have been rearranged, mutated, or otherwise genetically engineered so as to possess properties (i.e., genomic location regulation of expression, copy number, etc.) not possessed by the endogenous nucleic acid sequences from which they were derived.

Gene: A DNA sequence that consists of a structural gene, e.g., a reading frame that encodes a polypeptide sequence, according to the standard genetic code; and expression elements, e.g., promoters, terminators, enhancers, etc., required for transcription of the structural gene.

Genetically engineered: Subject to human manipulation intended to introduce genetic change.

Hapten: A small molecule which (1) cannot, by itself induce an immune response in an animal, (2) can, in combination to a carrier to which it is bound, induce an immune response in an animal, and (3) interacts specifically with the antigen-recognizing components of an immune animal's immune system.

Host animal: An animal that harbors foreign and/or abnormal genes introduced as a result of (1) invasion of cells of the animal by a naturally occurring or genetically engineered intracellular parasite; or (2) introduction into cells of foreign or abnormal genes by human manipulation.

Immune animal: An animal which has been presented with an immunizing amount of antigen and has generated a humoral and/or cell-mediated immune response thereto.

Mammal: (1) Excludes human beings, individually and collectively, in all stages of development, including embryonic and fetal stages, unless otherwise indicated; and (2) includes all other animals that are members of the vertebrae class Mammalia, including an individual animal in any stage of development, including embryonic and fetal stages, wherein members of the class are distinguished by self-regulating body temperature, hair, and, in the females, milk-producing mammae.

Microorganism: A single-celled organism (e.g., a bacterium) or an intracellular parasite (e.g., a rickettsia or a virus); includes both "live" and "attenuated" microorganisms.

Operably linked: Arranged so as to have a functional relationship; in expression constructs inserted foreign or abnormal genes that are properly positioned with regard to the signals that control transcription and translation so that efficient expression of the inserted genes occurs are said to be operably linked to such signals (and vice-versa).

Polypeptide: A polymer of amino acid residues.

Protein: A biomolecule comprising one or more polypeptides arranged into a functional, three-dimensional form.

Restriction endonuclease: An endonuclease that cleaves DNA at each occurrence therein of a specific recognition sequence. Synonymous with "restriction enzyme."

Syntactic: Having the same arrangement (syntax); "in register." In particular, note that fusion proteins can result from the syntactic linkage of two (or more) open reading frames.

Transgene: A gene that does not occur naturally in an animal, i.e., a foreign or abnormal gene, introduced into an animal by nonnatural means, i.e., by human manipulation.

Transgenic animal: A animal into which has been introduced, by nonnatural means, i.e., by human manipulation, one or more transgenes.

DETAILED DESCRIPTION OF THE PREFERRED EMBODIMENTS

In its broadest form, the invention comprises a novel mammalian protein know as "ARF-p19," and active fragments thereof (in particular the amino acid sequence encoded by Exon 1β) that regulate the cell cycle; nucleic acid molecules having sequences encoding such polypeptide sequences; antibodies specific for ARF-p19; transgenic non-human animals with alterations in the gene encoding ARF-p19; methods of making ARF-p19 nucleic acids and polypeptides; methods of making ARF-p19-specific antibodies; methods of making transgenic non-human animals with alterations in the gene encoding ARF-p19; and methods of using the nucleic acids, proteins, antibodies and transgenic animals of the invention to detect ARF-p19 nucleic acids or proteins in a sample, to diagnose cancers or predispositions thereto, to evaluate compositions for their therapeutic or oncogenic potential, and to prepare therapeutic compositions for the treatment of tumors and cancers.

The present invention also provides that, mice lacking $p19^{ARF}$ but expressing functional $p16^{INK4a}$ develop tumors early in life. Their embryo fibroblasts (MEFs) do not senesce and are transformed by oncogenic Ha-ras alone. Conversion of ARF (+/+) or (+/−) MEF strains to continuously proliferating cell lines involves loss of either $p19^{ARF}$ or p53. p53-mediated checkpoint control is unperturbed in ARF-null fibroblast strains, whereas p53-negative cell lines are resistant to $p19^{ARF}$-induced growth arrest. Therefore, INK4a encodes growth inhibitory proteins that act upstream of the retinoblastoma protein and p53. Mutations and deletions targeting this locus in cancer cells are unlikely to be functionally equivalent. Surprisingly, the previously described phenotypic consequences of INK4a disruption are reproduced in mice selectively nullizygous for $p19^{ARF}$ alone, indicating that ARF is a bona fide tumor suppressor. The results described herein further suggest that ARF and p53 regulate senescence of MEFs, and that $p19^{ARF}$ requires wild-type p53 to induce G1 phase arrest.

The present invention also provides that disruption of the INK4a-ARF locus (which encodes two proteins, $p16^{INK4a}$ and $p19^{ARF}$ that restrain cell growth by affecting the functions of the retinoblastoma protein and p53 respectively) by deletions or point mutations is a common event in human cancer, perhaps second only to the loss of p53. Using insect cells infected with baculovirus vectors and NIH-3T3 fibroblasts infected with ARF retrovirus, it is determined that mouse $p19^{ARF}$ can interact directly with p53, as well as with the p53 regulator mdm2. ARF can bind p53-DNA complexes, and it depends upon functional p53 to transeriptionally induce mdm2 and the cyclin-dependent kinase inhibitor $p21^{Cip1}$, and to arrest cell proliferation. Binding of $p19^{ARF}$ to p53 requires the ARF N-terminal domain (amino acids 1–62) that is necessary and sufficient to induce cell cycle arrest. Overexpression of $p19^{ARF}$ in wild type or ARF-null mouse embryo fibroblasts increases the half-life of p53 from 15 to ~75 minutes, correlating with an increased p53-dependent transcriptional response and growth arrest. Surprisingly, when overexpressed at supra-physiologic levels after introduction into ARF-null NIH-3T3 cells or mouse embryo fibroblasts, the p53 protein is handicapped in inducing this checkpoint response. In this setting, reintroduction of $p19^{ARF}$ restores p53's ability to induce $p21^{Cip1}$ and mdm2, implying that, in addition to stabilizing p53, ARF modulates p53-dependent function through an additional mechanism. As disclosed herein, $p19^{ARF}$ can directly associate with p53 as well as with mdm2 and suggest that ARF regulates cellular functions other than p53 stabilization.

Establishment of primary mouse embryo fibroblasts (MEFs) as continuously growing cell lines is normally accompanied by loss of the p53 or $p19^{ARF}$ tumor suppressors, which act in a common biochemical pathway. As shown herein, MYC rapidly activates ARF and p53 gene expression in primary MEFs and triggers replicative crisis by inducing apoptosis. MEFs that survive MYC overexpression sustain p53 mutation or ARF loss during the process of establishment and become immortal. MEFs lacking ARF or p53 exhibit an attenuated apoptotic response to MYC ab inito, and rapidly give rise to cell lines that proliferate in chemically defined medium lacking serum. Therefore, ARF regulates a p53-dependent checkpoint that safeguards cells against hyperproliferative, oncogenic signals. The present invention provides that ARF is a target of MYC activation and that the loss of ARF, like loss of p53, can attenuate MYC-induced cell death. ARF's normal role is shown to be to respond to hyperproliferative signals, thereby facilitating p53 activation through a signaling pathway that differs from those induced by DNA damage.

Nucleic Acids and Related Embodiments

In one embodiment, the invention comprises nucleic acids having sequences encoding mouse ARF-p19, human ARF-p19 or ARF-p19 polypeptides from other mammals, and includes nucleic acids encoding peptides comprising most of or all of exon 1β such as the protion encoding amino acids 1–62 of SEQ ID NO:2 and amino acids 1–62 of SEQ ID NO:4. For example, the invention provides cDNA molecules encoding mouse ARF-p19 (SEQ ID NO:1). The ARF-p19 cDNAs of the invention are in him used to isolate additional nucleic acids that encode ARF-p19 polypeptide sequences, such as mouse and human genomic DNA clones. Moreover, because the homology between the nucleotide sequences of mouse and human ARF-p19 genesis quite high, the mouse and human nucleic acids may be used to design probes or degenerate primers for PCR in order to isolate cDNA and genomic clones of ARF-p19 genes from other mammals.

One skilled in the art can readily adapt the nucleic acid sequences of the invention to any system which is capable of producing nucleic acids to produce the nucleic acids of the invention. The nucleic acids of the invention, which may optionally comprise a detectable label, may be prepared as cDNA clones, genomic clones, RNA transcribed from either cDNA or genomic clones, synthetic oligonucleotides, and/or synthetic amplification products resulting e.g., from PCR. The nucleic acids of the invention may be prepared in either single- or double-stranded form.

Methods of preparing cDNA clones are known in the art (see, for example, Chapter 8 in Sambrook et al., *Molecular Cloning: A Laboratory Manual*, vol. 2, 2d. Ed., Cold Spring Harbor Laboratory Press, Cold Spring Harbor, N.Y. (1989) pages 8.1–886). Methods of analyzing genomic DNA sequences and preparing genomic clones are known in the art (see, for example, Chapter 9 in Sambrook et al., *Molecular Cloning: A Laboratory Manual*, vol. 2, 2d. Ed., Cold Spring Harbor Laboratory Press, Cold Spring Harbor, N.Y. (1989), pages 9.1–9.62; and Chapter 2 in *Current Protocols in Molecular Biology*, vol. 1, Ausubel et al., eds., John Wiley & Sons, Inc., Boston, Mass. (1994), pages 2.1.1–2.14.8). Genomic DNA sequences, i.e., chromosomally-derived nucleic acids, are isolated (see Example 9) from mice and other non-human animals and used for the production of transgenic non-human animals. RNA containing ARF-p19 sequences may be prepared from cells expressing ARF-p19 according to methods known in the an (see., e.g., Chapter 4 in *Current Protocols in Molecular Biology*, vol. 1, Ausubel et al., eds., John Wiley & Sons, Inc., Boston, Mass. (1994), pages 4.1.1–4.10.11), or may be generated by in vitro transcription using the DNA molecules of the invention (see, e.g., Chapter 10 in Sambrook et al., *Molecular Cloning: A Laboratory Manual*, vol. 2, 2d. Ed., Cold Spring Harbor Laboratory Press, Cold Spring Harbor, N.Y. (1989), pages 10.1–10.70).

Synthetic oligonucleotides having ARF-p19-specific nucleotide sequences can be prepared using the nucleic acid sequences of the invention by known methods (see, e.g., Chapter 11 in Sambrook et al., *Molecular Cloning: A Laboratory Manual*, vol. 2, 2d. Ed., Cold Spring Harbor Laboratory Press, Cold Spring Harbor, N.Y. (1989), pages 11.1–11.61). When used as primers in the polymerase chain reaction (PCR), the synthetic oligonucleotides preferably contain from about 15 to about 30 contiguous nucleotides exactly corresponding to unique portions of the ARF-p19 sequences of the invention, but may optionally contain additional nucleotides 5' therefrom (Innis, M.A. and Gelfand, D.H., Chapter 1 in *PCR Protocols: A Guide to Methods and Applications*, Innis et al., eds., Academic Press, Inc., New York (1990), pages 3–12; Saiki, R.K., Chapter 2 in *PCR Protocols: A Guide to Methods and Applications*, Innis et al., eds., Academic Press, Inc., New York (1990), pages 13–20). Synthetic amplification products are prepared using the synthetic oligonucleotides of the invention in amplification systems such as PCR (see, e.g., U.S. Pat. No. 4,965,188 to Mullis et al. (Oct. 23, 1990); Scharf, S.J., Chapter 11 in *PCR Protocols: A Guide to Methods and Applications*, Inns et al., eds., Academic Press, Inc., New York (1990), pages 84–98; Chapter 15 in *Current Protocols in Molecular Biology*, vol.2, Ausubel et al., eds., John Wiley & Sons, Inc., Boston, Mass. (1994), pages 15.0.1–15.8.8; and Chapter 14 in Sambrook et al., *Molecular Cloning: A Laboratory Manual*, vol. 2, 2d. Ed., Cold Spring Harbor Laboratory Press, Cold Spring Harbor, N.Y. (1989), pages 14.1–14.35). Those of skill in the art will appreciate that chemical derivatives of nucleotide structures can be substituted for natural nucleotides in the nucleic acids of the invention.

Methods of nucleic acid expression: In one aspect of this embodiment of the invention, the nucleic acids of the invention are used to prepare ARF-p19 proteins, active fragments thereof, or fusion proteins derived from ARF-p19, via recombinant DNA technology. By inserting any of the nucleic acids of the invention that encode ARF-p19 polypeptide sequences into an appropriate expression vector, and introducing the resultant expression vector construct into appropriate host cells, those skilled in the art can produce large quantities of ARF-p19 polypeptides.

There are numerous host/expression vector systems available for the generation of proteins from the isolated nucleic acids of the invention. These include, but are not limited to, bacteria/plasmid systems, bacteria/phage systems, eukaryotic cell/plasmid systems, eukaryotic cell/virus systems, and the like (see, for example, U.S. Pat. No. 4,440,859 to Rutter et al. (Apr. 3, 1984); Chapter 16 in *Current Protocols in Molecular, Biology*, vol. 2, Ausubel et al., eds., John Wiley & Sons, Inc., Boston, Mass. (1994), pages 16.0.5–16.2016; and Sambrook et al., *Molecular Cloning: A Laboratory Manual*, Vol. 3, 2d. Ed., Cold Spring Harbor Laboratory Press, Cold Spring Harbor, N.Y. (1989)). One skilled in the art can readily adapt the nucleic acids of the invention to any host/expression vector system which is capable of propagating and expressing heterologous nucleic acids to produce the proteins or polypeptides of the invention. Preferred host/expression systems include bacteria/plasmid systems and insect cell/baculoviral expression vector systems.

Diagnostic methods and kits: In another aspect of this embodiment, ARF-p19 nucleic acid sequences are used to prepare oligonucleotide probes, or PCR primers, to serve as materials for diagnostic tests for ARF-p19 expression, mutation, or deletion in samples of cells isolated from mammals. Deletions of the genes encoding p15 and p16 occur frequently in cancer cells, and the resulting loss of their anti-proliferative functions can contribute to tumorigenesis (Noburi et al., *Nature* 368:753–756 (1994)). Similarly, point mutations, deletions or other mutations in the genes encoding ARF-p19 are diagnostic of cancer or indicative of a predisposition to develop certain types of cancers.

Mutations in the human gene for ARF-p19 are detected by any of a variety of methods depending in part on the nature of the mutation of interest. Deletions and insertions of about 100 base pairs (bp) or more are detected by electrophoretic separation of genomic DNA and hybridization analysis using nucleic acid probes derived from unique portions of the nucleotide sequence of the human ARF-p19 coding sequence (SEQ ID NO:3; see also FIG. 7), or by PCR of genomic DNA using synthetic oligonucleotides derived from the unique portions of the nucleotide sequence of the human ARF-p19 coding sequence as primers. The term "the unique portions of the nucleotide sequence of human ARF-p19" is intended to encompass nucleotide sequences that occur in molecules encoding ARF-p19 but which are not found in p16-InK4a mRNAs.

In one aspect, the invention comprises methods of detecting the presence of a nucleic acid polymorphism associated with a predisposition to develop cancer by analyzing DNA or RNA from a mammal using nucleic acid molecules containing part or all of the unique portions of the nucleotide sequences from an ARF-p19 gene from a mammal, such as a mouse or a human, or the reverse complement thereof. Such methods are used in conjunction with any procedure which will detect the nucleic acids of the invention. Examples of such procedures include hybridization analysis using the nucleic acids of the invention, i.e., isolation of nucleic acids from the cells of a mammal, followed by restriction digestion, separation by a means such as gel electrophoresis, transfer to nitrocellulose or a comparable material, and detection of ARF-p19 nucleic acid sequences thereon by exposure to detectably labeled nucleic acid probes which contain nucleotide sequences encoding ARF-p19 polypeptide sequences.

In one embodiment of the present invention, the preferred method of detecting the presence of a DNA polymorphism associated with a predisposition to develop cancer involves RFLP (restriction fragment length polymorphism) techniques based on amplification ARF-p19 sequences via PCR, followed by restriction digestion and agarose gel electrophoresis. In this method, a biological sample containing nucleated cells, preferably leukocytes, is obtained from a human. Suitable biological samples having nucleated cells that may be used in this invention include, but are not limited to, blood and tissue. The method of obtaining the biological sample will vary depending upon the nature of the sample. By the term "nucleated cells" is meant any cell containing a nucleus. Examples of such cells include, but are not limited to, white blood cells, epithelial cells, or mesenchymal cells. The cells are then isolated from the sample and the DNA from the nucleated cells is purified using conventional methods known in the art such as phenol-chloroform extraction, lytic enzymes, chemical solutions and centrifugation, or size exclusion chromatography (see, for example, Blin and Stafford, *Nucl. Acid Res.* 3:2303–2308 (1976); Maniatis, *Molecular Cloning: A Laboratory Manual*, Cold Spring Harbor Laboratory, Cold Spring Harbor, N.Y. (1982)). Following isolation, the DNA sequences of interest are amplified using conventional PCR methods (see, for example, Innis et al., *PCR Protocols*, Academic Press, NY (1990); Mullis et al., *Cold Spring Harbor Symp. Quant. Biol.* 51:263–273 (1986); Mullis and Faloona, *Methods Enzymol.* 155:335–350 (1987); and Mullis et al., U.S. Pat. No. 4,965,188 (Oct. 23, 1990)).

In one aspect of this embodiment, sequences comprising the unique portions of nucleotide sequences for ARF-p19 are utilized as primers for specific amplification of ARF-p19 nucleic acids (see Example 2). In such an embodiment the amplified product is subjected to restriction digestion prior to visualization. Different alleles of ARF-INK4a will yield amplified fragments of differing size after digestion with an appropriate restriction endonuclease.

The amplified DNA is then precipitated, and digested with a restriction enzyme, such as BamHI, BglII, PstI, or EcoRI. Digested DNA fragments are separated according to their molecular weights to form a pattern, typically using agarose gel electrophoresis. Following electrophoresis, the gel is stained with an appropriate agent, such as ethidium bromide, using standard protocols, and photographed under ultraviolet transillumination. Polymorphisms result in the appearance of additional bands (i.e., bands not found in the wild-type ARF-InK4a allele) on the gel.

In an alternative aspect of this embodiment, the DNA isolated from the cells' nuclei is digested with a given restriction endonuclease, utilizing PCR amplification. The restriction endonucleases that may be used in this invention include, but are not limited to, BamHI, BglII, PstI, or EcoRI. After a digest is obtained, and the DNA is separated by standard technique, for example by agarose gel electrophoresis, the separated bands are probed with one or more DNA fragments containing a unique portion of the nucleotide sequences encoding human ARF-p19 polypeptide sequences. In one aspect of this embodiment, the preferred probe of the invention is based on the cDNA or genomic sequence from the gene for human ARF-p19.

The use of RFLP technology is only one preferred embodiment of detecting polymorphisms in the nucleic acids of the invention. Since, ultimately, the use of RFLP depends on polymorphism in DNA restriction sites along the nucleic acid molecule, other methods of detecting the polymorphism can also be used. Any method of analysis which allows one skilled in the art to determine the linkage between the polymorphism detected by the probes and primers of the present invention can be utilized. Techniques such as direct location of a polymorphism affecting ARF-p19 at its chromosomal location by in situ hybridization (e.g., FISH) using radiolabeled, fluorescence-labeled, or enzyme-labeled probes may be employed. Other suitable techniques include, but are not limited to, amplification methods such as the ribonuclease mis-match cleavage assay and direct oligonucleotide hybridization.

Any size fragment of the human InK4A gene (SEQ ID NO:3) can be utilized as a probe as long as it is capable of hybridizing to a restriction fragment which displays a polymorphism within an intron or an exon required for ARF-p19 expression. The hybridization probes can be labeled by standard labeling techniques such as with a radiolabel, enzyme label, fluorescent label, biotin-avidin label, chemilunminescence, and the like. After hybridization, the probes are visualized using known methods. Comparison of the RFLP or RFLP's for the subject under investigation will quickly reveal the presence or absence of polymorphisms in the gene encoding human ARF-p19 linked to a predisposition to cancer. Polymorphisms that may be detected by the methods of the invention include RFLPs, point mutations, insertions, deletions, inversions, alternately spliced mRNAs, and the like.

The materials for use in this aspect of the invention are ideally suited for the preparation of a kit. Specifically, the invention provides a compartmentalized kit to receive in close confinement, one or more containers which comprises: (a) a first container comprising one or more of the probes or amplification primers of the present invention; and (b) one or more other containers comprising one or more of the following: a sample reservoir, wash reagents, reagents capable of detecting presence of bound probe from the first container, or reagents capable of amplifying sequences hybridizing to the amplification primers.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (Trig-buffers, etc.), and containers which contain the reagents used to detect the bound probe or amplified product.

Types of detection reagents include labeled secondary probes, or in the alternative, if the primary probe is labeled, the enzymatic, or antibody binding reagents which are capable of reacting with the labeled probe. One skilled in the art will readily recognize that the disclosed probes and amplification primers of the present invention can readily be incorporated into one of the established kit formats which are well known in the art. In one example, a first container may contain a hybridization probe. The second container may contain the restriction enzyme to be used in the digest. Other containers may contain reagents useful in the localization of labeled probes, such as enzyme substrates such as x-gal tagged avidin if a biotinylated probe is utilized. Still other containers may contain buffers, etc.

Gene therapy: In another embodiment of this invention, ARF-p19 nucleic acid sequences including nucleic acid sequences encoding active fragments of ARF-p19 are used for gene therapy, i.e., to inhibit, enhance or restore expression of ARF-p19 in cells with reduced, altered or no ARF-p19 activity, using the nucleic acid sequences of the invention.

1. In order to enhance or restore ARF-p19 activity to cells in need of growth regulation, ARF-p19 expression constructs are prepared. An expression construct consists of nucleic acid sequences encoding a protein having ARF-p19 polypeptide sequences operably linked to nucleic acid sequences required for genetic expression in a cell (such as promoters) in an expression vector. The expression constructs are introduced into cells, wherein they direct expression of proteins having ARF-p19 polypeptide sequences. The expressed proteins may be fusion proteins that additionally include polypeptide sequences designed to improve the in vivo activity, targeting and/or stability of the gene products expressed by the expression construct.

The expressed proteins function to restore or enhance ARF-p19 function in their host cells and thus negatively regulate the progression of the cell though the cell cycle. The disclosure demonstrates that, even in cells genetically engineered to overexpress cyclin D and thus possessing 5–10 fold greater levels of CDKs than corresponding wild-type cells, the constitutive expression of ARF-p19 in a cell results in G1 or G2 phase arrest (see Example 5). Thus, even in cells with runaway cyclin D expression, the introduction of ARF-p19 function in excess inhibits the progression of the cells through the cell cycle and thus prevents their further growth.

2. In order to inhibit ARF-p19 activity in cells in need of growth stimulation, synthetic antisense oligonucleotides are prepared from the coding sequences for ARF-p19 found in cDNA clones. An antisense oligonucleotide consists of nucleic acid sequences corresponding to the reverse complements of ARF-p19 coding sequences or otter sequences required to be present in ARF-p19 mRNA molecules for in vivo expression. The antisense oligonucleotides are introduced into cells, wherein they specifically bind to ARF-p19 mRNA molecules (and thus inhibit translation of ARF-p19 gene products), or to double-stranded DNA molecules to form triplexes (see U.S. Pat. No. 5,190,931 to Inouye (Mar. 2, 1993); Riordan and Martin, Nature 350:442–443 (1991)).

Because antisense oligonucleotides bind with high specificity to their targets, selectivity is high and toxic side effects resulting from misdirection of the compounds are minimal, particularly given the present state of the art with regard to the design of, preparation and chemical modification of, and means of delivery to cells for, oligonucleotides (see, e.g., Wagner, R.W., *Nature* 372:333–335 (1994); Tseng and Brown, *Cancer Gene Therapy* 1:65–71 (1994); Morishita, R., et al., *J. Clin. Invest.* 93:1458–1464 (1994); Stein and Cheng, *Science* 26/:1004–1012 (1993); Lisziewicz, J., et al., *Proc. Natl. Acad. Sci.* (*USA*) 90:3860–3864 (1993); Watson, P.H. et al., *Cancer Res.* 51:3996–4000 (1991); Han, L., et al., *Proc. Natl. Acad. Sci.* (*USA*) 88:4313–4317 (1991); Florini and Ewton, *J. Biol. Chem.* 265:13435–13437 (1990); and Ulhmann, and Peyman, *Chem. Reviews* 90:543–583 (1990)). Means for the delivery of oligonucleotides to cells include, but are not limited to, liposomes (see, e.g., Renneisen, K., et al., *J. Biol. Chem.* 265:16337–16342 (1990)) and introduction of expression constructs that direct the transcription of antisense oligoribonucleotides in vivo (see, e.g., Shohat, O., et al., *Oncogene* 1:277–283 (1987)).

Polypeptides and Related Embodiments

In one embodiment, the invention comprises proteins having amino acid sequences of mouse ARF-p19 protein, human ARF-p19 protein, active fragments of the ARF-p19 polypeptide and ARF-p19 polypeptides from other mammals. For example, the invention provides the complete amino acid sequences of mouse ARF-p19 (SEQ ID NO:2) and of human ARF-p19 (SEQ ID NO:4). When introduced into mammalian cells ARF-p19 proteins induce cell cycle arrest or, at lower concentrations, slow cell growth to a desired rate. ARF-p19 can also act as a tumor suppressor.

One skilled in the art can readily adapt the amino acid sequences of the invention to a variety of known applications. For example, fusion proteins that comprise amino acid sequences from ARF-p19 and a second polypeptide can be produced by recombinant DNA technology to generate novel proteins having properties of both parent proteins (see Example 4). Similarly, the proteins of the invention can be conjugated to other proteins in order to target the conjugated protein to CDK-cyclin complexes in a cell. Synthetic oligopeptides (a.k.a. "peptides") generally contain from about 5 to about 100 contiguous amino acids exactly corresponding to the polypeptide sequence of ARF-p19 of the invention, but may optionally contain additional amino acids at the carboxyl terminus, the amino terminus, or both. Moreover, those of skill in the art will appreciate that substitution of endogenous amino acids for chemical derivatives and/or isomers of amino acids will yield peptides with properties that are enhanced relative to the native ARF-p19 proteins. Properties that may be so altered include, for example, in vivo, stability.

Antibodies and Related Embodiments

In another embodiment of the invention, ARF-p19 proteins, or oligopeptide sequences derived therefrom, are used to create antibody compositions that specifically recognize (bind) ARF-p19 epitopes. Antibodies to ARF-p19 serve as probes for diagnostic tests for ARF-p19 expression or as diagnostic materials. Antibodies to ARF-p19 can also be conjugated to toxins to generate specific immunotoxins for use in mammalian therapy.

Methods of generating antibodies using purified proteins or synthetic oligopeptides are known in the art (see *Antibodies: A Laboratory Manual*, Harlow, E., and Lane, D., Cold Spring Harbor Laboratory, Cold Spring Harbor, N.Y. (1988)). The antibody compositions of the invention may be polyclonal, monospecific or monoclonal.

Diagnostic methods and kits: In one aspect of this embodiment, the concentration of ARF-p19 protein in a sample of cells from a mammal is determined by contacting the sample with a detectably labeled antibody composition specific to ARF-p19, qualitatively or quantitatively determining the amount of label bound or not bound in the sample, and calculating therefrom the concentration of ARF-p19 in the sample. The sample of cells is obtained from a mammal and are washed in an appropriate buffer such as Hank's balanced salt solution. The cells are lysed and incubated with a detectably labeled ARF-p19-specific antibody composition for an appropriate amount of time. The cells are washed with the buffer a second time to remove unbound antibody. The amount of bound or unbound labeled antibody is then detected by conventional means.

Alternatively, unlabeled ARF-p19-specific antibody compositions, bound or unbound in a sample, are detected using a secondary antibody or protein which is specific for an immunoglobulin, e.g., protein A, protein G, anti-IgM or anti-IgG antibodies. In this alternative embodiment, the secondary (anti-immunoglobulin) antibodies, which may be monoclonal or polyclonal, are detectably labeled and are detected in the course of carrying out the method.

Alternatively, ARF-p19 levels in a sample of mammalian cells are determined by detecting the level of soluble ARF-p19 in a sample of lysed cells. In this aspect, a sample of lysed cells obtained from a mammal is contacted with an ARF-p19-specific antibody composition which is immobilized onto a solid matrix, and allowed to incubate so as to form an ARF-p19/ARF-p19-specific antibody complex. Following a wash step with suitable buffers to remove the unbound antibody, a detectably labeled molecule which binds to the ARF-p19-specific antibody composition is added. The amount of bound label then is detected to determine the concentration of ARF-p19 present in the sample. Suitable types of immunoassays for detecting ARF-p19 include sandwich immunoassay and competition assays, performed using conventional methods. Naturally, other ligands specific for ARF-p19 may be used in lieu of ARF-p19-specific antibody compositions.

Of course, the specific amounts of ARF-p19-specific antibody compositions and detectably labeled second antibodies, the temperature and time of incubation, as well as other assay conditions may be varied, depending on various factors including the concentration of ARF-p19 in the sample, the nature of the sample, and the like. Those skilled in the art will be able to determine operative and optimal assay conditions for each determination by employing routine experimentation. Other such steps as washing, stirring, shaking, filtering and the like may be added to the assays as is customary or necessary for the particular situation.

A variety of means may be used to detectably label antibody compositions for use in the methods of the invention. For example, one means by which an ARF-p19-specific antibody composition, or secondary antibodies, can be detectably labeled is by conjugation to an enzyme. The conjugated enzyme, when later exposed to its substrate, will react with the substrate in such a manner as to produce a chemical moiety which can be detected, for example, by spectrophotometric, fluorometric or by visual means. Enzymes which can be used to detectably label antibody compositions include, but are not limited to, malate dehydrogenase, staphylococcal nuclease, delta-v-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase. Antibody compositions may also be labeled with a radioactive isotope which can be determined by such means as the use of a gamma counter or a scintillation counter or by autoradiography. It is also possible to label antibody compositions with a fluorescent compound. When fluorescently labeled antibody is exposed to light of the proper wave length, its presence can then be detected due to the fluorescence of the dye. Among the most commonly used fluorescent labeling compounds are fluorescence isothiocyanate, rhodamine, phycoerthrin, phycocyanin, allophycocyanin, o-phthaldehyde and fluorescamine. Antibodies can also be detectably labeled using fluorescence emitting metals such as $^{152}$Eu, or others of the lanthanide series. These metals can be attached to ARF-p19-specific antibodies using such metal chelating groups as diethylenetriaminepentaacetic acid (DTPA) or ethylenediaminetetraacetic acid (EDTA). Antibodies also can be detectably labeled by coupling to a chemiluminescent compound. The presence of chemiluminescent-tagged antibodies is then determined by detecting the presence of luminescence that arises during the course of a chemical reaction. Examples of particularly useful chemiluminescent labeling compounds are luminol, isoluminol, theromatic acridium ester, imidazole, acridinium salt and oxalate ester. Likewise, a bioluminescent compound may be used to label antibody compositions for use in the methods of the present invention. Bioluminescence is a type of chemiluminescence found in biological systems in which a catalytic protein increases the efficiency of the chemiluminescent reaction. The presence of a bioluminescent protein's determined by detecting the presence of luminescence. Important bioluminescent compounds for purposes of labeling are luciferin, luciferase and aequorin.

Detection of bound or unbound antibodies may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

In another embodiment of the present invention, kits are provided which contain the necessary reagents to carry out the previously described immunoassays with ARF-p19-specific antibodies, in order to diagnose certain types of cancers, or to detect a predisposition for certain types of cancers, in a mammal.

Specifically, the invention provides a compartmentalized kit to receive, in close confinement, one or more containers which comprises: (a) a first container containing an ARF-p19-specific antibody; and (b) one or more other containers containing one or more of the following: wash reagents, and reagents capable of detecting presence of bound or unbound ARF-p19-specific antibodies.

In detail, a compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline. Tris-buffers, etc.), and containers which contain the reagents used to detect the bound antibody.

Types of detection reagents include detectably labeled secondary antibodies, or in the alternative, if the primary antibody is detectably labeled, the appropriate enzymatic or antibody binding reagents which are capable of reacting with the labeled antibody. One skilled in the art will readily recognize that the disclosed antibodies of the present invention can readily be incorporated into any one of the variety of established kit formats which are well known in the art.

Therapeutics and Related Embodiments

Another embodiment of the invention includes screening for and producing new compounds that inhibit the activity of ARF-p19, to be applied to mammalian cells in need of reduced regulation of their cell cycles, cellular growth, and/or DNA replication. For example, in order to promote cellular growth in, e.g., healing processes, "negative-dominant" (Herskowitz, I., Nature 329:219–222 (1987)) ARF-p19 variants are prepared which competitively inhibit endogenous ARF-p19 proteins and thereby reduce ARF-p19 activity within a cell. As another example of a means by which cellular growth may be promoted, antibodies that bind regions of ARF-p19 involved in its biological action are introduced into a cell and prevent endogenous ARF-p19 proteins from functioning, thereby reducing ARF-p19 activity within a cell.

In a related embodiment, proteins, fusion proteins, conjugates, or synthetic oligopeptides having ARF-p19 function can be introduced into eukaryotic cells to arrest their progression from G1 to S phases, or from G2 to M phases, during interphase and thus inhibit growth of undesired cells or act as tumor suppressors, e.g., cancer cells (see Example 5). ARF-p19, or derivatives thereof can be employed in combination with conventional excipients, i.e., pharmaceutically acceptable organic or inorganic carrier substances suitable for parenteral application which do not deleteriously react with the active compound. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions preferably oily or aqueous solutions, as well as suspensions, emulsions, or implants. Aqueous suspensions may contain substances which increase the viscosity of the suspension and include, for example, sodium carboxymethyl cellulose, sorbitol, and/or dextran. Optionally, the suspension may also contain stabilizers.

The term "therapeutically effective amount," for the purposes of the invention, refers to the amount of ARF-p19 or derivatives thereof which is effective to achieve its intended purpose. While individual needs vary, determination of optimal ranges for effective amounts of ARF-p19 or its derivatives is within the skill of the art. Generally, the dosage required to provide an effective amount of the composition, and which can be adjusted by one of ordinary skill in the art will vary, depending on the age, health, physical condition, weight, extent of disease of the recipient, frequency of treatment and the nature and scope of the desired effect.

According to the invention, the component or components of a therapeutic composition, e.g., a ARF-p19, active fragment thereof, or mimic thereof (identified by a method exemplified herein) and a pharmaceutically acceptable carrier, of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In a preferred aspect, an ARF-p19 fragment or mimic of the present invention can cross cellular or nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to an ARF-p19 fragment, for example. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is an antibody. Preferably, the targeting molecule is a monoclonal antibody. In one embodiment, to facilitate crosslinking the antibody can be reduced to two heavy and light chain heterodimers or the F(ah')$_2$ fragment can be reduced, and crosslinked to the ARF-p19 fragment via the reduced sulfhydryl.

Antibodies for use as targeting molecule are specific for cell surface antigen. In one embodiment, the antigen is a receptor. For example, an antibody specific for a receptor of a particular tumor cell being treated can be used. This invention further provides for the use of other targeting molecules, such as lectins, carbohydrates, proteins and steroids.

In another embodiment, the therapeutic compound can be delivered in a vesicle, in particular a liposome [see Langer, *Science,* 249:1527–1533 (1990); Treat et al., in *Liposomes in the Therapy of Infectious Disease and Cancer,* Lopez-Berestein and Fidler (eds.), Liss: New York, pp. 353–365 (1989); Lopez-Berestein, *ibid.,* pp. 317–327; see generally *ibid.*]. To reduce its systemic side effects, this may be a preferred method for introducing an ARF-p19.

In yet another embodiment, the therapeutic compound can be delivered in a controlled release system. For example, the polypeptide may be administered using intravenous infusion, an implantable osmotic pump, a transdermal patch, liposomes or other modes of administration. In one embodiment, a pump may be used [see Langer, supra; Sefton, *CRC Crit. Ref. Biomed. Eng.*, 14:201 (1987); Buchwald et al., *Surgery*, 88:507 (1980); Saudek et al., *N. Engl. J. Med.*, 321:574 (1989)]. In another embodiment, polymeric materials can be used [see *Medical Applications of Controlled Release*, Langer and Wise (eds., CRC Press: Boca Raton, Florida (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.*, 23:61 (1983); see also Levy et al., *Science*, 228:190 (1985); During et al., *Ann. Neurol.*, 25:351 (1989); Howardet al., *J. Neurosurg.*, 71:105 (1989)]. In yet another embodiment, a controlled release system can be placed in proximity of the therapeutic target, i.e., a brain tumor, thus requiring only a fraction of the systemic dose [see, e.g., Goodson, in *Medical Applications of Controlled Release*, supra, vol. 2, pp. 115–138 (1984)]. Preferably, a controlled release device is introduced into a subject in proximity of the site of a tumor. Other controlled release systems are discussed in the review by Langer [*Science*, 249:1527–1533 (1990)].

Pharmaceutical Compositions. In yet another aspect of the present invention, provided are pharmaceutical compositions of the above. Such pharmaceutical compositions may be for administration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g. Tween 80, Polysorbate 80), anti-oxidants (e.g., ascorbic acid, sodium metabisulfite), preservatives (e.g., thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. [1990, Mack Publishing Co., Easton, Pa. 18042] pages 1435–1712 which are herein incorporated by reference. The compositions may be prepared in liquid form, or may be in dried powder, such as lyophilized form.

Oral delivery. Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925, 673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G.S. Banker and C.T. Rhodes Chapter 10, 1979, herein incorporated by reference. In general, the formulation may include an ARF-p19 (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time it the body. An example of such a moiety is polyethylene glycol, For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdcx, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Binders also may be used to hold the therapeutic agent together to form a hard tablet and include materials from natural products such as acacia, tragacanth, starch and gelatin.

An anti-frictional agent may be included in the formulation of the therapeutic to prevent sticking during the formulation process. Lubricants may be used as a layer between the therapeutic and the die wall. Glidants that might improve the flow properties of the drug during formulation and to aid rearrangement during compression also might be added. The glidants may include starch, talc, pyrogenic silica and hydrated silicoaluminate.

In addition, to aid dissolution of the therapeutic into the aqueous environment a surfactant might be added as a wetting agent. Additives which potentially enhance uptake of the protein (or derivative) are for instance the fatty acids oleic acid, linoleic acid and linolenic acid.

Nasal Delivery. Nasal delivery of an ARF-p19 or derivative thereof is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Transdermal administration. Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued August 9, 1994 to Sibalis; U.S. Pat. No. 5,290,561, issued Mar. 1, 1994 to Farhadich et al.; U.S. Pat. No. 5.254.346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 8, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Pulmonary Delivery. Also contemplated herein is pulmonary delivery of the pharmaceutical compositions of the present invention. A pharmaceutical composition of the present invention is delivered to the lungs of a mammal while inhaling and traverses across the lung epithelial lining to the blood stream. Other reports of this include Adjei et al. [*Pharmaceutical Research,* 7:565–569 (1990); Adjei et al., *International Journal of Pharmaceutics,* 63:135–144 (1990) (leuprolide acetate); Braquet et al., *Journal of Cardiovascular Pharmacology,* 13(suppl. 5):143–146 (1989) (endothehn-1); Hubbard et al., *Annals of Internal Medicine,* vol. III, pp. 206–212 (1989) (α1-antitrypsin); Smith et al., *J. Clin. Invest.,* 84:1145–1146 (1989) (α-1-proteinase); Oswein et al., "Aerosolizalion of Proteins", *Proceedings of Symposium on Respiratory Drug Delivery II,* Keystone, Colorado, March, (1990) (recombinant human growth hormone); Debs et al., *J. Immunol.,* 140:3482–3488 (1988) (interferon-γ and tumor necrosis factor alpha); Platz et al., U.S. Pat. No. 5,284,656 (granulocyte colony stimulating factor)]. A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump acrosolization of a liquid formulation, and aerosolization of a dry powder formulation, can be used in the practice of the invention.

All such devices require the use of formulations suitable for the dispensing of pharmaceutical composition of the present invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified pharmaceutical composition of the present invention may also be prepared in different formulations depending on the type of chemical modification or the type of device employed.

Formulations suitable for use with a nebulizer, either jet or ultrasonic, may typically comprise pharmaceutical composition of the present invention (or derivative) dissolved in water at a concentration of e.g., about 0.1 to 25 mg of biologically active ingredients of a pharmaceutical composition of the present invention per mL of solution. The formulation may also include a buffer and a simple sugar (e.g., for stabilization and regulation of osmotic pressure of a pharmaceutical composition of the present invention). The nebulizer formulation may also contain a surfactant, to reduce or prevent surface induced aggregation of the pharmaceutical composition of the present invention caused by atomization of the solution in forming the aerosol.

The liquid aerosol formulations contain a pharmaceutical composition of the present invention and a dispersing agent in a physiologically acceptable diluent. The dry powder aerosol formulations of the present invention consist of a finely divided solid form of a pharmaceutical composition of the present invention and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The "term aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

Often, the aerosolization of a liquid or a dry powder formulation for inhalation into the lung will require a propellent. The propellent may be any propellant generally used in the art. Specific non-limiting examples of such useful propellants are a chlorofluorocarbon, a hydrofluorocarbon, a hydrochlorofluorocarbon, or a hydrocarbon, including trifluoromethane, dichlorodifluoromethane, dichlorotetrafluoroethnol, and 1,1,1,2-tetrafluoroethane, or combinations thereof Systems of aerosol delivery, such as the pressurized metered dose inhaler and the dry powder inhaler are disclosed in Newman, S.P., *Aerosols and the Lung,* Clarke, S.W. and Davia, D. editors, pp. 197–22 and can be used in connection with the present invention.

Liquid Aerosol Formulations. The present invention provides aerosol formulations and dosage forms. In general such dosage forms contain a pharmaceutical composition of the present invention in a pharmaceutically acceptable diluent. Pharmaceutically acceptable diluents include but are not limited to sterile water, saline, buffered saline, dextrose solution, and the like.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure.

Aerosol Dry Powder Formulations. It is also contemplated that the present aerosol formulation can be prepared as a dry powder formulation comprising a finely divided powder form of pharmaceutical composition of the present invention and a dispersant. Formulations for dispensing from a powder inhaler device will comprise a finely divided dry powder containing pharmaceutical composition of the present invention (or derivative) and may also include a bulking agent, such as lactose, sorbitol, sucrose, or mannitol in amounts which facilitate dispersal of the powder from the device, e.g., 50 to 90% by weight of the formulation. The pharmaceutical composition of the present invention (or derivative) should most advantageously be prepared in particulate form with an average particle size of less than 10 mm (or microns), most preferably 0.5 to 5 mm, for most effective delivery to the distal lung.

In a further aspect, recombinant cells that have been transformed with a nucleic acid encoding ARF-p19 or active fragment thereof and that express high levels of the polypeptide can be transplanted in a subject in need of ARF-p19. Preferably autologous cells transformed with ARF-p19 are transplanted to avoid rejection; alternatively, technology is available to shield non-autologous cells that produce soluble factors within a polymer matrix that prevents immune recognition and rejection.

Methods of Treatment, Methods of Preparing a Medicament. In yet another aspect of the present invention, methods of treatment and manufacture of a medicament are provided. Conditions alleviated or modulated by the administration of the present derivatives are those indicated above.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing. In addition, where appropriate, the size of the tumor may be relevant.

A subject in whom administration of ARF-p19 is an effective therapeutic regiment is preferably a human, but call be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Transgenic Animals and Related Embodiments

In another embodiment of the invention, ARF-p19 nucleic acid sequences can be used to create transgenic non-human animals to serve as animal models for ARF-p19 overexpression (transgenic expression) or mutations such as multiple stop codons ("knockouts" or "null alleles") or other mutations which alter one or more ARF-p19 activities without affecting InK4a-p16 activity. For example, transgenic mice having little or no ARF-p19 activity due to mutations in one or both alleles of the gene encoding ARF-p19 (INK4A) are prone to develop certain types of tumors.

The non-human animals of the invention comprise any animal having a deficiency of ARF-p19 activity as a result of the transgenic alteration of the gene(s) encoding ARF-p19. Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i.e., by human manipulation), one or more genes that do not occur naturally in the animal, e.g., foreign genes, genetically engineered endogenous genes, etc. The nonnaturally introduced genes, known as transgenes, may be from the same or a different species as the animal but not naturally found in the animal in the configuration and/or at the chromosonial locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. (Watson, J.D., et al., in *Recombinant DNA*, 2d Ed., Wil. Freeman & Co., New York (1992), pages 255–272; Gordon, J.W., *Intl. Rev. Cytol.* 115:171–229 (1989); Jaenisch, R., *Science* 240:1468–1474 (1989); Rossant, J., *Neuron* 2:323–334 (1990)).

Methods of preparing transgenic animals: In one aspect of this embodiment of the invention, the nucleic acids of the invention are used to prepare transgenic constructs to be introduced into non-human animals in order to generate the transgenic animals of the invention. Specifically, ARF-p19 sequences derived from the genome of the non-human animal of choice are used to create such transgenic constructs.

The transgenic non-human animals of the invention are produced by introducing ARF-p19 transgenic constructs into the germline of the non-human animal. Embryonic target cells at various developmental stages are used to introduce the transgenes of the invention. Different methods are used depending on the stage of development of the embryonic target cell(s).

1. Microinjection of zygotes is the preferred method for incorporating transgenes into animal genomes in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1–2 picoliters of a solution containing transgenic DNA sequences. The use of a zygote for introduction of transgenes has the advantage that, in most eases, the injected transgenic DNA sequences will be incorporated into the host animal's genuine before the first cell division (Brinster, et al. *Proc. Natl. Acad. Sci.* (*USA*) 82:4438–4442 (1985)). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the developmental stage known as a blastocyte. At this time, the blastomeres may be infected with appropriate retroviruses (Jaenich, R., *Proc. Natl. Sci.* (*USA*) 73:1260–1264). Infection of the blastomeres is enhanced by enzymatic removal of the zona pellucida (Hogan, et al., in *Manipulating the Mouse Embryo*, Cold Spring Harbor Press, Cold Spring Harbor, N.Y. (1986)). Transgenes are introduced via viral vectors which are typically replication-defective but which remain competent for integration of viral-associated DNA sequences, including transgenic DNA sequences linked to such viral sequences, into the host animal's genome (Jahner, et al., *Proc. Natl. Acad. Sci.* (*USA*) 32:6927–6931 (1985): Van der Putten, et al., *Proc. Natl. Acad. Sci.* (*USA*) 82:6148–6152 (1985)). Transfection is easily and efficiently obtained by culture of blastomeres on a mono-layer of cells producing the transgene-containing viral vector (Van der Putten, et al., *Proc. Natl. Acad. Sci.* (*USA*) 82:6148–6152 (1985); Stewart, et al., *EMBO Journal* 6:383–388 (1987)). Alternatively, infection may be performed at a later stage, such as a blastocoele (Jahner, D., et al., *Nature* 298:623–628 (1982)). In any event, most transgenic founder animals produced by viral integration will be mosaics for the transgenic allele; that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency (Jahner, D.,et al., *Nature* 298:623–628 (1982)). However, once a transgene has been introduced into germline cells by this method, offspring may be produced in which the transgenic allele is present in all of the animal's cells, i.e., in both somatic and germline cells.

b 3. Embryonic stem (ES) cells can also serve as target cells for introduction of the transgenes of the invention into animals. ES cells are obtained from pre-implantation embryos that are cultured in vitro (Evans, M.J., et al., *Nature* 292:154–156 (1981); Bradley, M. O., et al., *Nature* 309:255–258 (1984); Gossler, et al., *Proc. Natl. Acad. Sci.* (*USA*) 83:9065–9069 (1986); Robertson et al., *Nature* 322:445–448 (1986); Robertson, E.J., in *Teratocarcinomas and Embryonic Stem Cells: A Practical Approach*, Robertson, E.J., ed., IRL Press, Oxford (1987), pages 71–112). ES cells, which are commercially available (from, e.g., (Genome Systems, Inc., St. Louis, Mo.), can be transformed with one or more transgenes by established methods (Lovell-Badge, R.H., in *Teratocarcinomas and Embryonic Stem Cells: A Practical Approach*, Robertson, E.J., ed., IRL Press, Oxford (1987), pages 153–182). Transformed ES cells can be combined with an animal blastocyst, whereafter the ES cells colonize the embryo and contribute to the germline of the resulting animal, which is a chimera (composed of cells derived from two or more animals) (Jaeniseh, R., *Science* 240:1468–1474 (1988); Bradley, A., in *Teratocarcinomas and Embryonic Stem Cells: A Practical Approach*, Robertson, E.J., ed., IRL Press, Oxford (1987), pages 113–151). Again, once a transgene has been introduced into germline cells by this method, offspring may be produced in which the transgenic allele is present in all of the animal's cells, i.e., in both somatic and germline cells.

However it occurs, the initial introduction of a transgene is a Lamarekian (non-Mendelian) event. However, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism) (Leder et al., U.S. Pat. 5,175, 383 (Dec. 29, 1992); Kindt et al., U.S. Pat. No. 5,183,949 (Feb. 2. 1993): Small et al., *Cell* 46:13–18 (1986); Hooper et al., *Nature* 326:292–295 (1987); Stacey et al., *Nature* 332:131–136 (1988); Windle et al., *Nature* 343:665–669 (1990); Katz et al., *Cell* 74:1089–1100 (1993)). Transgenic animals that are predisposed to a disease may be used to identify compositions that induce the disease and to evaluate the pathogenic potential of compositions known or suspected to induce the disease (Berns, A.J.M., U.S. Pat. No. 5,174,986 (Dec. 29, 1992)).

Offspring that have inherited the transgenes of the invention are distinguished from littermates that have not inherited transgenes by analysis of genetic material from the offspring for the presence of biomolecules that comprise unique sequences corresponding to sequences of or encoded by, the transgenes of the invention. For example, biological fluids that contain polypeptides uniquely encoded by the transgenes of the invention may be immunoassayed for the presence of the polypeptides. A more simple and reliable means of identifying transgenic offspring comprises obtaining a tissue sample from an extremity of an animal, e.g., a tail, and analyzing the sample for the presence of nucleic acid sequences corresponding to the DNA sequence of a unique portion or portions of the transgenes of the invention. The presence of such nucleic acid sequences may be determined by, e.g., hybridization ("Southern") analysis with DNA sequences corresponding to unique portions of the transgene, analysis of the products of PCR reactions using DNA sequences in a sample as substrates and oligonucleotides derived from the transgene's DNA sequence, etc.

Null alleles: A preferred embodiment is a transgenic animal that is homozygous for a null (a.k.a. "knock-out")

allele of ARF-INK4A but which has a wild-type INK4A-p16 allele. For example, selective interruption of INK4A exon 1β eliminates ARF-INK4A expression but does not affect sequences encoding InK4a-p16. Additionally or alternatively, one or more point mutations that create stop codons in the ARF-p19 reading frame, but which result in silent mutations in the InK4a-p16 reading frame, are introduced by site-directed mutagenesis into cloned INK4A genomic nucleic acid sequences which are then reintroduced into the genome of an animal to generate a transgenic ARF-p19-deficient animal. The transgenic ARF-p19 null or ARF-p19-deficient animals of the invention are predisposed to develop certain types of cancers, including but not limited to melanomas, in a reproducible and thus reliable manner.

In order to generate null alleles in embryonic stem cells, the positive-negative selection strategy of Mansour et al. (*Nature* 336:348–352 (1988)) is applied. A positive selectable marker, for example the hygromycin phosphotransferase cassette (van Deursen and Wieringa, *Nucl. Acids Res.* 29:3815–3820 (1992)), is inserted into a 5' portion of an INK4 gene. This position for the positive selectable marker is chosen to obtain a genuine null mutant allele, i.e., to avoid translation of a truncated polypeptide. In the resulting targeting vector the hygromycin gene is flanked 5' and 3' by several kb of homologous murine genomic sequences. In addition, a negative selectable marker, for example the Herpes Simplex Virus (HSV) thymidine kinase (TK) gene, is placed in a 3' position flanking the region of homologous sequences in order to enable selection against nonhomologous integrants. Both the positive and negative selectable markers are inserted in the antisense orientation with respect to the transcriptional orientation of the Ink4 gene, and are expressed due to the TK promoter and Py F441 Polyonia enhancer. Linearized targeting construct is introduced into ES cells by electroporation or other suitable means and selection with hygromycin and FIAU (1-[2-deoxy, 2-fluoro-β-D-arabinofuranosyl]) is carried out for 7 to 10 days. Resistant colonies are expanded in 24-well plates; half of the cells in each well are cryo-preserved and the other half expanded for genotype analysis. Positive clones are stored in liquid nitrogen and thawed at least 3 days prior to blastocyst injection. Plastocysts are isolated, for example, at day 3.5 postcoitum by flushing the uterine horns of naturally mated C57BL/6 pregnant females with DMEM+10% FBS. Approximately 10 to 15 ES cells from each homologous recombinant clone with a normal karyotype are microinjected into recipient blastocysts, and about 10 to 20 embryos are transferred into the uterine horns of (C57BL/6×CBA/Ca) F1 pseudopregnant fosters (Bradley, A., in *Teratocarcinomas and Embryonic Stem Cells: A Practical Approach*, Robertson, E.J., ed., IRL Press, Oxford (1987), pages 113–151). Chimeric males are mated with C57BL/6 or FVB/J females and germline transmission of the mutant allele is verified by Southern blot analysis of tail DNA from F1 offspring with either agouti or gray coat color. F2 offspring from interbred heterozygotes are genotyped by Southern blotting to identify homozygous null mutants.

Drug Screening

In addition to rational design of agonists and antagonists based on the structure of ARF-p19 the present invention further contemplates an alternative method for identifying specific antagonists or agonists and mimics using various screening assays known in the art.

Accordingly any screening technique known in the art can be used to screen for agonists, antagonists or mimics of ARF-p19. The present invention contemplates screens for small molecules (i.e. compounds being less than 3 Kd) or analogs and mimics, as well as screens for natural analogs that bind to and agonize or antagonize ARF-p19 in vivo or mimic the role of ARF-p19 as a tumor suppressor. For example, natural products libraries can be screened using assays of the invention for molecules that agonize, antagonize, or mimic ARF-p19 activity.

Knowledge of the primary sequence of ARF-p19 can also provide clue as the inhibitors, antagonists, or mimics of the protein. Identification and screening of antagonists for example is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry, vol. 5*, Abstract FR:013 (1988); Furka, *Int. J. Peptide Protein Res.*37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for mimics for ARF-p19 according to the present invention.

Alternatively, assays for agents that promote tumor suppression can be performed. The agents can be provided readily as recombinant or synthetic polypeptides, for example.

The screening can be performed with cells that have been designed and/or selected for not expressing ARF-p19. For example, the ability of such cells to undergo apoptosis can be determined in the presence of agents which are contained in a screening library, as described in the foregoing references. The agents can be selected for inducing such apoptosis.

In one example, a phage library call be employed. Phage libraries have been constructed which when infected into host *E. coli* produce random peptide sequences of approximately 10 to 15 amino acids [Parmicy and Smith, *Gene*, 73:305–318 (1988), Scott and Smith, *Science*, 249:386–249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of ARF-p19 containing most or all of the expressed coding region of exon 1β. After a specified incubation period, the filters can be thoroughly washed and developed for autoradiography. Plaques containing the phage that bind to the radioactive ARF-p19 fragment can then be identified. These phages can be further cloned and then retested for their ability to hinder the binding of ARF-p19 to p53, for example. Once the phages have been purified, the binding sequence contained within the phage can be determined by standard DNA sequencing techniques. Once the DNA sequence is known, synthetic peptides can be generated which represent these sequences.

The effective peptide(s) can be synthesized in large quantities for use in in viva models and eventually in humans to act as tumor suppressors. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, Vaccine. 10:175–178 (1990)].

Methods of evaluating the therapeutic or oncogenic potential of compositions: Using the transgenic animals of the invention, it is possible to evaluate a variety of compositions for their therapeutic or oncogenic potential.

1. Generally, methods for determining the therapeutic potential of a composition to treat cancer comprise the step of administering a known dose of the composition to a transgenic animal having a phenotype of reduced or altered ARF-p19 activity, monitoring resulting biological or biochemical parameters correlated with cancer, and comparing the symptoms of treated animals to those of untreated animals.

A first method of assessing the therapeutic potential of a composition using the transgenic animals of the invention comprises the steps of:

(1) Administering a known dose of the composition to a first transgenic animal having a phenotype of reduced or altered ARF-p19 activity;

(2) Detecting the time of onset of cancer in the first transgenic animal; and (3) Comparing the time of onset of cancer in the first transgenic animal to the time of onset of cancer in a second transgenic animal having a phenotype of reduced or altered ARF-p19 activity, which has not been exposed to the composition, wherein a statistically significant decrease in the time of onset of cancer in the first transgenic animal relative to the time of onset of the symptoms in the second transgenic animal indicates the therapeutic potential of the composition for treating cancer.

A second method of assessing the therapeutic potential of a composition using the transgenic animals of the invention comprises the steps of:

(1) Administering a known dose of the composition to a first transgenic animal having a phenotype of reduced or altered ARF-p19 activity, at an initial time, $t_0$;

(2) Determining the extent of cancer in the first transgenic animal at a later time, $t_1$; and (3) Comparing, at $t_1$, the extent of cancer in the first transgenic animal to the extent of neurological symptoms in a second transgenic animal having a phenotype of reduced or altered ARF-p19 activity, which has not been exposed to the composition at $t_0$, wherein a statistically significant decrease in the extent of cancer at $t_1$ in the first transgenic animal relative to the extent of the symptoms at $t_1$ in the second transgenic animal indicates the therapeutic potential of the composition for treating cancer.

A third method of assessing the therapeutic potential of a composition using the transgenic animals of the invention comprises the steps of:

(1) Administering a known dose of the composition to a first transgenic animal having a phenotype of reduced or altered ARF-p19 activity;

(2) Measuring the lifespan of the first transgenic animal; and (3) Comparing the lifespan of the first transgenic animal to the lifespan of a second transgenic animal having a phenotype of reduced or altered ARF-p19 activity, which has not been, exposed to the composition, wherein a statistically significant increase it, the lifespan of the first transgenic animal relative to the lifespan of the second transgenic animal indicates the therapeutic potential of the composition for treating cancer.

2. Generally, methods for determining the potential of a composition to cause or exacerbate cancer comprise the step of administering a known dose of the composition to a transgenic animals having a phenotype of reduced or altered ARF-p19 activity, monitoring resulting biological or biochemical parameters correlated with cancer, and comparing the symptoms of treated animals to those of untreated animals.

A first method of assessing the oncogenic potential of a composition using the transgenic animals of the invention comprises the steps of:

(1) Administering a known dose of the composition to a first transgenic animal having a phenotype of reduced or altered ARF-p19 activity;

(2) Detecting the time of onset of cancer in the first transgenic animal; and (3) Comparing the time of onset of cancer in the first transgenic animal to the time of onset of cancer in a second transgenic animal having a phenotype of reduced or altered ARF-p19 activity, which has not been exposed to the composition, wherein a statistically significant increase in the time of onset of cancer in the first transgenic animal relative to the time of onset of the symptoms in the second transgenic animal indicates the potential of the composition for causing or exacerbating cancer.

A second method of assessing the oncogenic potential of a composition using the transgenic animals of the invention comprises the steps of:

(1) Administering a known dose of the composition to a first transgenic animal having a phenotype of reduced or altered ARF-p19 activity, at an initial time, $t_0$;

(2) Determining the extent of cancer in the first transgenic animal at a later time, $t_1$; and (3) Comparing, at $t_1$, the extent of cancer in the first transgenic animal to the extent of neurological symptoms in a second transgenic animal having a phenotype of reduced or altered ARF-p19 activity, which has not been exposed to the composition at $t_0$, wherein a statistically significant increase in the extent of cancer at $t_1$ in the first transgenic animal relative to the extent of the symptoms at $t_1$ in the second transgenic animal indicates the potential of the composition for causing or exacerbating cancer.

A third method of assessing the oncogenic potential of a composition using the transgenic animals of the invention comprises the steps of:

(1) Administering a known dose of the composition to a first transgenic animal having a phenotype of reduced or altered ARF-p19 activity;

(2) Measuring the lifespan of the first transgenic animal; and (3) Comparing the lifespan of the first transgenic animal to the lifespan of a second transgenic animal having a phenotype of reduced or altered ARF-p19 activity, which has not been exposed to the composition, wherein a statistically significant decrease in the lifespan of the first transgenic animal relative to the lifespan of the second transgenic animal indicates the potential of the composition for causing or exacerbating cancer.

In both of the above sets of methods, the composition may comprise a chemical compound administered by circulatory injection or oral ingestion. The composition being evaluated may alternatively comprise a polypeptide administered by circulatory injection of an isolated or recombinant bacterium or virus that is live or attenuated, wherein the polypeptide is present on the surface of the bacterium or virus prior to injection, or a polypeptide administered by circulatory injection of an isolated or recombinant bacterium or virus capable of reproduction within a mouse, and the polypeptide is produced within a mouse by genetic expression of a DNA sequence encoding the polypeptide. Alternatively, the composition being evaluated may comprise one or more nucleic acids, including a gene from the human genome or a processed RNA transcript thereof.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

The entire text of all publications cited above and below are hereby incorporated by reference.

EXAMPLES

Example 1 cDNA Sequences Encoding ARF-p19

Tandemly linked INK4A (MTS1, CDKN2) and INK4B (MTS2) genes on the short arm of human chromosome 9 encode distinct 16 kDa and 15 kDa inhibitors (InK4a-p16 and InK4b-p15, respectively) of the G1 cyclin D-dependent kinases CDK4 and CDK6 (Serrano et al., *Nature* 366:704–707 (1993); Hannon and Beach, *Nature* 371:257–26 (1994)). Homozygous co-deletion of INK4A and INK4B, hemizygous deletions of INK4A together with point mutations within the remaining allele, and de novo methylation of an CpG island extending into exon 1 of INK4A (Merlo et al., *Nature Med.* 7:686–692 (1995)) are commonly observed in human cancers, suggesting that InK4a-p16, and perhaps InK4b-p15, function as tumor suppressors (Kamb, A. et al., *Science* 264:436–440 (1994); Noburi, T. et al., *Nature* 368:753–756 (1994); Sheaff and Roberts, *Curr. Biol.* 5:28–31 (1994); Hunter and Pines, *Cell* 79:573–582 (1995)). Two other members of the INK4 gene family, InK4c-p18 and INK4d-p19, map to different human chromosomes (Guan et al., *Genes & Develop.* 8:2939–2952 ((1994); Chan et al., *Mol. Cell. Biol.* 15:2682–2688 (1995); Hirai et al., *Mol. Cell. Biol.* 15:2672–2681 (1995); Okuda et al., *Genomics*, 29:623–630 (1995)).

The human INK4A gene yields transcripts that initiate at two promoters, the first (E1α) located in close proximity to other InK4a-p16 coding exons and the second (E1β) mapping centromerically in close proximity to the INK4b gene (Stone, S., et al., *Cancer Res.* 55:2988–2994 (1995); Mao, L., et al., *Cancer Res.* 55:2995–2997 (1995)). A long microsatellite ($CA_N$) repeat downstream of exon 1β is highly polymorphic. The nucleotide sequence of mRNAs derived from exon 1β include a 5'AUG codon which, if used to initiate protein synthesis in fully spliced transcripts, can yield another polypeptide (here designated ARF-p19) derived from a theoretical Alternative Reading Frame that includes most of the exon 2 coding sequences represented in INK4a-p16 mRNA. Two classes of transcripts (α and β, containing 5' sequences derived from exons 1α and 1β, respectively), although virtually identical in length, have been successfully identified by reverse transcription and polymerase chain reactions (RT-PCR) using mRNA templates from a variety of human tissues, but others inferred that the β transcript is unlikely to encode a protein (Stone. S., et al., *Cancer Res.* 55:2988–2994 (1995); Mao, L., et al., *Cancer Res.* 55:2995–2997 (1995)). However, as described herein, mouse exon 1β sequences are spliced to exon 2 of the INK4A gene to generate transcripts encoding a polypeptide that is completely different in amino acid sequence from InK4a-p16.

A mouse erythroleulcemia (MEL) cell DNA library (5' Stretch λgt10, Clontech, Palo Alto, Calif.) was screened with a full-length human InK4a-p16 probe, and twelve hybridizing cDNAs subcloned into pBluescript (Stratagene, La Jolla, Calif.) were sequenced. One cDNA represented mouse InK4a-p16 (Quelle et al., *Oncogene* 11:635–645 (1995)) while the remaining clones, designated ARF-p19, contained alternative sequences derived from exon 1(FIG. 1; SEQ ID NO:1). As confirmed by Southern blotting analysis, the unrelated sequences from the 1α and 1β exons hybridized to distinct genomic DNA fragments.

The mouse β mRNA, which directs the expression of ARF-p19 in a variety of tissues (see Examples 2 to 4), contains an AUG codon at nucleotides 43–45 flanked by Kozak consensus sequences, and translation from this initiator would yield a 169 amino acid polypeptide of 19,349 daltons (ARF-p19; SEQ ID NO:2). Splicing of exon 1β to exon 2 of the INK4A gene occurs at the same acceptor site as that used by exon 1β but changes the exon 2 reading frame to generate an entirely novel protein containing 105 exon 2-derived residues. The mouse and human 1β exons arc conserved in length, except for one additional arginine codon in the human β mRNA located just 5' of the splice donor site. The reading frame (SEQ ID NO:3; FIG. 7) for the human ARF-p19 protein (SEQ ID NO:4) is only 132 codons in length due to a predicted TGA terminator in place of CCA at nucleotides 436–438 (FIG. 1). Mouse and human ARF-p19 polypeptides are 44% identical through their exon 1β segments and 46% identical overall. By comparison, INK4A exon 1α segments are 72% identical, with mouse and human InK4a-p16 proteins sharing 65% overall identity.

The ARF-p19 proteins are highly basic, as indicated by their high arginine content (human, 21% Arg; mouse 22% Arg) and are unrelated to known proteins in searchable databases. However, several known RNA-binding proteins, while not having amino acid sequences that are per se homologous to that of ARF-p19, nonetheless resemble ARF-p19 by having stretches of arginine-rich sequences. Moreover, in at least some instances, these arginine-rich regions have been implicated in the binding of these proteins to specific RNA sequences (Craven, M.G., et al., *J. Bacte-* riol. 176:1394–1404 (1994): Calnan, B.J., et al., *Science* 252:1167–1171 (1991), and erratum, 255:665 (1992)); Lazinski, D., *Cell* 59:207–218 (1989); Tao, J., et al., *Proc. Natl. Acad. Sci. (U.S.A.)* 89:2723–2726 (1992)).

There are precedents for dual utilization of coding sequences in small virus genomes which cannot exceed a complexity that prevents their packaging into virions (Lamb and Horvath, *Trends in Genetics* 7:261–266 (1991); Cullen, *Annu. Rev. Microbiol.* 45:219–250 (1991)). In contrast, eukaryotic genes are composed largely of introns and are more widely spaced, presumably relieving them from evolutionarily imposed size constraints. In *Saccharomyces cerevisiae*, the SNF6 locus and genes encoding certain glycolytic enzymes exhibit overlapping reading frames on opposite strands (Estruch and Carlson, Mol. Cell. Biol. 10:2544–2553 (1990); Boles and Zimmermann, *Mol. Ben. Genet.* 243:363–368 (1994)), whereas the stress response gene, DDR48, includes two overlapping but asyntactie reading frames, each with a capacity to encode a protein of ~45 kDa (Treger and McEntee, *Mol. Cell. Biol.* 10:3174–3184 (1990)). In these cases, however, only one of the two asyntactic reading frames appears to be expressed. Recently, Labarriere et al. (*J. Biol. Chem.* 270:19205–19208 (1995)) reported that transcripts originating from a novel promoter in the human growth hormone (GH) gene have the potential to specify a 107 amino acid protein, the C-terminal half of which arises from a second reading frame in GH exons 1 and 2. Antibodies to the C-terminus of this predicted polypeptide histochemically stained a subpopulation of pituitary cells, arguing for limited focal translation of this mRNA. In general, however, overlapping genes noted as such in the available databases have not been assigned dual protein products. That two INK4A-coded polypeptides can each induce cell cycle arrest, albeit at different points in the cycle and via apparently distinct mechanisms (see Example 5), suggests that their unitary inheritance has functional significance.

It is noteworthy that alternative splicing of transcripts from another cell cycle-controlling gene, that encoding integrin $b_1$, produces a second gene product, $b_{1C}$, that also functions to regulate cell cycle arrest (Merdith et al., *Science* 269:1570–1572 (1995)). However, unlike ARF-p19 and InK4a-p16. the integrin $b_1$ and $b_{1C}$ reading frames overlap syntactically rather than asyntactically. Specifically, $b_{1C}$ contains a carboxyl-terminal 48-amino acid sequence that replaces the carboxyl-terminal 21 amino acids found in $b_1$; otherwise, however, the sequences of the two proteins are identical. If alternative splicing of RNA transcripts is a recurring motif of cell cycle gene expression then, conceivably, a limited number of common RNA splicing factors could affect the expression of many proteins involved in the regulation of progression through the cell cycle.

Example 2

ARF-p19 is Expressed in Mouse Cells and Tissues

In a survey of mouse tissues and cells lines α and β mRNAs of similar length (~1 kb) were detected by Northern blotting with specific exon 1α and exon 1β probes and, in agreement, by RT-PCR using specific 5' primers (FIG. 2).

For RT-PCR Analysis, polyadenylated mRNA was prepared from tissues excised from normal female mice (C31/ HEJ, Jackson Laboratories, Bar Harbor, Me.), and cDNA was synthesized from 50 ng of polyA mRNA templates according to manufacturer's instructions (StrataScript RT-PCR Kit, Stratagene) (Quelle et al., *Oncogene* 11:635–645 (1995)). PCR amplification of either mouse ARF-p19 β transcripts, or of InK4a-p16 a transcripts, was performed using a common antisense primer having the sequence

5'-GCAAAGCTTGAGGCCGGATTTAGCTCTC    SEQ ID NO:5 and either an ARF-p19 specific sense primer having the sequence

5'-AGGGATCCTTGGTCACTGTGAGGATTC    SEQ ID NO:6 or an InK4a-p16 specific sense primer having the sequence

5'-CGGGATCCGCTGCAGACAGACTGGCCAG    SEQ ID NO:7 with 35 cycles of denaturation (95° C., 1 min), annealing (65° C., 45 sec), and extension (72° C., 2 min). Products (~0.5 kb, 10 µl per lane) were electrophoresed on 1.5% agarose gels and blotted onto nylon membranes (Hybond N, Amersham, Arlington Heights, Ill.). $^{32}$P-labeled probes which specifically recognized exon 1β (ARF-p19, bases 1–228 of SEQ ID NO:1), exon 1α (InK4a-p16, bases 58–182), or an antisense oligonucleotide derived from exon 2 and having the sequence

5'-CGTCTAGAGCGTGTCCAGGAAGCCTTCC    SEQ ID NO:8 were hybridized at 50° C. in neutral pH buffer containing 0.9M NaCl and washed in 0.015M NaCl, 0.1% SDS at the same temperature.

Figure 2B:
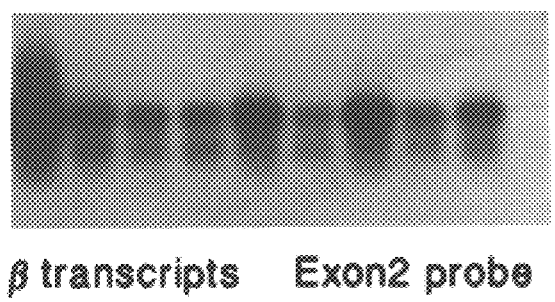
Figure 2C:
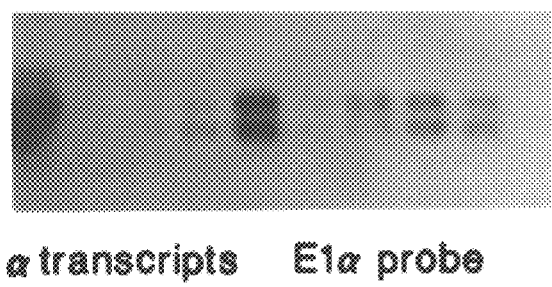
Figure 2D:
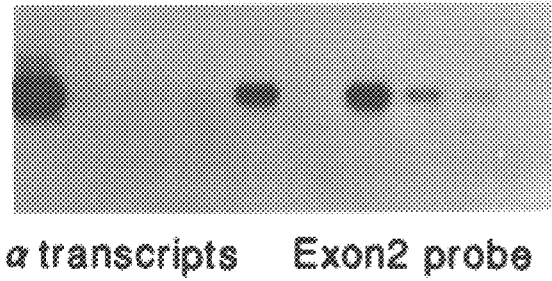

Specific amplification of β transcripts and hybridization of the products with exon 1β (FIG. 2(A)) and exon 2 (FIG. 2(B)) probes revealed their ubiquitous expression in various organs. The signal was particularly high using mRNA templates from MEL, cells from which both α and β cDNAs have been cloned. By contrast, a mRNAs encoding INK4a-p16 were expressed at relatively high levels in only few tissues (Quelle et al., *Oncogene* 1:635–645 (1995)), and the more restricted patterns of hybridization observed with the exon 1α and exon 2 probes confirmed the specificity of the PCR primers (FIGS. 2(C) and 2(D)). Importantly, amplified a transcripts generated no signal at all after hybridization with the exon 1β probe and vice versa, and no products were obtained in the absence of mRNA templates (FIG. 2). ARF-p19-encoding β transcripts were also detected in other cell lines, including CTLL-2 and RL-12 T cells, and NFS112 B cells, but were absent from NIH-3T3 fibroblasts and BAC1.2F5 macrophages, both of which have sustained deletions of the INK4A locus (data not shown).

Examples 3

Antibodies to ARF-p19 and Detection of ARF-p19 Proteins

An antiserum directed to the unique carboxy-terminal amino acid sequences was generated using a synthetic, conjugated carboxy terminal oligopeptide derived from the ARF-p19 protein using techniques previously described for InK4a-p16-derived oligopeptides (Quelle et al., *Oncogene* 11:635–645 (1995)). Specifically, a synthetic peptide having the sequence (SEQ ID NO:9):

NH$_2$-Val-Phe-Val-Tyr-Arg-Trp-Glu-Arg-Arg-Pro-Asp-Arg-Arg-Ala corresponding to residues 156–169 of murine ARF-p19 protein (SEQ ID NO:2) was used.

The antibody to ARF-p19 carboxy-terminal sequences encoded by the β mRNA precipitated a protein with an apparent molecular mass of about 22 kDa (i.e., ARF-p19) after transcription and translation of the β cDNA in vitro (FIG. 3, lane 8). There is no evidence that ARF-p19 undergoes post-translational modification(s) in viva that detectably alter its mobility on denaturing gels (see Example 4), so the apparent disparity between the masses of the predicted and translated proteins likely reflect the unusual amino acid composition of ARF-p19 (FIG. 1). An antiserum to the C-terminus of mouse InK4a-p16 detected the cognate protein (FIG. 3, lane 6) but did not cross-react with ARF-p19 (FIG. 3, lane 9).

Sequences encoding a hemagglutinin (HA) epitope tag were added to the 5' end of the ARF-p19 cDNA by polymerase chain reaction (PCR) using a forward primer containing a 5' BamHI site (underlined) having the sequence (SEQ ID NO:10):

5'- CGGGATCCGAATTCAGCCATGGGTTACCCATACGACG-
TCCCAGACTACGCTACCGGTCGCAGGTTCTTGGTCAC and a reverse primer extending over the single BssHII site (underlined) in exon 1β having the sequence of the reverse complement of residues 68–87 of SEQ ID NO:1, i.e.,

5'-GCCCGCGCGCTGAATCCTCA          SEQ ID NO: 11

The PCR product was digested with BamHI and BssHII, subcloned into the original cDNA in pBluescript, and resequenced. The resultant ARF-p19 fusion protein, in which the amino terminus of ARF-p19 is tagged with a hemagglutinin (HA) epitope, has a mobility that is slightly retarded compared to that of wild-type ARF-p19 (FIG. 3, lane 2). The HA-tagged ARF-p19 protein could be detected with anti-HA serum (see below).

Figure 4A:
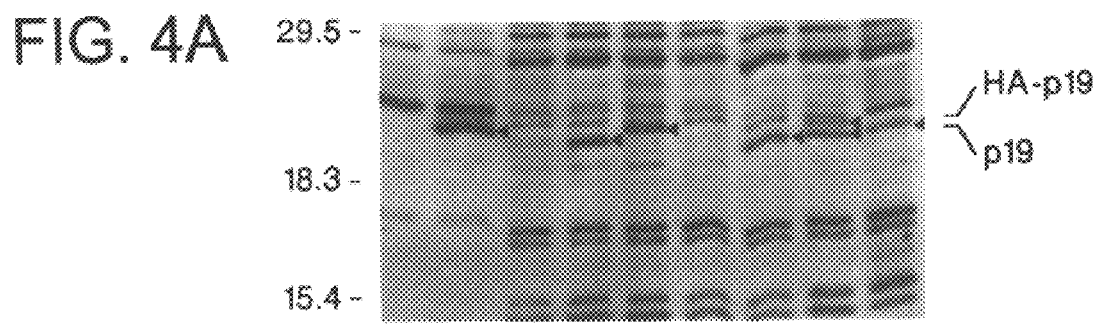

The endogenous ARF-p19 protein could also be detected in lysates of mouse MEL cells (FIG. 4(A), lane 9, arrow), which synthesize high levels of both α and β mRNAs (FIG. 2). Protein InK4a-p16, expressed in MEL cells (FIG. 4(C), lane 9), was not detected with antiserum to ARF-p19, nor vice versa (compare FIGS. 4(A) and 4(C)), confirming the specificity of the antisera and indicating as well that an N-terminally truncated InK4a-p16 protein, which would have carboxylterminal ARF-p19 sequences, does not normally arise by initiation from internal AUG codons within the β mRNA.

In cytospins prepared from cells harvested 48 hours after infection with viruses encoding HA-tagged ARF-p19, immunofluorescence using detectably labeled antibodies to the ARF-p19 C-terminus (FIG. 5(A)) or to the aminoterminal HA epitope (FIG. 5(C)) demonstrate that both untagged and HA-tagged ARF-p19 localize to the cell nucleus. This reflects the strictly nuclear localization of wild-type ARF-p19, which is normally expressed in derivatives of Balb/c fibroblasts (data not shown).

Example 4

Production of Recombinant ARF-p19 Native and Fusion Proteins

Baculoviral Expression in Insect Sf9 Cells

For expression in insect Sf9 cells (Kato et al., *Genes & Devel.* 7:331–342 (1993)), an EcoRI fragment encoding tagged ARF-p19 was inserted into the pVL1393 baculovirus vector (Pharmingen, San Diego, Calif.). Insect Sf9 cells were infected and harvested as previously described (Kato et al., *Genes & Devel.* 7:331–342 (1993); see also Richardson, C.D., ed., *Baculovirus Expression Protocols*, Methods in Molecular Biology vol. 39, Walker, J.M., series ed., Humana Press, Totowa, New Jersey (1995), Chapters 1–5 and 11).

Figure 4B:
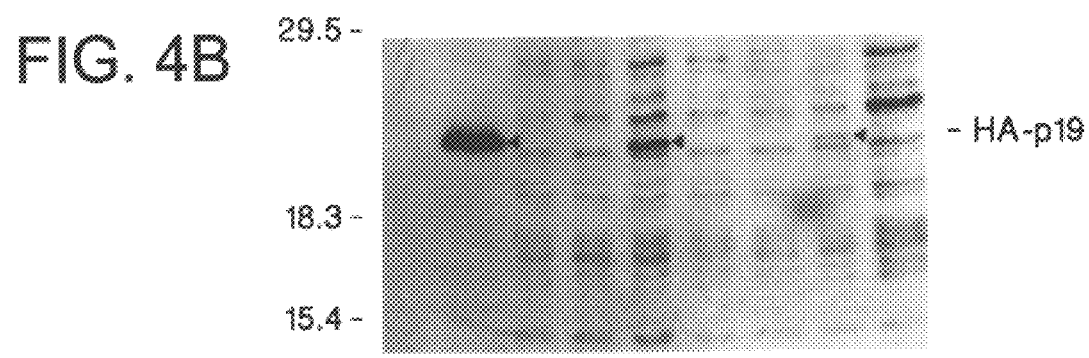

When the cDNA encoding HA-tagged ARF-p19 was expressed under baculoviral control in insect Sf9 cells, a protein of slightly slower mobility than that of the endogenous protein in MEL cells was detected with antibody to ARF-p19 (FIG. 4(A), lane 2) or to the hemagglutinin (HA) tag (FIG. 4(B), lane 2).

Virus Production and Infection of Mammalian Cells

Both untagged and HA-tagged ARF-p19 cDNAs were subcloned into the EcoRI site of the SRα-MSV-tk-neo retroviral vector (Muller et al., *Mol. Cell. Biol.* 11:1785–1792 (1994)) for production of virus. Human kidney 293T cells were transfected with 15 μg ecotropic helper virus DNA plus 15 μg SRα vector DNA using a modified calcium phosphate precipitation technique (Chen and Okayama, *Mol. Cell. Biol.* 7:2745–2752 (1987)). Cell supernatants containing infectious retroviral pseudotypes were harvested 24–60 hours post-transfection, pooled on ice, and filter (0.45μ) sterilized. Virus infections of exponentially growing mouse fibroblasts in 100 mm diameter culture dishes were performed at 37° C. in a 4% $CO_2$ atmosphere using 2 ml virus-containing supernatants containing 8 μg/ml polybrene (Sigma, St. Louis, Mo.). After 3 hours, 10 ml fresh medium was added. Cells were harvested 48 hours after infection and their DNA content was analyzed by flow cytometry (Matsushime et al., *Cell* 65:701–703 (1991)).

Mammalian cell lines were maintained in Dulbecco's modified Eagle's medium (DMEM) supplemented with 10% fetal bovine serum, 2 mM glutamine, and 100 units/ml penicillin and streptomycin (Gibeo, Grand Island, N.Y.). NIH-3T3 cells ($Rb^+$, $INK4A^-$, p53 status uncertain) were transfected with vectors encoding D-type cyclins alone or with CDK4, and polyclonal populations derived from pooled, drug resistant transformants were used (Quelle et al., *Genes & Devel.* 7:1559–1571 (1993)). Derivatives of Balb-3T3 cells (Rb status uncertain, $INK4a-p16^+$, $p53^-$) were provided by G. Zambetti (St. Jude Children's Research Hospital), and the 293T retrovirus packaging line (Pear et al., *Proc. Natl. Acad. Sci. USA* 90:8392–8396 (1993)) was obtained from Charles Sawyers (UCLA) with permission from David Baltimore (MIT).

For analysis of ARF-p19 or InK4a-p16 expression, pelleted mammalian cells were disrupted in ice-cold cell lysis buffer ($1 \times 10^7$ cells/ml) for 1 hour on ice. Nuclei and debris were removed by centrifugation in a microfuge at 12,000 rpm for 10 min at 4° C. Supernatants were boiled in gel loading buffer, and proteins ($2 \times 10^5$ cell equivalents per lane) were separated on denaturing gels as above and transferred onto nitrocellulose (Quelle et al., *Genes & Devel.* 7:1559–1571 (1993)). Proteins were detected by enhanced chemiluminescence (ECL, Amersham) according to manufacturer's specifications with ARF-p19 or InK4a-p16 antisera or with 12CA5 monoclonal antibody to the HA tag (ICN, Costa Mesa, Calif.). Assays for CDC2 and CDK2-associated histone H1 kinase activity were performed as previously described (Matsushime et al., *Cell* 71:323–334 (1992)). In some experiments, specifically immunoprecipitated CDKs or cyclins were separated on denaturing gels and immunoblotted with anti-ARF-p19 as above.

Figure 4C:
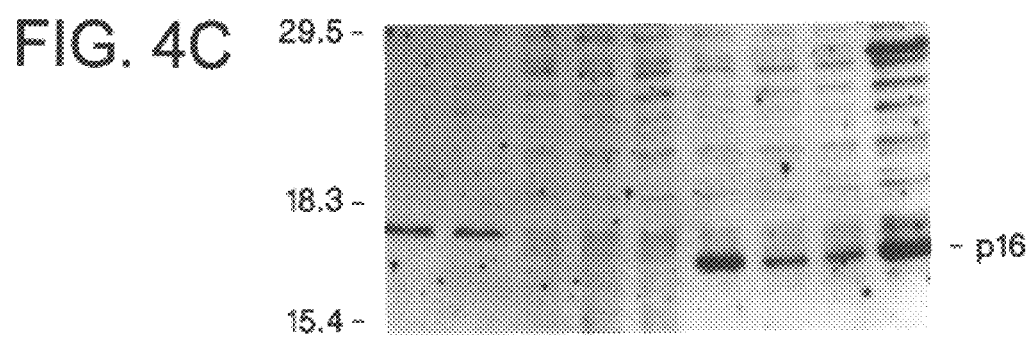

Infection of INK4-negative NIH-3T3 cells engineered to overexpress cyclin D1 with a retrovirus containing the β cDNA led to ectopic ARF-p19 synthesis (FIG. 4A, lane 4). When the HA-tagged ARF-p19 protein was introduced, the polypeptide again migrated with a slightly slower mobility than the wild-type protein (FIG. 4A, lane 5 versus 4) and was also revealed with anti-HA serum (FIG. 4B, lane 5). Unlike NIH-3T3 cells which lack the INK4A gene and do not express ARF-p19 (FIG. 4A, lane 3) or InK4a-p16 (FIG. 4C, lanes 3–5), derivatives of Balb-3T3 cells synthesize both proteins (FIGS. 4A and 4C, lanes 7 and 8). Therefore, the β transcript encodes an authentic ARF-p19 protein which is coexpressed with InK4a-p16 in MEL and Balb-3T3-derived cell lines.

Example 5

Induction of Cell Cycle Arrest by ARF-p19

In the experiments shown in FIG. 4, the DNA content of cells expressing ARF-p19 was concomitantly measured in order to assess the effect(s) of ARF-p19 on the cell cycle. Surprisingly, infection of NIH-3T3 cells for 48 hours with retroviruses encoding ARF-p19 induced cell cycle arrest in both the G1 (2N DNA content) and G2/M (4N DNA content) phases of the cell cycle with a proportional loss of cells in S phase (DNA content between 2N and 4N) (Table 1). Cells infected with the empty vector were distributed throughout the cycle in a manner indistinguishable from uninfected cells. In similar experiments performed with cells engineered to overexpress cyclin D1, a greater proportion of ARF-p19 expressing cells arrested in G2/M versus G1 (Table 1). Proliferating cyclin D1 overexpressors have a 20–30% contracted G1 phase interval and a compensatory shortening of their doubling time, so that their overall cell cycle distribution is unchanged (Quelle et al., *Genes & Devel.* 7:1559–1571 (1993)). However, the relative increase in the (G2/M versus the G1 phase fraction suggests that cyclin D1 overexpression partially overcomes the p19-induced G1 block.

TABLE 1

Cell Cycle Arrest by ARF-p19

| Cell Line<br>(No. Expts) | Vector<br>cDNA Insert | Cell Cycle Distribution<br>(48 hrs post-infection) | | |
|---|---|---|---|---|
| | | % G$_0$/G1 | % S | % G2/M |
| NIH-3T3 (7) | None | 42.4 ± 3.3 | 42.0 ± 2.3 | 15.6 ± 3.3 |
| NIH-3T3 (8) | p19$^{ARF}$ | 66.6 ± 5.2 | 12.5 ± 2.6 | 20.9 ± 5.1 |
| 3T3-D1 (8) | None | 41.1 ± 6.6 | 39.1 ± 4.4 | 19.8 ± 2.7 |
| 3T3-D1 (9) | p19$^{ARF}$ | 53.0 ± 4.3 | 11.6 ± 2.8 | 35.4 ± 4.2 |
| BALB-3T3 (3) | None | 36.5 ± 8.9 | 49.0 ± 8.8 | 14.5 ± 1.2 |
| BALB-3T3 (3) | p19$^{ARF}$ | 57.1 ± 4.9 | 26.0 ± 2.8 | 16.9 ± 1.4 |

In these experiments, the DNA content of NIH-3T3 cells infected for 48 hours with a control vector or with retroviruses encoding ARF-p19 was determined by FACS analysis. Proliferating polyclonal derivatives overexpressing cyclin D1 (3T3-D1) are not redistributed though the cell cycle, because the shortening of their G1 phase by 20–30% is compensated by a reduced generation time (Quelled et al., *Genes &. Devel.* 7:1559–1571 (1993)). ARF-p19-induced G2 → M arrest in all cyclin D overexpressors was more marked than in parental cells. Arrested cells were fully viable, lacked metaphases, and contained intact nuclei (FIG. 5), features all indicative of arrest in interphase.

Infection of NIH-3T3 or 3T3-D1 overexpressors with retroviruses expressing InK4a-p16 or InK4d-p19 leads only to G1 phase arrest (Hirai et al., *Mol. Cell. Biol.* 15:2672–2681 (1995); Quelle et al., *Oncogene* 11:635–645 (1995)). The fact that a significant proportion of cells ectopically expressing ARF-p19 accumulate in G2/M suggests that the action of the ARF-p19 protein is not limited to effects relating to InK4a-p16 activity.

The phenotype of the ARF-p19 expressors was unusual in that many of the infected NIH-3T3 cells appeared rounded and highly refractile, superficially similar to those in mitosis. However, cells enforced to express ARF-p19 exhibited only a minor (<0.2%) metaphase fraction compared to cells infected with the vector control (~3%). Nor did the cells undergo apoptosis, as determined by the following sensitive flow cytometric assay and by their lack of DNA fragmentation.

Apoptosis Assay

Trypsinized cell suspensions were washed and suspended in 0.5 ml PBS and pipetted dropwise into 5 ml of 1% buffered paraformaldehyde on ice with gentle mechanical mixing. After 15 min incubation on ice, cells were pelleted, washed with 10 ml cold PBS, and the pellets were resuspended in 1 ml 70& ethanol pre-cooled at −20° C. Samples stored at −20° C. overnight were resuspended, divided into two equal aliquots, collected by centrifugation, and washed twice with ice cold PBS. Duplicate samples were resuspended in 50 μl reaction mixtures containing 1x terminal deoxynucleotidyl transferase (TdT) buffer, CoCl$_2$, and digoxigenin-11-UTP with or without 0.5 μl TdT (all supplied as a TdT kit by Boehringer Mannheim Corp., Indianapolis, Ill.). After 30 min incubation at 37° C., 1 ml of ice cold PBS was added, and recentrifuged cells were suspended in 100 μl of a 1:40 dilution in PBS of anti-digoxigenin-FITC monoclonal antibody and incubated for 30 minutes in the dark at room temperature. Cells were sequentially washed in 1 ml of ice cold PBS containing 2 mM sodium azide and 0.35% bovine serum albumin (BSA), and then in 1 ml 0.1% Triton X-100 in PBS, and resuspended in 1 ml PBS-azide-BSA containing 50 μg/ml propidum iodide. RNAse (50 μg/ml) was added, and after 30 minute incubation at room temperature, samples were filtered for flow cytometry and analyzed for DNA content (red PI fluorescence) and TdT-labeled DNA fragments (green FITC) on a Becton Dickinson FACScan (Matsushime et al., 1991). DNA fragmentation was quantitated by deteimining the difference in FITC fluorescence between duplicate samples incubated with and without TdT. Human Jurkat T cells treated with 100 μM etoposide for 6 hrs were routinely included as positive controls for cells undergoing apoptosis.

Immunofluorescence

Cells were harvested 48 hours after infection and spun onto glass slides (5×10$^4$ cells/slide) using a Scimetrics Cytospin3 at 500 rpm for 5 min. Following fixation for 10 min at room temp in 3% paraformaldehyde, slides were washed 3 times with phosphate-buffered saline (PBS), permeabilized in 0.2% Triton X-100 for 10 min at room temperature, and washed 3 more times with PBS. After 30 min incubation in blocking solution (PBS containing 1% dry milk), cells were incubated at room temperature in a humidified chamber for 1 hour with primary antibody (5 μg/ml 12CAS MAb or 1:600 ARF-p19 polyclonal antiserum diluted in blocking solution). To confirm the specificity of ARF-p19 antiserum, primary antibody was incubated with ARF-p19 peptide for 1 hour at temperature prior to incubation with cells. After six washes with blocking solution, secondary antibody incubations were performed in blocking solution for 30 min, using 1:50 dilutions of either FITC-conjugated sheep anti-mouse or FITC-conjugated donkey anti-rabbit IgG (Amersham, Arlington Heights, Ill.). After six washes with PBS, cells were stained with Hoescht dye 33258 (1 μg/ml), wet mounted with vectashield medium (Vector, Burlingame, Calif.), and photographed at 600X magnification through a microscope equipped with epifluorescence optic (Olympus, Lake Success, N.Y.).

When cytospins were prepared from cells harvested 48 hours after infection with viruses encoding HA-tagged ARF-p19, immunofluorescence performed with antibodies to the ARF-p19 C-terminus (FIG. 5(A)) or to the N-terminal HA epitope (FIG. 5(C)) revealed the protein in the cell nucleus. Greater than 80% of the infected cells stained brightly compared to uninfected cells (not shown) or to those stained with peptide blocked serum (FIG. 5(B)). No nuclear dissolution or mitotic figures were observed, continuing that the cells arrested in interphase.

Example 6

Effects of ARF-p19 on CDK Activity

When lysates of ARF-p19-infected NIH-3T3 cells were precipitated with specific antisera to CDC2 or CDK2 and histone H1 kinase activity was measured in immune complexes, the activities of both CDKs were greatly reduced relative to proliferating populations infected with the control vector (data not shown). The observed ~10-fold decrease in CDC2 kinase is consistent with the loss of the mitotic fraction, whereas the ~5 fold drop in CDK2 activity likely reflects a redistribution of cells from S phase into G1 and G2. Indeed, given the dissimilarity in structure between ARF-p19 and known CDK inhibitors, it seems unlikely that the protein interacts directly with CDKs or cyclins. In agreement, when CDC2, CDK2, CDK4, CDK6, cyclins D1, D2, E, and A immunoprecipitates from NML cell lysates were blotted with anti-ARF-p19, no coprecipitation of ARF-p19 was observed. Reconstruction experiments with baculovirus expression vectors in insect Sf9 cells also failed to provide convincing evidence for associations between ARF-p19 and these cell cycle regulators. The mechanism(s) by which ARF-19 induces cell cycle attest remains unclear, although the propensity of some cells to arrest in G2 argues that these ARF-p19-induced effects are pRb-independent.

Example 7

ARF-p19 Mutations in Human Cancers

Current evidence indicates that InK4a-p16 functions upstream of cyclin D-dependent kinases and pRb in a biochemical pathway that regulates exit of G1 phase cells into S phase. InK4a-p16 cannot induce G1 rest in cells that lack pRb function (Guan et al., Genes & Devel. 8:2932–2952 (1994); Tam et al., Oncogene 9:2663–2674 (1994); Lukas et al., Nature 375:503–506 (1995); Medema et al., Proc. Natl. Acad. Sci. USA 92:6289–6293 (1995); Koh et al., Nature 375:506–510 (1995)), and in lung cancer, INK4A deletions are restricted to tumors that retain pRb activity and vice versa, implying that a loss of either gene makes compromise of the other irrelevant (Otterson et al., Oncogene 9:3375–3378 (1994)). Increased levels of InK4a-p16 are generally observed in pRb-negative tumor cells (Serrano et al., Nature 366:704–707 (1993); Bates et al., Oncogene 9:1633–1640 (1994); Lukas et al., J. Cell. Biol. 125:625–638 (1994); Tam et al., Oncogene 9:2663–2674 (1994)), suggesting that InK4a-p16 expression may be somehow governed by pRb itself or, alternatively, that pRb provides a predisposing selective pressure that favors elimination of pRb-mediated controls (Sherr and Roberts, Genes Devel. 9:1149–1163 (1995)).

Of the numerous InK4a-p16 mutations found in human cancers, only a few have been experimentally evaluated for effects on the cell cycle. However, two which clearly abrogate InK4a-p16 inhibitory functions (R87P and H98P in Koh et al., Nature 375:506–510 (1995)) are silent with regard to ARF-p19, and another (P114L in Lukas et al., Nature 375:503–506 (1995)) falls outside the region of overlap between InK4a-p16 and ARF-p19, indicating that the latter is not a target of inactivating mutations in these cases.

Nevertheless, most mutations involving INK4A in cancer cells fall within the 5' half of exon 2, raising the possibility that some may dually affect InK4a-p16 and ARF-p19 or, conceivably, ARF-p19 alone. About 60% of mutations in InK4a-p16 cluster within the region overlapping ARF-p19 (Hirama and Koeffler, Blood 86:841–854 (1995)), and more than 80% of these affect ARF-p19 primary structure. FIG. 6 shows the predicted ARF-p19 mutations within this segment, compiled from data obtained with primary tumors, xenogratts, and established cell lines (Kamb, A. et al., Science 264:436–440 (1994a), Nature Genet 8:22–26 (1994b); Caldas et al., Nature Genet. 8:27–32 (1994); Hussussian et al., Nature Genet. 8:15–21 (1994); Ohta et al., Cancer Res 54:5269–5272 (1994); Zhang et al., Cancer Res 54:5050–5053 (1994); Mori et al., Cancer Res. 54:3396–3397 (1994); Hayashi et al., Biochem. Biophys. Res. Commun. 202:1426–1430 (1994)). Of 50 missense and frame shift mutations, 39 involve codons conserved between human and mouse ARF-p19 (residues in hold type) and four (marked by asterisks) are silent InK4a-p16. The most frequently mutated ARF-p19 residues in sporadic cancers are Gly-69, Pro-94, Arg-98, each of which is conserved in humans and mice, and the most common disease-related alteration in melanoma kindreds (Hussussian et al., Nature Genet. 8:15–21 (1994); Kamb et al., Nature Genet. 8:22–26 (1994b)) converts conserved Arg-115 of ARF-p19 to Leu. A further complication is that frame shift mutations have the potential to produce chimeric proteins. For example, those involving ARF-p19 Gln-70 (Hayashi et al., Biochem. Biophys. Res Commun. 202:1426–1430 (1994)) and Gly-74 (Ohta et al., Cancer Res. 54:5269–5272 (1994)) should result in INK4A α transcripts encoding InK4a-p16/ARF-p19 fusions in which the majority of exon-2 sequences encode ARF-p19 residues. Conversely, an ARF-p19 frame shift involving Gly-102 (Hayashi et al., Biochem. Biophys. Res Commun. 202:1426–1430 (1994)) would yield a b transcript encoding the C-terminal half of InK4a-p16. To the extent that mutations in ARF-p19 contribute to aberrant growth control and tumorigenesis, detection and analysis of ARF-p19-specific nucleic acids (Example 2) in a mammal serves to diagnose, or assist in the diagnosis of, existing tumors in the mammal, or to predict the mammal's predisposition for developing certain forms of cancer.

Example 8

Tumor Suppression at the Mouse INK4a Locus Mediated by the Alternative Reading Frame Product p19$^{ARF}$ Introduction The two most frequently inactivated tumor suppressor genes in human cancer, irrespective of tumor type, site, and patient age, are p53 and INK4a [Hall and Peters, Adv. Cancer Res., 68:67–108 (1996); Hainaut et al., Nucleic Acid. Res., 25:151–157 (1997)]. The INK4a locus encodes p16$^{INK4a}$, a specific inhibitor of the cyclin D-dependent kinases CDK4 and CDK6 [Serrano et al., Nature, 366:704–707 (1993)], which antagonizes their ability to phosphorylate the retinoblastoma protein (Rb) and so prevents exit from G1 phase. Genetic disruption of the p16$^{INK4a}$—cyclin D-dependent kinase—Rb pathway is a common event in the life history of cancer cells, which is achieved either through inactivation of the tumor suppressors (p16$^{INK4a}$, Rb) or by uncontrolled overexpression of the proto-oncogenes (D-type cyclins, CDK4) [Hunter and Pines, Cell, 79:573–582 (1994); Weinberg, Cell, 81:323–330 (1995): Hall and Peters, Adv. Cancer Res., 68:67–108 (1996); Sherr, Science, 274:1672–1677 (1996)]. Concurrent inactivation of p53 function inhibits such cells from arresting in G1 phase following DNA damage, decreases their genomic stability, and prevents them from undergoing apoptosis [Gottlieb and Oren, Biochem. Biophys. Acta, 1287:77–102 (1996); Ko and Prives, Genes Dev., 10:1054–1072 (1996); Leving, Cell. 88:323–331 (1997)], thereby collaborating with Rb loss-of-function in tumor cell progression.

A complication stems from the fact that the INK4a locus encodes a second alternative reading frame (ARF) protein whose enforced expression can also induce cell cycle arrest [Quelle et al., Cell, 83:993–1000 (1995b)]. While p16$^{INK4a}$ is specified three exons (designated 1α, 2, and 3), an alternative first exon (1β) maps ~13 kb 5' to exon-1α in the mouse genome, and its coding sequences are spliced to the identical acceptor site of INK4a exon-2. The resulting mRNA specifies a p19$^{ARF}$ protein of 169 amino acids, 65 encoded by exon-1β and the remainder by a second reading frame in exon-2. p19$^{ARF}$ shares no amino acid homology with p16$^{INK4a}$ or other known proteins, and apart from being a highly basic protein that localizes to nuclear speckles during interphase, its function remains unknown. Unlike p16$^{INK4a}$, p19$^{ARF}$ overexpression induces both G1 and G2 phase arrest in rodent fibroblasts, whether or not the cells retain INK4a. The unusual organization of the INK4a locus is conserved in humans [Duro et al., Oncogene, 11:21–29 (1995); Mao et al., Cancer Res., 55:1995–2997 (1995); Stone et al., Cancer Res., 55:2988–2994 (1995)] and rats [Swafford et al., Mol. Cell. Biol., 17:1366–1374 (1997)], whereas three related but distinct INK4 genes do not encode analogous ARF proteins.

Disruption of INK4a exon-2 in mice predisposes young animals to tumor development [Serrano et al., Cell, 85:27–37 (1996)]. Their cultured mouse embryo fibroblasts (MEFs) fail to undergo a senescence crisis and can be transformed by oncogenic ras alleles, which, in the absence of collaborating "immortalizing oncogenes", would otherwise induce growth arrest [Lloyd et al., Genes Dev., 11:663–667 (1997); Serrano et al., Cell, 88:593–602 (1997)]. Although it was clear that elimination of exon-2 of INK4a would compromise expression of both p16$^{INK4a}$ and p19$^{ARF}$, it has been widely assumed that the observed phenotype stemmed from p16$^{INK4a}$ disruption alone. ARF function has been selectively disrupted herein in mice by deleting exon-1β and leaving all p16$^{INK4a}$ coding sequences intact.

Experimental Procedures

Targeting vector: Bacteriophages containing ARF exon 1β were isolated from a 129/SvjE mouse genomic library [Van Deursen et al., Proc. Natl. Acad. Sci. USA, 92:7376–7380 (1995)] using p19$^{ARF}$-specific cDNA probes [Quelle et al., Cell, 83:993–1000 (1995b)]. Restriction enzyme maps of the INK4a and INK4b loci were determined using bacterial artificial chromosome (BAC) clones (Genome Systems, St. Louis Mo.). To construct the targeting vector, a kb SmaI fragment containing Exon 1β was deleted and replaced with a neo cassette flanked by 2.5 kb EcoRI (E) to SmaI (Sm) and 5 kb SmaI to SpeI(S) fragments derived from the ARF locus; screening of ES cell clones was performed by digestion of genomic DNA with AflII (FIG. 8A).

Homologous recombination and generation of germline chimeras: ES cells (RW4, Genome Systems, St. Louis Mo.) were electroporated with 10 μg of linearized targeting vector and selected with geneticin (G418, Sigma Chemicals, St. Louis Mo.) and 1-[2'-deoxy-2'fluoro-β-D-arabinofuranosyl]-5-iodouracil (FIAU; Bristol-Myers Squibb, Princeton N.J.) [Van Deursen et al., Proc. Natl. Acad. Sci, USA, 92:7376–7380 (1995)]. Three hundred ES colonies doubly resistant to G418 and FIAU were analyzed for homologous recombination using AflII and a 1.0 kb SpeI-ClaI probe (FIG. 8A). Four ES clones heterozygous for exon 1β were injected into C57B1/6 blastocysts, which were subsequently implanted into the uteri of pseudopregnant F1 B/CBA foster mothers and allowed to develop to term. Male chimeras from two clones selected by agouti coat color were mated to C57B1/6 females. Germline transmission was obtained with one clone. F1 animals were tested for the presence of the deleted ARF locus by Southern blotting of tail DNA and heinizygous F1 males and females were interbred to generate F2 littermates taken for subsequent studies.

Cells and culture conditions: Cells were maintained in Dulbecco's modified Eagle's medium (DMEM) supplemented with 10% feral bovine serum (FBS), 2 mM glutamine, and 100 U/ml penicillin and streptomycin (GIBCO, Grand Island N.Y.). Balb-313 (10)1 and (10)3 derivatives (INK4a$^+$, p53-deleted) were provided by G. Zambetti (St. Jude Children's Research Hospital); mouse erythroleukemia (MEL) cells (p53-null, INK4a$^+$) were from Drs. P. Marks and V. Richion (Memorial Sloan-Kettering Institute, New York N.Y.). Four previously established MEF cell lines included 5–9, 5–10, and 6–14 (INK4$^+$, p53 mutant plus wild-type) and line 6–18 (INK4a$^-$, p53 wild-type) [Zindy et al., Oncogene, 15:203–211 (1997)]. The 293T retrovirus packaging line and helper virus plasmid [Pear et al., Proc. Natl. Acad. Sci. USA, 90:8392–8396 (1993)] were obtained from C. Sawyers (University of California, Los Angeles) with permission from David Baltimore (Massachusetts Institute of Technology).

MEFs were derived from 13.5 day old embryos using a 3T9 protocol based on a strategy of Todaro and Green. Following removal of the head and organs, embryos were rinsed with phosphate-buffered saline (PBS), minced, and digested with trypsin (0.05% solution containing 0.53 mM EDTA) for 10 min at 37° C., using 1 ml per embryo. Trypsin was inactivated by addition of DMEM containing 10% FBS and 2 mM glutamine, 0.1 mM MEM non-essential amino acids, 55 μM 2-mercaptoethanol, and 10 μg/ml gentamycin. Cells from single embryos were plated into two 60 mm diameter culture dishes and incubated at 37° C. in a 10% $CO_2$ humidified chamber. Cells were maintained on a defined schedule (9×10$^5$ cells per 60 mm diameter dish passaged every 3 days). Plating after disaggregation of embryo cells was considered passage 1, and the first replating three days later as passage 2. Growth curves at passages 5 and 10 were initiated with replicate cultures of 2×10$^4$ cells per 60 mm diameter dish; duplicate cultures were counted daily thereafter.

Focus Formation Assay: MEF cells at passages 6 to 8 were seeded at 3×10$^5$ cells per 35 mm diameter plate and cultured overnight in complete medium containing 10% FBS. Transfections were performed with SuperFeet reagents (Qiagen, Santa Clara, Calif.) per manufacturer's instructions. Expression vector plasmid DNAs, pDCR and pDCR-rasV12 (Michael A. White, Southwestern Medical Center, Dallas Tex.) were mixed with a vector encoding β-galactosidase, and complex formation with SuperFeet reagent was performed. After 5 hours of incubation of duplicate cultures with DNA complexes cells were washed once with PBS and transferred into complete medium containing 10% PBS for 2 days. One plate was used for detection of β-galactosidase-positive cells in order to estimate transfection efficiency. Cells from the other plate were distributed equally into three 60 mm diameter culture dishes, grown in complete medium containing 5% FBS, and refed with fresh medium every 2 days. 21 days post-transfection, cells were fixed and stained with Giemsa. Unfixed foci of morphologically transformed cells were subcloned using microcylinders, expanded, and tested for anchorage-independent growth in 0.3% Noble agar ($2>10^4$ cells per dish) in Iscove's medium supplemented with 15% FBS, and colonies were scored 2–3 weeks later.

Vector Virus Production and Infection: Human kidney 293T cells were transfected with 15 μg of ecotropic helper virus DNA plasmid plus 15 μg of SRβ vector DNA encoding $p19^{ARF}$ [Quelle et al., Cell, 83:9931000 (1995b)]. Cell supernatants containing infectious retroviral pseudotypes were harvested 24–60 hr post-transfection, pooled on ice, and filtered (0.45 μm membrane). Infections of exponentially growing mouse fibroblasts were performed in a 8% $CO_2$ atmosphere with 2 ml of virus-containing culture supernatant containing 10 μg/ml polybrene (Sigma, St. Louis Mo.) for each 100 mm diameter plate culture. After 3 hr, 10 ml fresh medium was added. Cells were harvested 48 hours after infection and the percentage in S phase was determined by flow cytometric analysis of DNA content or by incorporation of [3H]-thymidine into replicating cell DNA.

[$^3$H]-thymidine incorporation into DNA: Cells infected with viral vector plasmids encoding $p19^{ARF}$ or lacking cDNA inserts were distributed at $5 \times 10^3$ cells per well into 96 well microtiter plates. Following attachment, the cells were starved in complete medium containing 0.1% FBS and then restimulated with complete serum-containing medium to re-enter the cell division cycle. [$^3$H]-thymidine (5 Ci/mmol, 0.1 μCi/well; Amersham) was added with the medium, and 24 hours later, incorporation of radioactivity into DNA was measured in disrupted cells trapped on ethanol washed filters using a Wallac Betaplate scintillation counter (Gaithersburg MD).

RNA expression and nucleotide sequencing: Total RNA extracted from mouse tissues and pellets of cultured cells was used as template for cDNA synthesis using a StrataScript RT-PCR kit (Stratagene, La Jolla Calif.) per manufacturer's instructions. PCR amplification of transcripts encoding either $p16^{INK4a}$ or $p19^{ARF}$ was performed [Quelle et al., Cell, 83:993–1000 (1995b)] using 5' sense primers based on unique exon 1α or exon 1β sequences and a 3' antisense primer based on a common exon-2 sequence. RT-PCR products ~0.5 kb in length were detected by direct ethidium bromide staining after electrophoretic separation on agarose gels. DNA sequencing of both strands was performed with the same primers using dideoxynucleotide chain termination and automated fluorescent-based analysis.

Protein analysis: For analysis of $p16^{INK4a}$ and $p14^{ARF}$ expression, frozen mammalian cell pellets ($1 \times 10^7$ cells per ml) or tissue samples were disrupted in ice-cold EBC buffer (120 mM NaCl, 50 mM Tris HCl, pH 0.8, 0.5% NP-40, 1 mM EDTA) and left for 1 hour on ice. Nuclei and debris were removed by centrifugation in a microfuge at 12,000 RPM for 10 min at 4° C. Proteins (1 mg/ml) were immunoprecipitated, electrophoretically separated on denaturing polyacrylamide gels containing sodium dodecyl sulfate (SDS), transferred to nitrocellulose, and detected using affinity-purified rabbit antibodies raised to the C-terminal peptides of either $p16^{INK4a}$ or $p19^{ARF}$ [Quelle et al., Oncogene, 11:635–645 (1995a); Quelle et al., Cell, 83:993–1000 (1995b)]. Sites of antibody binding were visualized by enhanced chemiluminescence (ECL, Amersham). Where indicated, $p16^{INK4a}$ immunoprecipitates were separated on gels and blotted with rabbit antiserum to CDK4. $p21^{Cip1}$ and p53 were visualized by direct immunoblotting with commercial antibodies [monoclonal F-5 (Santa Cruz Biochemicals) and Ab-7 (Calbiochem, La Jolla Calif.), respectively].

MEF cells metabolically labeled for 2 hours with 200 (Ci/ml [$^{35}$S]-methionine (1369 Ci/mmol, ICN Pharmaceuticals, Costa Mesa Calif.) were lysed in 50 mM Tris HCl, pH 8.0, containing 150 mM NaCl, 5 mM EDTA, and 0.5% Nonidet P-40. Centrifuged cell lysates were precipitated using PAb246, a mouse-specific and conformation-dependent antibody that recognizes wild-type, but generally not mutant p53 [Yewdell et al., J. Virol., 59:444–452 (1986)], and PAb240, a pan-specific antibody that recognizes many mutant p53s but not the wild-type protein in its native conformation [Gannon et al., EMBO J., 9:1595–1602 (1990)]. Precipitates were solubilized in gel sample buffer, electrophoretically separated on denaturing polyacrylamide gels, and visualized by autoradiography of the dried slab gels.

Radiation Response: Replicative DNA synthesis was quantitated by bivariate flow cytometry following procedures for irradiation described by others [Deng et al., Cell, 82:675–684 (1995)]. In brief, cells made quiescent by serum starvation for 96 hrs were irradiated with 5 or 20 Gy and then released into complete medium containing 10% FBS and 65 μM BrdU. Cells were fixed 24 hrs later in 70% ethanol and kept at 20° C. until analysis. We compared two independently derived ARF(+/+) strains (2 cultures of each) with two ARF(−/−) strains (2 cultures) in two separate experiments. Data for (+/+) and (−/−) strains in each experiment were separately pooled. Fixed cells were incubated in 4N HCl for 30 minutes at room temperature, washed with PBS, and resuspended in 0.1M Borax containing 0.1% Tween-30 and 0.1% BSA. Cells were exposed for 30 minutes at room temperature to monoclonal anti-BrdU (Becton Dickinson, San Jose Calif.) or to isotype-matched control mouse immunoglobulin G (IgG), washed with PBS, and counterstained for 30 minutes with fluorescein-conjugated goat antibodies to mouse IgG (Coulter, Hialeah, FL). Washed cells were resuspended in PBS containing 0.5% BSA, 20 μg/ml propidinm iodide, and 50 μg/ml DNAse-free RNAse (Calbiochem), incubated at room temperature for 30 minutes, and analyzed by flow cytometry. Fluorescence from FITC-labeled incorporated BrdU and propidium iodide-DNA complexes was measured on a FACSCalibur flow cytometer (Becton Dickinson) using 488 nm laser excitation. Cell debris and background artifacts were electronically gated out, and the percentages of cells in different cell cycle phases were computed using CellQuest software (Becton Dickinson). Similar numbers of cells were analyzed for each sample with all standard deviations less than ±4% of the mean.

TABLE 1

| Mouse | Sex | Age (weeks) | Treatment | Histology | p16 PCR | p16 Blot |
|---|---|---|---|---|---|---|
| K5 | M | 18 | None | Fibrosarcoma | +* | + |
| K11 | M | 8 | None | Metastic salivary gland carcinoma | +* | + |
| K17 | F | 21 | None | Thymoma | ND | ND |
| K75 | F | 11 | None | Malignant fibrous histiocytoma | ND | ND |
| K116 | M | 18 | None | Lymphoma (brain) | ND | ND |
| K199 | M | 16 | None | Fibrosarcoma | ND | ND |
| K86 | F | 12 | DMBA | Epdiermal papilloma (4 sites) | ND | + |
| K88 | F | 20 | DMBA | Epidermal papilloma | ND | ND |
| K90 | F | 14 | DMBA | Lymphoma and epidermal papilloma | + | + |
| K98 | F | 13 | DMBA | Mestastic epidermoid carcinoma | ND | + |
| K106 | M | 9 | DMBA | Invasive epidermoid carcinoma | +* | + |
| K149 | M | 12 | DMBA | Fibrosarcoma, malignant adenexal tumor | ND | ND |
| K150 | M | 14 | DMBA | Epidermal papilloma (2 sites) | ND | ND |
| K151 | F | 13 | DMBA | Fibrosarcoma and epidermal papilloma | ND | ND |
| K163 | M | 13 | DMBA | Epidermal papilloma (4 sites) | ND | ND |
| K173 | M | 12 | Irradiation | Fibrosarcoma | ND | ND |
| K175 | M | 12 | Irradiation | Lymphoma | ND | ND |
| K178 | F | 13 | Irradiation | Fibrosarcoma | ND | ND |
| K185 | M | 19 | Irradiation | Lymphoma | ND | ND |

Age refers to date of tumor detection or death of the animal. Where indicated, mice received ionizing radiation (4 Gy) [Kemp et al., Nat. Genetics, 8:66–69 (1994)] or were treated with DMBA 5–7 days after birth [Serrano et al., Cell, 85:27–37 (1996)]. Nine of 11 DMBA-treated animals, 4 of 6 animals that received sublethal γ irradiation, and 6 of 18 untreated mice developed tumors by 5 months of age. Fibrosarcomas arose subcutaneously and were all highly invasive to skeletal muscle and bone. Skin tumors in DMBA-treated animals exibited variable degrees of anaplasia, with lower grade papillomatous growths sometimes arising at multiple independent sites, and with higher grade carcinomas presenting as either locally invasive or frankly metastatic varants. Lymphomas were anaplastic large-cell type with T cell markers. Detection of p16$^{INK4a}$ transcripts (PCR) or protein (immunoblotting) in primary tumor tissues is noted by "+"; N.D. = not done; (*) RT-PCR products taken for nucleotide sequencing.

Results

Mice lacking p19$^{ARF}$ express wild-type p16$^{INK4a}$. A conventional targeting vector was used to ablate ARF exon-1β ini mouse embryonic stem cells, replacing it with a neomycin resistance (neo) gene (FIG. 8A). Exon-1β is included within a 7.8 kb AflII fragment that was detected with a unique sequence genomic probe, but an AflII site inserted into the neo cassette reduced the size of the hybridizing fragment to 6 kb. Germline transmission of the mutant allele from a chimeric founder male and subsequent interbreeding of hemizygous offspring gave rise to normally developing animals lacking exon-1β at the expected Mendelian frequency (22% ARF-null, 52% heterozygous, 26% wild-type; total animals: 200) (FIG. 8B). INK4a exon-1α and the tandemly linked INK4b locus remained intact (see below).

Animals lacking exon 1β [designated ARF (−/−)] expressed transcripts encoding p16$^{INK4a}$ but not p19$^{ARF}$, RT-PCR analysis showed that ARF β transcripts amplified from primers based on 5' exon 1β and 3' exon-2 sequences were expressed in testes and livers of ARF(+/+) animals (FIG. 8C, lanes 2 and 3), but were absent from their ARF(−/−) counterparts (lanes 4 and 5). Control murine erythroleukemia (MEL) cells expressed much higher levels of ARF RNA (lane 6). The levels of ARF mRNA in adult tissues are low, and the protein is not visualized with antiserum that detects the polypeptide in MEL cell lysates [Quelle et al., Cell, 83:993–1000 (1995b); Zindy et al. Oncogene, 15:203–211 (1997)]. Authentic INK4a α transcripts containing 5' exon 1α and 3' exon-2 sequences were detected in both ARF(+/+) and ARF(−/−) animals (FIG. 8C). Nucleotide sequencing of α transcripts amplified from testes of ARF(−/−) mice confirmed that they lacked mutations.

Neither p16$^{INK4a}$ nor p19$^{ARF}$ are expressed during mouse embryonic development, but when embryo cells are explanted into culture, p16$^{INK4a}$ is induced and accumulates as MEFs are passaged [Zindy et al., Oncogene, 15:203–211 (1997)]. MEF cultures initiated from genotyped embryos were passaged in vitro on a defined "3T9" schedule and tested for p16$^{INK4a}$ expression. p16$^{INK4a}$ was induced as six independent MEF cultures were passaged (FIG. 9A). well before they underwent senescence and regardless of their ARF genotype. Even higher levels of p16$^{INK4a}$ were detected in ARF(−/−) MEFs, as compared to those in cells retaining one or two wild-type ARF alleles. All inactivating p16$^{INK4a}$ mutants described to date, including those that are temperature-sensitive, block the protein's ability to bind to CDK4 [Koh et al., Nature, 375:506–510 (1995); Lukas et al., Nature, 375:503–506 (1995); Ranade et al., Nature Genetics, 10:114–116 (1995); Raymond and Brent, Oncogene, 11:1173–1178 (1995); Wick et al. Oncogene, 11:2003–2019 (1995); Yang et al., Cancer Res., 55:2503–2506 (1995); Parry and Peters, Mol. Cell. Biol., 16:3844–3852 (1996); Quelle et al., Proc. Natl. Acad. Sci. USA, 94:3436–3440 (1997)]. Hence, the fact that P16$^{INK4a}$ immunoprecipitates from ARF (−/−) MEFs contained CDK4 (FIG. 9B) argues that the CDK inhibitor is functional. In proliferating MEFs, CDK4 levels exceed those of the INK4 inhibitors, and as expected, assays for cyclin D- and CDK4-associated Rb kinase activity confirmed the presence of catalytically active, cyclin D-bound pools of CDK4 in these cells.

Early passage MEFs derived from ARF(−/−) animals are impaired in growth control: Passaged ARF(+/+) cells initially underwent ~2 population doublings in the 3 days prior to dilution and replating, but their virtuality ceased by passages 17–20 (FIG. 10A). In contrast, cultures from ARF(−/−) embryos accumulated many more cells. At passage 5, they proliferated at significantly faster rates than their ARF(+/+) counterparts and grew to 3-fold higher densities at confluence (FIG. 10B; note log scale on ordinate). ARF(+/−) cells showed an intermediate phenotype. By passage 10, the growth rates of ARF(+/+) and ARF(+/−) cells had further slowed, but the division rate of ARF(−/−) cells was maintained (FIG. 10B) and they proliferated continuously thereafter never undergoing a detectable senescence crisis (FIG. 10A). Therefore, ARF(−/−) cells have an increased proliferative capacity grow faster, and are somewhat less responsive to inhibition by cell-cell contact than their wild-type counterparts.

Another property of INK4a nullizygous MEFs is their capacity to be directly transformed by oncogenic ras alleles without a further requirement for collaborating "immortalizing genes", such as E1a or myc [Serrano et al., Cell, 85:37–37 (1996); Weinberg, Cell, 88:573–575 (1997)]. When early passage MEFs were transfected with an expression vector encoding oncogenic Ha-ras (Val-12), foci of transformed cells were detected in ARF(−/−) but not ARF (+/+) MEFs. 16 (12 foci per 60 mm diameter plate in 3 separate experiments with two different ARF(−/−) clones were obtained. These frequencies were similar to those obtained with ARF(+/+) MEFs transfected with vectors encoding both Ha-ras and myc. Morphologically transformed cells were highly refractile and no longer contact-inhibited (FIG. 10C, a and b). Individually expanded transformed foci expressed $p16^{INK4a}$ which coprecipitated with CDK4 (FIG. 10C, c). Early passage ARF(−/−) cultures yielded no cells that were capable of anchorage-independent growth in semisolid medium, but ras-transformed subclones formed colonies in agar and tumors in SCID mice. When individual agar colonies picked at random were expanded, 12 of 12 continued to express $p16^{INK4a}$. Thus, Ha-ras alone can oncogenically transform $p19^{ARF}$-negative, $p16^{INK4a}$-positive MEFs.

ARF or p53 loss-of-function in MEF cell lines: Rare MEF variants that weather the senescence crisis can become established as permanent cell lines [Todaro and Green, J. Cell Biol., 17:299–313 (1963)], and these frequently contain mutant p53 alleles [Harvey and Levine, Genes Dev., 5:2357–2385 (1991); Rittling and Denhardt, Oncogene, 7:935–942 (1992)] or sustain INK4a deletions [Kamb et al., Science 264:436–440 (1994); Nobori et al., Nature, 368:753–756 (1994); Zindy et al., Oncogene, 15:203–211 (1997)]. In an experiment performed with four wild-type ARF(+/+) MEF strains, pre-crisis cells at passage 6 expressed $p16^{INK4a}$ but no detectable $p19^{ARF}$ (FIG. 11A, lanes 1–4). Lysates from early passage strains contained wild-type p53 precipitated with an antibody (PAb246) that does not react with mutant forms [Yewdell et al., J. Virol., 59:444–452 (1986)]. After emergence from crisis, however, MEFs from three strains had sustained p53 mutations, as determined by selective precipitation of p53 by an antibody (PAb240) that recognizes mutant p53s but not the native p53 conformation [Gannon et al., EMBO J., 9:1595–1602 (1990)] (lanes 5–7). Like MEL cells which contain a disrupted p53 gene and others lacking functional p53 [Quelle et al., Cell, 83:993–1000 (1995b)], these three MEF lines synthesized abundant $p19^{ARF}$ and even higher levels of $p16^{INK4a}$ than those seen in early passage strains (lanes 5–7). In contrast an established line that underwent deletion of both INK4a alleles expressed neither $p16^{INK4a}$ nor $p19^{ARF}$ and retained wild-type p53 (lane 8).

ARF(+/−) MEF strains generated established lines 4–6 passages earlier than ARF(+/+) cells (passages 18–20 in FIG. 10A), preferentially yielding ARF(−/−) variants. Wild-type and mutant ARF alleles were detected with an exon 1β probe in MEFs from three such clones at passage 1, but only mutant ARF was detected at passage 20 when proliferating variants had emerged (FIG. 11B). ARF(−/−) variants arising from ARF(+/−) MEF strains (lanes 2, 4, and 6), MEF lines from ARF-null mice (e.g. lanes 9, 10), or cell lines arising from wild-type MEFs that sustained hi-allelic ARF deletions (lanes 8, 11) synthesized only wild-type p53 (FIG. 11A and FIG. 12 below), Conversely, cell lines that retained wild-type ARF alleles synthesized mutant p53 (e.g. FIG. 11A, lanes 5–7 and FIG. 11B, lanes 7 and 12). Cell lines containing mutant p53 and retaining ARF rapidly became polyploid [c.f. Harvey et al., Onconogene, 8:2457–2467 (1993); Fukusawa et al., Science, 271:1744–1747 (1996)], but all ARF(−/−)/p53 lines remained pseudodiploid through additional passages [c.f. Zindy et al., Oncogene, 15:203–211 (1997); also clones 3–2 and 3–3 through passage 27]. In short, functional loss of p53 or $p19^{ARF}$ appeared to be mutually exclusive events as cells overcame a senescence block, with p53 predisposing to more rapid ploidy changes.

Although wild-type MEFs that sustained bi-allelic deletions of ARF lacked flanking INK4a and INK4b genes (FIG. 11B, lanes 8 and 11), those containing a single neo-disrupted ARF allele gave rise to ARF(−/−) variants that retained INK4a (FIG. 4B, lanes 1–6, exon 1α probe) and expressed both $p16^{ARF4a}$ and $p15^{INK4b}$ (FIG. 11C). These results strongly suggest that selection for ARF loss results in co-deletion of INK4a and INK4b, and not vice versa.

ARF-induced arrest depends on p53: Levels of $p19^{ARF}$ are elevated in cells lacking wild-type p53 function (FIG. 8C, lane 6; FIG. 11A, lanes 5–7) [Quelle et al., Cell, 83:993–1000 (1995b)], compatible with the possibility that p53 may normally suppress ARF. However, no change in $p19^{ARF}$ levels were observed when fibroblasts bearing a temperature-sensitive p53 allele were shifted between permissive and nonpermissive temperatures, implying that p53 does not directly regulate ARF expression [Quelle et al., Proc. Natl. Acad. Sci. USA, 94:3436–3440 (1997)].

Early passage MEFs, regardless of their ARF status, expressed equivalent levels of wild-type p53 (FIG. 12A), which was rapidly and transiently induced in ARF-null cells in response to γ irradiation (FIG. 12B). Levels of the p53-responsive CDK inhibitor, $p21^{Cip1}$ also rose within 2–4 hours of exposure to 5 Gy ionizing radiation (FIG. 5B). To see whether ARF-null cells underwent G1 phase arrest in response to DNA damage, arrested serum-starved cultures from two different sets of ARF(−/−) and ARF(+/+) MEF strains were irradiated with 5 or 20 Gy and transferred into medium containing serum and BrdU. Cells were stained for DNA content (propidium, iodide) and replicative DNA synthesis (BrdU) 24 hours after release from the $G_0$ block, and the S phase fractions were determined by flow cytometry. Although p53-negative MEFs are not inhibited from entering S phase after irradiation [Kastan et al., Cancer Res., 51:6304–6311 (1991); Kuerbitz et al., Proc. Natl. Acad. Sci. USA, 89:7491–7495 (1992); Deng et al., Cell, 82:675–684 (1995)], both ARF(+/+) and ARF(−/−) MEFs underwent G1 arrest at the same efficiency. The percentages of cells entering S phase after irradiation relative to unirradiated cells were 26% for ARF(+/+) and 30.9% for ARF(−/−) MEFs, versus >90% for p53-negative MEFs. Loss of growth control in ARF(−/−) cells is therefore not due to p53 mutation or deletion, or to apparent perturbation of its G1 checkpoint function.

Both ARF(−/−) and ARF(+/+) MEFs at passage 9 were completely inhibited from entering S phase when tested 24 hours after infection with an ARF-coding retrovirus (FIG. 12C). NIH-3T3 cells and clone 6–18 cells lacking the entire INK4a locus were also sensitive, underscoring the fact that arrest by $p19^{ARF}$ does not depend upon $p16^{INK4a}$. On the other hand, established (10)1 and (10)3 Balb-3T3 cell lines lacking p53 and cell lines established from ARF(+/+) MEFs that had sustained p53 mutations were resistant to growth arrest by vectors encoding p19$^{ARF}$ (FIG. 12C). The latter cells expressed elevated levels of endogenous p19$^{ARF}$ (e.g. FIG. 11A, lanes 5–7) that closely approximated those achieved in vector-infected p53+/ARF-null clones [Quelle et al., Cell, 83:993–1000 (1995b)]. In summary, 7 of 7 tested cell lines lacking p53 function lost responsiveness to p19$^{ARF}$, while 4 of 4 p53+/ARF-null lines were sensitive.

Although basal p53 levels were similar in ARF(-/-) and ARF(+/+) cells (FIG. 12A), ARF-null MEFs reproducibly expressed lower levels of p21$^{Cip1}$ (e.g. FIG. 12B, 0 hr). In cells infected with retroviral vectors encoding p19$^{ARF}$, p53 and p21$^{Cip1}$ were induced in clones expressing wild-type p53, regardless of their ARF genotype (FIG. 12D). In contrast, cells lacking p53 (clone 10(1)) or containing mutant p53 (5–9) exhibited no p19$^{ARF}$-dependent induction of p21$^{Cip1}$, observations that were reproduced in lines 10(3), 5–10, and 6–14. Therefore ectopic expression of p19$^{ARF}$ increases p21$^{Cip1}$ expression in a p53-dependent manner.

p19$^{ARF}$-deficient mice develop cancer: By 2 months of age, ARF(-/-) mice began to spontaneously develop tumors (Table 1). Six of 18 ARF-null animals exhibited malignant tumors by six months of age, but none were observed in 23 ARF(+/+) or 66 ARF(+/-) mice during the same period. Nine of 11 ARF(-/-) mice treated one week after birth with DMBA developed tumors by 9–20 weeks of age (Table I). Skin tumors occurred at multiple sites and exhibited varying degrees of anaplasia with two mice manifesting invasive, poorly differentiated epidermoid carcinomas. Three animals within this group developed two tumors of completely different histologic types. Identically treated control animals [12 ARF(+/+) and 13 ARF(+/-)] did not develop tumors during the six month observation period. DMBA treatment predisposes to development of skin tumors under the conditions used, but other control animals derived from the same mouse strains did not develop skin tumors after DMBA treatment until they were over 10 months old, consistent with historical data [Reiners et al., Carcinogenesis 5:301–307 (1984); Naito and DiGiovanni, In Carcinogenesis, vol. III Skin Tumors, C.J. Conti, T.J. Slaga, and A.J.P. Klein-Szanto, eds., New York: Raven Press, pp. 187–212 (1989)]. Four of six mice that were γ irradiated as newborns developed fibrosareomas or anaplastic T cell lymphomas.

Enough tumor tissue was obtained from six mice (Table 1) to demonstrate p16$^{INK4a}$-coding transcripts (FIG. 13A) and protein (FIG. 13B) in uncultured cells. Fibrosarcoma cells explanted into culture from animal K5 grew rapidly and were maintained as a continously proliferating cell line. Like the primary tumor these synthesized p16$^{INK4a}$ mRNA and protein. The lymphoma from mouse K90 also synthesized p16$^{INK4a}$. Both the K5 and K90 tumor cells expressed p16$^{INK4a}$-associated CDK4, again implying that the CDK inhibitor was functionally wild-type (FIG. 13B). Similar protein data were obtained with four other primary tumors (animals K11, K86, K98, K106). Nucleotide sequence analysis of PCR products confirmed that p16$^{INK4a}$ transcripts amplified from tumors taken from animals K5, K11, and K106 had not sustained mutations. Therefore p19$^{ARF}$ functions as a bona fide tumor suppressor.

Discussion p16$^{ARF4a}$ is expressed appropriately in cells lacking ARF: Mice lacking exon-2 of the INK4a gene were previously found to develop tumors of many histologic types [Serrano et al., Cell 85:27–37 (1996)]. MEFs derived from these animals became established in culture without undergoing a senescence crisis, and even cells in early passage could be transformed by oncogenic Ha-ras alone. Given that these previously reported features of INK4a-null animals have now been recapitulated in animals lacking only p19$^{ARF}$, the relative contributions of p19$^{ARF}$ and p16$^{INK4a}$ to tumor suppression need to be reevaluated.

One possible interpretation of the results might have been that disruption of ARF exon 1β perturbed p16$^{INK4a}$ expression. However, normal tissues from ARF(-/-) mice, cultured MEFs, ras-transformed fibroblasts, mouse tumors, and cell lines derived from them all expressed p16$^{INK4a}$. The hallmark of nonfunctional p16$^{INK4a}$ point mutants so far tested, including several temperature-sensitive alleles, is their inability to bind to CDK4 or CDK6, and so, the simplest and most reliable assay for p16$^{INK4a}$ function is its physical interaction with these catalytic subunits [Parry and Peters, Mol. Cell. Biol., 16:3844–3852 (1996)]. By this criterion, p16$^{INK4a}$ in tissues of ARF-nullizygous mice and in cultured cells and tumors derived from them, was functionally wild-type. Nucleotide sequencing of RT-PCR products from testes and from several primary tumors confirmed this prediction.

Typical patterns of p16$^{INK4a}$ and p15$^{INK4b}$ expression were maintained in MEFs, irrespective of whether or not they retained ARF. In fact, p16$^{INK4a}$ protein levels were higher in ARF(-/-) MEFs than in their matched ARF(+/-) and ARF(+/+) counterparts, possibly because, without competition from the upstream ARF β promoter, a transcripts encoding p16$^{INK4a}$ may be more efficiently spliced. Thus, insertion of neo into exon 1β did not dampen expression from the two flanking INK4 genes. The fact that ARF-null MEFs did not exhibit a detectable senescence crisis fingers p19$^{ARF}$ rather than p16$^{INK4a}$ as the mediator of these events. When wild-type MEFs underwent bi-allelic deletion of ARF during establishment, the INK4a and INK4b, genes were concomitantly lost. However, ARF-null cell lines arising from ARF(+/-) MEF stains retained hemizygous INK4 coding sequences and continued to express p16$^{INK4a}$ and p15$^{INK4b}$, implying that INK4a and INK4b deletions occur as a consequence of selection for cells that bypass the senescence block. ARF(-/-) cells transformed by Ha-ras (Val-12) alone continued to express functional p16$^{INK4a}$, so the loss of p19$^{ARF}$ mimics effects of "immortalizing genes", such as E1a and myc, that can similarly collaborate with ras [Weinberg, Cell, 88:573–575 (1997)].

ARF functionally interacts with p53: Expression of p19$^{ARF}$ was not detected in early passage wild-type MEF strains, but it was readily observed in derived cell lines containing mutant p53. Only negative evidence was obtained for p53 directly regulating p19$^{ARF}$ expression in fibroblasts [Quelle et al., Proc. Natl. Acad. Sci. USA, 94:3436–3440 (1997)], so significantly higher levels of endogenous p19$^{ARF}$ observed in cells lacking p53 function might instead reflect selection for p53 loss in cells in which p$^{19ARF}$ had already been induced. ARF-positive MEFs that weather a senescence crisis and retain the gene likely become established as a result of independent mechanisms that override p19$^{ARF}$-mediated growth suppression, and two lines of evidence suggest that loss of p53 function is the key event. First, cells lacking a functional p53 gene are resistant to p19$^{ARF}$-induced cell cycle arrest. Second, established MEF lines that retained ARF sustained p53 mutations, whereas those that deleted ARF preserved p53 function. Interestingly, lines with mutant p53 rapidly become polyploid [reviewed in Levine, Cell, 88:323–331 (1997)], whereas ARF-null lines that retain p53 function seem to remain pseudodiploid through more passages. In mice then, p53 and ARF inactivation appear to represent alternative mechanisms for bypassing the senescence block, and p53 loss predisposes more strongly to changes in ploidy [Fukusawa et al., *Science*, 271:1744–1747 (1996)]. Species with longer life spans likely manifest more stringent controls over cell senescence, and in cultures of human cells, loss of both p53 and ARF, or other collaborating events, may well be required to endow them with an extended proliferative capacity [Rogan et al., *Mol. Cell. Biol.*, 15:4745–4753 (1995); Alcorta et al., *Proc. Natl. Acad. Sci. USA*, 93:13742–13747 (1996); Hara et al., *Mol. Cell. Biol.*, 16:859–867 (1996); Noble et al., *Oncogene* 13:1259–1268 (1996); Reznikoff et al., *Cancer Res.*, 56:2886–2890 (1996); Serrano et al., *Cell*, 88:593–602 (1997)].

Neither point mutations within ARF exon 1β nor promoter hypermethylation have so far been detected in tumors or in tumor-derived cell lines [Mao et al., *Cancer Res.*, 55:2995–2997 (1995); Merlo et al., *Nature Med.* 1:686–692 (1995); Shapiro et al., *Cancer Res.*, 55:6200–6209 (1995); Stone et al., *Cancer Res.*, 55:2988–2994 (1995); Fitzgerald et al., *Proc. Natl. Acad. Sci. USA*, 93:8541–8545 (1996); Herzog et al., *Oncogene*, 13:1885–1891 (1996); Kubo et al., *Biochem. Biophys. Res. Commun.*, 232:38–41 (1997); Swafford et al., *Mol. Cell. Biol.*, 17:1366–2374 (1997); Tanaka et al., *Ing. J. Cancer*, 70:473–442 (1997)]. Consequently, ARF inactivation may require bi-allelic deletions, as opposed to p53, whose dominant-negative mutants subvert the function of the wild-type tetrameric product. During passage in culture, ARF(+/−) MEFs sustained deletions of their remaining ARF allele while retaining wild-type p53, and such strains became established as cell lines 4–6 passages earlier than ARF(+/+) cells. In normal MEFs containing two wild-type ARF alleles, p53 mutation is readily detected [Harvey and Levine, *Genes Dev.*, 5:2375–2385 (1991)], but in cells hemizygous for ARF, loss of the remaining wild-type ARF allele is at least as frequent an occurrence.

MEF cell lines lacking ARF, whether directly derived from nullizygous animals or from wild-type cells that had deleted both copies of the gene during the process of establishment, promptly stopped proliferating when infected with a retrovirus encoding $p19^{ARF}$. Both early and late passage ARF(−/−) MEFs expressed low levels of p53, which was induced by γ irradiation and, in turn, was able to induce $p21^{Cip1}$ and to block cell proliferation. Thus, such cells were not defective in p53-mediated checkpoint control. In contrast, ARF-positive cell lines that acquired p53 mutations or deletions were refractory to $p19^{ARF}$-induced growth arrest. MEFs from p53-null mice are genetically unstable and do not senesce either [Harvey et al., *Oncogene*, 8:2457–2467 (1993)]. In principle, $p19^{ARF}$ might exert its effects though a p53-regulated gene such as $p21^{Cip1}$ [El-Deiry et al., *Cell*, 75:817–825 (1993)], which was cloned as a senescent cell-derived growth inhibitor [Noda et al., *Exp. Cell Res.*, 211:90–98 (1994)]. In agreement with this hypothesis basal $p21^{Cip1}$ levels were reduced in ARF(−/−) versus ARF(+/+) MEFs, and enforced expression of $p19^{ARF}$ induced $p21^{Cip1}$ in a p53-dependent manner. Although induction of p53 and $p21^{Cip1}$ by (-irradiation does not depend on ARF, enforced p19 expression could conceivably trigger a stress response that mimics effects of DNA damage. Whatever the exact mechanisms, observations that $p19^{ARF}$ can function "upstream" of p53 raise the possibility that the INK4a/ARF locus is a master growth regulator whose encoded proteins interface with both the Rb ($p16^{INK4a}$) and p53 ($p19^{ARF}$) pathways.

Despite the fact that $p19^{ARF}$ depends on p53 for inducing growth arrest, loss of both proteins can occur in tumor cells. A fibrosarcoma was identified that arose spontaneously in an ARF(−/−) mouse that had lost p53 bin retained wild-type $p16^{INK4a}$, indicating that p19 and p53 can likely collaborate in tumor progression. One obvious possibility is that p53 can regulate apoptotic functions in ARF(−/−) cells unrelated to cell cycle progression per se.

$p16^{ARF4a}$ and tumorigensis: Although it is evident that $p19^{ARF}$ functions as a tumor suppressor in mice, contributions of $p16^{INK4a}$ to the phenotype of INK4a-null animals are not excluded by the present studies. Lymphomas and Fibrosarcomas were observed which predominated in their studies (as in p53-null mice) [Donehower et al., *Nature*, 356:215–221 (1992); Jacks et al., *Curr. Biol.*, 4:1–7 (1994); Kemp et al., *Nat. Genetics*, 8:66–69 (1994)], as well as tumors which are otherwise very rare. The timing of tumor appearance was also similar. The status of ARF mRNA expression in nice disrupted in INK4a exon 2 versus 1α is also interesting. The aminoterminal domain of $p19^{ARF}$ is necessary and sufficient to induce cell cycle arrest [Quelle et al., *Proc Natl. Acad. Sci. USA*, 94:3436–3440 (1997)], so animals disrupted in exon-2 may not be completely devoid of ARF function if stable mRNAs encoding exon 1β are translated.

Data implicating $p16^{INK4a}$ as a tumor suppressor in humans remains compelling. In certain tumor types, inactivating point mutations of $p16^{INK4a}$ are common while deletions are rare [Hirama and Koeffler, *Blood*, 86:841–854 (1995); Hall and Peters, *Adv. Cancer Res.*, 68:67–108 (1996); Pollock et al., *Genes Chrom. Cancer;* 15:77–88 (1996)]. Some mutations fall into exon 1α, which does not encode $p19^{ARF}$ [Gruis et al., *Nature Genet.*, 10:351–353 (1995); Holland et al., *Oncogene*, 11:2289–2294 (1995); Walker et al., *Hum. Mol. Genet.*, 4:1845–1852 (1995)], and missense mutations within exon-2 that affect both reading frames can selectively target $p16^{INK4a}$ [Quelle et al., *Proc. Natl. Acid. Sci. USA*, 94:3436–3440 (1997)]. Therefore, cancer-specific point mutations preferentially, and perhaps exclusively, impinge on $p16^{INK4a}$. INK4a deletions and mutations appear to be functionally distinct.

Example 9

Functional and Physical Interactions of the ARF Tumor Suppressor with p53 and Mdm2

Introduction

The INK4a-ARF locus encodes two unrelated tumor suppressor proteins, $p16^{INK4a}$ [Serrano et al., *Nature*, 366:704–707 (1993)] and $p19^{ARF}$ [Quelle et al., *Cell*, 83:993–1000 (1995)] to act to modify the activities of the retinoblastoma protein (Rb) and p53, respectively. Whereas the p53 gene is mutated in about half of human cancers [Hollstein et al., *Nucleic Acids Res.*, 22:3551–3555 (1994)], disruption of one or more elements within the INK4a-ARF locus occurs almost as frequently in an equally broad range of tumor types [Hall and Peters, *Adv. Cancer Res.*, 68:67–108 (1996)]. INK4a-ARF contains two promoters and alternative first exons, designated 1α and 1β, whose RNA products are each spliced to two common exons [Quelle et al., *Cell*, 83:993–1000 (1995); Duro et al., *Oncogene*, 11:21–29 (1995); Mao et al., *Cancer Res.*, 55:2995–2997 (1995); Stone et al., *Cancer Res.*, 55:2988–2994(1995)]. Exon 1α, 2 and 3 encode $p16^{INK4a}$, a protein that specifically inhibits the ability of cyclin D-dependent kinases [Serrano et al., *Nature*, 366:704–707

(1993)] to phosphorylate Rb [Kato et al., *Genes Dev.*, 7:331–342 (1993); Ewen et al., *Cell*, 73:487–497 (1993); Lukas et al., *J. Cell Biol.*, 125:625–638 (1994)]. Increased expression of p16$^{INK4a}$ can attest cells in the G1 phase of the cell cycle, but cells that lack functional Rb are resistant to p16's effects [Lukas et al., *Nature*, 375:503–506 (1995); Koh et al., *Nature*, 375:506–50 (1995); Mederma et al., *Proc. Natl. Acad. Sci. USA*, 92:6289–6293 (1995)]. In contrast, the exon 1β–2–3 transcript encodes p19$^{ARF}$, which bears no homology to p16$^{INK4a}$ and is composed of a 64 amino acid N-terminal domain derived from exon-1β and 105 C-terminal amino acids encoded by the alternative reading frame of exon 2. The p19$^{ARF}$ protein can induce both G1 and G2 phase arrest [Quelle et al., *Cell*, 83:993–1000 (1995)] in a manner that depends upon functional p53 [Kamijo et al., *Cell*, 91:641–659 (1997)]. However, ARF-null cells exhibit an intact p53-dependent G1 checkpoint in response to DNA damage by ionizing radiation [Kamijo et al., *Cell*, 91:641–659 (1997)], so ARF must lie on a different signaling pathway.

While neither p16$^{INK4a}$ nor p19$^{ARF}$ are detectably expressed during mouse embryogenesis, explantation of mouse embryo fibroblasts (MEFs) into culture induces the synthesis of both proteins [Kamijo et al., *Cell*, 91:641–659 (1997); Zindy et al., *Oncogene*, 15:203–211 (1997)]. They accumulate progressively as MEFs are passaged, during which time cell proliferation slows and eventually stops. Rare cells that spontaneously bypass this block give rise to established cell lines [Todaro and Green, *J. Cell. Biol.*, 17:299–313 (1963)]. In about 75% of cases, establishment of cell lines is associated with loss of p53 function [Harvey and Levine, *Genes Dev.*, 5:2375–2385 (1991)], while many of the remaining fraction sustain bi-allelic loss of the INK4a-ARF locus [Kamijo et al., *Cell*, 91:641–659 (1997); Zindy et al., *Oncogene*, 15:203–211 (1997)]. Although there was reason to infer that establishment of MEF-derived cell lines resulted from p16$^{INK4a}$ loss [Serrano et al., *Cell*, 85:27–37 (1996)], deletion of ARF alone is sufficient to enable MEFs to grow, despite continued p16$^{INK4a}$ expression, [Kamijo et al., *Cell*, 91:641–659 (1997)]. In MEF strains, then, ARF and p53 can act epistatically to govern the number of allotted population doublings, with loss of either facilitating establishment. Interestingly, MEFs that lack p53 function rapidly become polyploid [Fukusawa et al., *Science*, 271:1744–1747 (1996); Jacks and Weinberg, *Nature*, 381:643–644 (1996); Levin, *Cell*, 88:323–331 (1997); Paulovich et al., *Cell*, 88:315–321 (1997); Lanni and Jacks, *Mol. Cell. Biol.*, 18:1055–1064 (1998)], but those that delete ARF tend to remain pseudodiploid [Kamijo et al., *Cell*, 91:641–659 (1997); Zindy et al., *Oncogene*, 15:203–211 (1997)], implying that loss of p53 contributes separately to genetic instability. In agreement, tumors arising spontaneously in ARF-null mice can subsequently sustain p53 loss, indicating that p19$^{ARF}$ and p53 can collaborate in multistep carcinogenesis [Kamijo et al., *Cell*, 91:651–659 (1997)].

Recently, two groups reported that p19$^{ARF}$ can bind to mdm2, establishing the first direct biochemical connection between p19$^{ARF}$ and p53 [Pomerantz et al. *Cell*, 92913–723 (1998); Zhang et al., *Cell*, 92:725–734 (1998)]. Mdm2 (or hdm2 in humans) is encoded by a p53-responsive gene and acts in a feedback loop [Wu et al., *Genes Dev.*, 7:1126–1132 (1993)] to limit p53 function by inhibiting its transcriptional activity [Momand et al., *Cell*, 69:1237–1245 (1992); Oliner et al., *Nature*, 362:857–860 (1993); Chen et al., *Mol. Cell. Biol.*, 13:4107–4114 (1993)] and triggering its degradation [Haupt et al., *Nature*, 387:296–299 (1997); Kubbutat et al., *Nature*, 387:299–303 (1997)]. ARF can stabilize p53 by antagonizing mdm2's effects [Pomerantz et al., *Cell*, 92:713–723 (1998); Zhang et al., *Cell*, 92:725–734 (1998)].

Materials and Methods

Cell culture: Mammalian cells were maintained in Dulbecco's modified Eagle's medium (DMEM) plus 10% fetal bovine serum (FBS), 2 mM glutamine, and 100 U/ml penicillin and streptomycin (GIBCO, Grand Island, N.Y.). Balb-3T3 (10)1 cells (ARF wild-type, p53-deleted) were a gift of Dr. Arnold Levine (Princeton Univ., Princeton, N.J.). MEFs at early passage [Mao et al., *Cancer Res.*, 55:2995–2997 (1995); stone et al., *Cancer Res.*, 55:2988–2994 (1995); Kato et al., *Genes Dev.*, 7:331–342 (1993); Ewen et al., *Cell*, 73:487–497 (1993)] were established as described [Kamijo et al., *Cell*, 91:641–659 (1997)]; those lacking p53 came from embryos of p53-null mice (Jackson Laboratories, Bar Harbor, Me.). Dr. Charles Sawyers (University of CA, LA) provided helper and vector retrovirus plasmids. Virus production and infection were performed as previously described, and growth arrest was determined by measurements of DNA content or [$^3$H]-thymidine incorporation into replicating DNA 48 hours post-infection [Quelle et al., *Cell*. 83:993–1000 (1995); Kamijo et al., *Cell*, 91:641–659 (1997)].

Spodoptera frugiperda Sf9 cells were maintained in Grace's medium supplemented with 5% FBS and infected for 48 hours with the indicated baculoviruses prior to lysis [Kato et al., *Genes Dev.*, 7:331–342 (1993)]. Baculoviruses encoding mutant forms of p53 included one (D281G) that is defective in DNA binding and another (L22Q, W23S) that cannot bind to mdm2 [Hinds et al., *Cell Growth, Diff.*, 1:571–580 (1990); Lin et al., *Genes Dev.*, 8:1235–1246 (1994)]. Flag-tagged ARF cDNA and deletion mutants containing (N62) or lacking (Δ1–62) the N-terminal 62 amino acids [Quelle et al., *Proc. Natl. Acad. Sci. USA*, 94:3436–3440 (1997)] were transferred from mammalian to baculovirus expression vectors.

Kinetics of p53 turnover: MEFs were metabolically labeled for 1 hr with 200 mCi/ml [$^{35}$S]methionine (1369 i/mmol, ICN Pharmaceuticals, Costa Mesa, Calif.), washed and refed with DMEM containing 10% FBS and 2 mM unlabeled methionine. Lysates of radiolabeled cells were immunoprecipitated, and recovered proteins were electrophoretically resolved in denaturing polyacrylamide gels [Kamijo et al., *Cell*, 91:641–659 (1997)].

Transactivation Assay: NIH-3T3 cells or Balb-3T3 (10)1 cells (5×10$^5$ cells/100 mm diameter plate) were transfected [Chen and Okayama, *Mol. Cell. Biol.*, 7:2745–2752 (1987)] with CMV-p53 [Tan et al., *J. Virol.*, 59:574–583 (1986)] or pSRαMSV-ARF/TK-CD8 [Kamijo et al., *Cell*, 91:641–659 (1997)] vectors plus 1 (g reporter plasmid encoding chloramphenicol acetyltransferase (CAT) [Kern et al., *Science*, 256:827–830 (1992)]. The reporter (PG13) contains 13 repeats of a p53-specific DNA binding site in its promoter, whereas a mutant (MG15) contains 15 altered sites unable to confer p53 binding [Kern et al., *Science*, 256:827–830 (1992)]. Carrier plasmid was used to adjust DNA concentrations to 20 μg per plate. Cells were lysed in 0.25 M Tris-HCl pH 8 by three cycles of freezing (–80° C.) and thawing (25° C.) 24 hrs after transfection. Equal quantities of protein, determined by the Bradford method (Bio-Rad Laboratories, Richmond, Calif.), were assayed for CAT activity using 0.1 μCi $^{14}$C-chloramphenicol and 4 mM acetyl coenzyme A [Gorman et al., *Mol. Cell. Biol.*, 2:1044–1051 (1982)], and separated products were detected by autoradiography [Zambetti et al., *Genes & Dev.*, 6:1143–1152 (1992)].

Electrophoretic mobility shift assay (EMSA): EMSA was performed [Friedlander et al., *J. Biol. Chem.*, 271:25468–25478 (1996)] with a synthetic double-stranded oligonucleotide (5'-AGGCATGCCTAGGCATGCCT) containing two p53 consensus binding sites, end-labeled with [$\gamma^{32}$P]-ATP using T4 polynucleotide kinase. Affinity-purified p53 (100 ng) [Wang et al., *Cell*, 57:379–392 (1989)] was mixed with lysate (1 µg protein in 5 µl EMSA buffer) from infected Sf9 cells and incubated at 25° C. for 15 minutes in the presence or absence of the p53-activating antibody, PAb421. Excess [$^{32}$P]-labeled probe (2.5×10$^5$ dpm in 1 µl) was added for 15 minutes with EMSA buffer [20 mM Hepes pH 7.9, 25 mM KCl, 0.1 mM EDTA pH 8, 2mM MgCl$_2$, 0.5 mM DTT, 0.25% Nonidet P-40, 10% glycerol, 0.1 ng BSA, and 60 ng polyd(I-C)] and adjusted to a volume of 20 µl. For competition, unlabeled probe was added in 10-fold molar excess over labeled probe. Reaction mixtures (with 0.05% bromphenol blue) were loaded onto native 4% polyacrylamide gels in 45 mM Tris Ed, 45 mM Na borate, 1 mM EDTA, 0.05% Nonidet P-40 and separated by electrophoresis at 250 V for 5 hours in the same buffer.

Protein expression and binding: Cell pellets were lysed on ice in Tween-20 lysis buffer (50 mM HEPES, pH 7.5, 150 mM NaCl, 1 mM EDTA, 2.5 mM EGTA, 0.1% Tween-20, 1 mM PMSF, 0.4 U/ml aprotinin, 10 µg/ml pepstatin, and 10 µg/ml leupeptin) and sonicated 2×7 sec (Virtis VirSonic 475, 12–14% power). Nuclei and debris were removed by sedimentation at 4° C. in a microcentrifuge (2 mm at 15,000 rpm), and protein was quantified as above. Samples (200 µg protein) electrophoretically separated on denaturing polyacrylamide gels containing sodium dodecyl sulfate (SDS) were transferred to Immobilon PDVF membranes (Millipore) pre-activated for 15 sec in methanol. Filters were washed in TBS-Tween (10 mM Tris HCl, pH7.4, 150 mM NaCl, 0.1% Tween-20) and blocked in the same solution containing 10% (w/v) nonfat dry milk. Filters exposed for 1 hr at room temperature to 0.2 µg/ml affinity-purified rabbit antibody to the mouse C-terminus [Quelle et al., *Cell*, 83:993–1000 (1995)] in TPS-Tween were washed for 45 minutes in TBS-Tween and incubated for 45 minutes with a 1/2000 dilution of donkey antibodies to rabbit IgG (Amersham) in TBS-Tween containing 5% milk. Filters were washed and antibody binding sites were visualized by enhanced chemiluminescence as per the manufacturer's instructions (ECL, Amersham).

For analysis of p53, mdm2, and p2$^{Cip1}$ expression, frozen mammalian cell pellets were disrupted in ice-cold Nonidet P-40 lysis buffer (50 mM Tris HCl, pH 8, 5 mM EDTA, 150 mM NaCl, 0.5% NP40, 1 mM PMSF, 0.4 U/ml aprotinin, 10 mM β-glycerophosphate, 1 mM NaF and 0.1 mM NaVO$_4$), and left for 1 hr on ice. Sf9 cells were lysed by scraping in cold Tween-20 lysis buffer and sonication. Centrifuged lysates were incubated for 2 hours at 4°C with antibodies against p53 (PAb421, Calbiochem, La Jolla, Calif.), mdm2 (monoclonal 2A10), or p21$^{Cip1}$ (F5, Santa Cruz Biochem., Calif.), respectively, pins 40mg/ml BSA. Complexes precipitated with protein A-Sepharose were washed three times with ice-cold Nonidet P-40 lysis buffer (for mammalian lysates) or RIPA buffer (50 mM Tris HCl, pH 8, 150 mM NaCl, 1% Triton, 0.5% sodium deoxycholate, 0.1% SDS, 1 mM PMSF, 0.4 U/ml aprotinin, 10 ug/ml pepstatin, and 10 ug/ml leupeptin) (for Sf9 lysates). Precipitates were separated on denaturing polyacrylamide gels and transferred to nitrocellulose. Mdm2 and p21$^{Cip1}$ were detected by immunoblotting with the same antibodies, and p53 with Ab-7 (Calbiochem, LaJolla, Calif.), visualized by chemiluminescence as above.

Results

Proliferating ARF-null MEFs arrest in both the G1 and G2 phase of the cell cycle when infected with an ARF-containing retrovirus [Quelle et al., *Cell*, 83:993–1000 (1995); Quelle et al., *Proc. Acad. Sci. USA*, 94:3436–3440 (1997)], which induces the cyclin-dependent kinase inhibitor p21$^{Cip1}$ in a p53-dependent manner [Kamto et al., *Cell*, 91:641–659 (1997)]. A retrovirus encoding p19$^{ARF}$ induced p53 p21$^{Cip1}$, and mdm2 proteins in these cells (FIG. 14A, lanes 1 and 2) and in wild-type MEFs, but neither p21 nor mdm2 were induced in p53-null cells [Kamijo et al., *Cell*, 91:641–659 (1997); Pomerantz et al., *Cell*, 92:713–723 (1998); Zhang et al., *Cell*, 92:725–734 (1998)]. The 62 N-terminal amino acids of mouse p19$^{ARF}$ necessary and sufficient to block proliferation [Quelle et al., *Proc. Natl. Acad. Sci. USA*, 94:3436–3440 (1997)]. Infection of ARF-null (or wild-type) MEFs with truncation mutants retaining the N-terminal 84 (N84) and 62 (N62) amino acids of p19$^{ARF}$ led to accumulation of p53, p21, and mdm2 (lanes 3 and 4), but an ARF mutant lacking amino acids 1–62 was inactive (lane 5). About two-fold elevated levels of p53 mRNA accumulated in growth-arrested cells infected with the ARF retrovirus versus those detected in uninfected proliferating cells or in cells infected with a control vector (FIG. 14B), and the half-life of the p53 protein was significantly extended from 15 to ~75 minutes by 48 hours after infection (FIG. 14C). ARF-infected cells expressed more p21 (FIG. 14B) and mdm2 mRNA than cells infected with the control virus, implying that increased levels of the latter proteins (FIG. 14A) resulted at least in part from new transcription.

ARF can interact directly with mdm2 [Pomerantz et al., *Cell*, 92:713–723 (1998); Zhang et al., *Cell*, 92:725–734 (1998)], and using Sf9 insect cells infected with baculovirus vectors encoding both proteins, binary complexes between p19$^{ARF}$ and mdm2 could be specifically precipitated using antisera to either. In addition, this assay detected direct interactions between p19$^{ARF}$ and p53 (FIG. 15). Using wild-type p53 (FIG. 15A), antiserum to p53 coprecipitated full-length p19$^{ARF}$ (~10% of input, top panel) as well as the ARF N62 mutant (middle panel), but not the ARF mutant lacking residues 1–62 (lower panel). Removal of the ARF C-terminus potentiated its interaction with p53 (compare the amount of HA-tagged N62 precipitated with anti-HA versus anti-p53). A p53 point mutant (281) impaired in DNA binding interacted as well as wild-type p53 with full-length p19$^{ARF}$ (FIG. 15B, top) and with the N62 mutant (FIG. 15B, middle); p53 (281) also retains the capability to bind mdm2 (FIG. 15B, bottom left). However, a p53 mutant (22/23/281) that does not stably interact with mdm2 (FIG. 15B, bottom right) [Lin et al., *Genes Dev.*, 8:1235–1246 (1994)] retained the ability to bind ARF (FIG. 15B, top two panels). Hence, ARF can interact with p53 directly and in the absence of mdn2.

One prediction is that ARF should form ternary complexes with mdm2 and p53 (22/23/281). In agreement, Sf9 cells co-infected with vectors encoding the three proteins yielded ternary complexes that were precipitated with antibodies to either (FIG. 15C). Ternary complexes can be formed between ARF, mdm2, and p53 under conditions where mdm2 serves as the "bridging" molecule [Pomerantz et al. *Cell*, 92:713–723 (1998); Zhang et al., *Cell*, 92:725–734 (1998)]. Our data indicate that all binary complexes are possible and that ARF can similarly recruit p53 into complexes with mdm2.

Because it is virtually impossible to assess the relative affinities p19$^{ARF}$ for mdm2 and p53 in this system, it was queried as to whether binary p19$^{ARF}$-p53 complexes could be formed in ARF-null NIH-3T3 cells undergoing ARF-induced arrest (FIG. 16A). Cells infected with ARF retrovirus and lysed 48 hours after infection were precipitated sequentially with antibodies to MYC (for non-specific binding, lane 1), twice with anti-mdm2 (lanes 2 and 3), and then with anti-p53 (lane 4). Precipitated proteins were separated and blotted with antibodies to mdm2, p19$^{ARF}$, and p53. Although p19$^{ARF}$ and some of the induced p53 coprecipitated with anti-mdm2 (lane 2), much of the remaining p53 coprecipitated with p19$^{ARF}$ in binary complexes recovered from mdm2-depleted supernatants (lane 4).

Recombinant p53 binds DNA poorly if at all, but treatment of the purified protein with an antibody (PAb 421) to a C-terminal epitope greatly enhances p53's ability to bind radiolabeled oligonucleotides containing two consensus p53 binding sites (FIG. 16, lanes 4 versus 6). The complex was competed with an excess of unlabeled oligonucleotide (lane 7). Addition of extract containing p19$^{ARF}$ to the reaction retarded the mobility of the p53-DNA complex, (lane 8), whereas p19$^{ARF}$ itself did not bind the probe (lane 3). PAb 421 was required to visualize p53-DNA complexes even when p19$^{ARF}$ was added (lane 9), indicating that ARF did not affect p53's ability to bind to DNA. The mdm2 protein did not bind the probe and its addition to reactions did not affect the mobility of any of the p53-containing complexes. Therefore p19$^{ARF}$ can bind to p53-DNA complexes in the absence of mdm2.

The effects of ARF and p53 retroviruses in MEFs lacking ARF or p53 were examined next. MEFs derived from p53-/- embryos expressed high levels of p19$^{ARF}$ but reduced levels of p21$^{Cip1}$ (FIG. 17, lane 1) as compared to matched, early-passage ARF-null (lane 2) or wild-type (lane 3) MEF strains. When infected with retrovirus encoding HA-tagged p19$^{ARF, P}$53 and p21 were induced in both ARF-positive (lane 5 versus 3) and ARF-null (lane 4 versus 2) cells, and the cells underwent growth arrest. However, p53-negative cells were refractory to ARF [Kamijo et al., Cell, 91:641–659 (1997); Pomerantz et al., Cell, 92:713–723 (1998); Zhang et al., Cell, 92:725–734 (1998)]. Infection of p53-null (lane 6) and wild-type (lane 8) MEFs with the p53 retrovirus also increased p21 expression and induced growth arrest. Reintroduction of p53 into p53-null MEFs reproducibly reduced ARF expression (lane 6 versus 1), suggesting that either protein can regulate expression of the other. Surprisingly, supra-physiologic levels of p53 protein expression obtained in p53 virus-infected, ARF-null MEFs failed to induce p21 and had very limited effects on cell proliferation (lane 7).

In ARK-null NIH-3T3 cells that retain functional p53, introduction p19$^{ARF}$ can induce the expression of a CAT reporter gene that contains wild-type p53 binding sites in its promoter (FIG. 18A, lanes 1–4; ref [Pomerantz et al., Cell, 92013–723 (1998)]). Thus, ARF induces p53-dependant transactivation without enhancing the ability of p53 to bind to DNA (FIG. 16). ARF overexpression neither affected the activity of a promoter containing mutant p53 binding sites (FIG. 18A, lanes 5–8) nor induced expression of the wild-type promoter in 10(1) cells lacking functional p53 (FIG. 18B, lanes 1–4). However, co-transfection of a construct encoding wild-type p53 into p53-null 10(1) cells induced robust CAT activity (FIG. 18B, lanes 5 and 6).

In agreement with data in FIG. 17, introduction of wild-type p53 (1–5 μg plasmid) into ARF-null NIH-3T3 cells was unable to induce p53 reporter gene expression, and, in fact, high levels repressed basal expression of the wild-type promoter (FIG. 18C, lanes 1–4). By contrast, p53-null, ARF-wt 10(1) cells were hypersensitive to p53, responding well to only 10 ng input plasmid DNA (FIG. 18B, lanes 5 and 6). To determine whether ARF might rescue p53 function in this setting, 1 μg of ARF expression plasmid was transfected, which was insufficient to fully activate the endogenous p53 response (cf. FIG. 18A, lane 2), into ARF-null NIH-3T3 cells (FIG. 18C, lane 5). Co-transfection of wild-type p53 (1–5 μg plasmid) led to increased reporter gene expression (lanes 6–8). The fact that addition of ARF can restore a p53 response in NH-3T3 cells provides direct evidence that ARF not only raises p53 levels (FIG. 14C) but also enhances its transcriptional activity through some additional mechanism.

Discussion

As confirmed herein, p19$^{ARF}$ and mdm2 proteins can physically interact with one another, as well as recruit p53 into ternary complexes [Pomerantz et al., Cell, 92:713–723 (1998); Zhang et al., Cell, 92:725–734 (1998)]. However, in both reconstituted Sf9 and ARF-infected NIH-3T3 cells, binary, mdm2-independent interactions between p19$^{ARF}$ and p53 were detected, which were mediated entirely by the N-terminal domain of ARF (amino acids 1–62) that alone is necessary and sufficient for its biologic activity [Quelle et al., Proc. Natl. Acad. Sci. USA. 94:3436–3440 (1997)]. A mutant of p53 that does not interact with mdm2 could still interact with p19$^{ARF}$, which in him was able to bind mdm2. Binding of p19$^{ARF}$ and mdm2 also requires the N-terminal domain of ARF and the C-terminal moiety of mdm2 (amino acids 208–491) [Zhang et al., Cell, 92:725–734 (1998)]. Mdm2-independent interactions between p-19$^{ARF}$ and p53 could also occur on DNA. Together, these results indicate that all binary combinations between p19 mdm2, and p53 can form, and that either mdm2 or p19$^{ARF}$ can recruit p53 into ternary complexes.

Retroviral insertion of ARF into wild type or ARF-null MEFs prolonged the half-life of the endogenous p53 protein, induced p53-dependent transcription of Cip1 and mdm2, and resulted in cell cycle arrest. By contrast, enforced expression of high levels of p53 protein activated transcription and growth arrest in wild-type or p53-null cells but were at best inefficient in doing so in ARF-null cells. Therefore, high levels of p53 per se are not sufficient to guarantee a response [for other examples, see Hupp et al., Cell, 83:237–245 (1995); Hao et al., J. Biol. Chem., 271:29380–29385 (1996); Chernov and Stark, Oncogene, 14:2503–2510 (1997); Chernov et al., Proc. Natl. Acad. Sci. USA, 95:2284–2289 (1998); Garkavtsev et al., Nature, 391:295–298 (1997)]]. To determine whether the failure of transduced p53 to function in ARF-null NIH-3T3 cells might be restored by p19$^{ARF}$ itself, low quantities of ARF retrovirus were cotransfected together with a p53-dependent CAT reporter plasmid and increasing concentrations of p53 retroviral DNA into NIH-3T3 cells. Under these conditions, levels of p19$^{ARF}$ that were insufficient to fully activate p53-dependent gene expression restored the ability of wild-type p53 to stimulate transcription. Yet, the requirement for ARF in these cells is not obligatory, since γ-irradiation of NIH-3T3 cells (or of ARF-null MEFs) induces an unimpaired p53 response [Kamijo et al., Cell, 91:641–659 (1997)]. Therefore, in addition to stabilizing p53, p19$^{ARF}$ provides another activating signal.

Inert p53 can be converted to an active DNA-binding form by antibodies to C-terminal p53 epitopes [Hupp et al., Cell, 83:237–245 (1995); Hupp et al., Cell, 71:875–886 (1992)], certain small peptides [Hupp et al., Cell, 83:237–245 (1995)], C-terminal phosphorylation [Hao et al., J. Biol. Chem., 271:29380–29385 (1996); Kapoor and Lozano, *Proc Natl. Acad. Sci. USA*, 95:2834–2837 (1998)] and acetylation [Gu and Roeder, *Cell*, 90:595–606 (1997)], and by Ref-1 protein [Jayaraman et al., *Gene Dev.*, 11:558–570 (1997)]. Yet, p19$^{ARF}$ does not fulfill this function, since ARF-p53 complexes did not bind well to DNA unless an activating antibody was added. Instead, ARF might affect p53-mediated transactivation. A significant increase in transactivation by p53 can be induced in intact cells treated with low doses of UV light without a concomitant increase in the p53 level [Hupp et al., *Cell*, 83:237–245 (1995)]. Conversely, some kinase inhibitors block p53 activation without affecting its accumulation [Chernov and Stark, *Oncoggene*, 14:2503–2510 (1997); Chernov et al., *Proc. Natl. Acad. Sci. USA*, 95:2284–2289 (1998)]. In vivo, modes of enhancing p53-dependent gene expression include phosphorylation of specific N-terminal serine residues, whose modification interferes with mdm2 binding [Shieh et al., *Cell*, 91:325–334 (1997); Siliciano et al., *Genes Dev.*, 11:3471–3481 (1997)]. Because p19$^{ARF}$ can interact with p53 on DNA, it could conceivably provide a co-activating signal of this type.

Others have suggested that p19$^{ARF}$ acts primarily on mdm2 rather than on p53 itself [Pomerantz et al., *Cell*, 92:713–723 (1998); Zhang et al., *Cell*, 92:725–734 (1998)]. Binding of mdm2 to p53 accelerates its turnover [Haupt et al., *Nature*, 387:296–299 (1997); Kubbutat et al., *Nature*, 387:299–303 (1997)], and in agreement, mdm2 has been reported to act as a p53 E3 ligase which, together with UBC6, transfers ubiquitin to p53 and promotes its proteasomal degradation [Honda et al., *Nature*, 378:203–206 (1995)]. Under normal circumstances, p53 levels are low and its turnover is rapid (t½ ~15 minutes in MEFs), but ARF overexpression, like irradiation, can significantly prolong p53's half-life (t½~75 minutes). One scenario is that p19$^{ARF}$ stabilizes p53 by increasing the rate of mdm2 turnover [Zhang et al., *Cell*, 92:725–734 (1998)], but the present data indicate that mdm2 accumulates in response to p19$^{ARF}$ expression. Induction of mdm2 by p53 serves as a feedback mechanism to limit the p53 response [Wu et al., *Genes Dev.*, 7:1126–1132 (1993)], and p53 mutants that are defective in transactivation are stable because they do not induce mdm2 [Haupt et al., *Nature*, 387:296–299 (1997); Kubbutat et al., *Nature*, 387:299–303 (1997)]. Regulation by mdm2 is critical in controlling p53, since disruption of the mdm2 gene in mice is lethal during early embryonic development unless p53 is also disabled [Montes de Oca Luna et al., *Nature*, 378:203–206 (1995); Jones et al., *Nature*, 378:206–208 (1995)].

Nuclear localization of p53 is necessary for its transcription function [Gannon and Lane, *Nature*, 349:802–806 (1991); Shaulsky et al., *Oncogene*, 6:2055–2065 (1991)], but its degradation selectively occurs in the cytoplasm [Roth et al., *EMBO J.*, 17:554–564 (1998)]. In cells enforced to express p19$^{ARF}$, high molecular weight species of p53 accumulated that likely represented polybiquitinated forms [Pomerantz et al., *Cell*, 92:713–723 (1998)], so p19$^{ARF}$ might not inhibit mdm2-mediated ubiquitination, but instead might prevent the degradation of ubiquitinated p53. An important feature of mdm2 is that it shuffles between the nucleus and the cytoplasm, and blocking its nuclear export stabilizes p53 and enhances the ability of mdm2 to block p53-mediated transcription [Roth et al., *EMBO J.*, 17:554–564 (1998)]. ARF localizes in discrete nuclear sites [Quelle et al., *Cell*, 83:993–1000 (1995)] together with mdm2 [Pomcrantz et al., *Cell*, 92:713–723 (1998)], so an attractive model is that ARF's interactions with mdm2 and p53 prevent transport from the nucleus and thereby inhibit p53 turnover. In short, although an interdependence p19$^{ARF}$ on p53 likely results from direct interactions between p53, p19$^{ARF}$ and mdm2, further mechanistic studies are clearly warranted.

Example 10

MYC Signaling via the ARF Tumor Suppressor Regulates p53-Dependent Apoptosis and Immortalization Introduction The INK4a-ARF locus is a common target of deletion and mutation inhuman cancers, possibly second infrequency only to p53. The product of the INK4a gene, p16$^{INK4a}$, acts as an inhibitor of cyclin D-dependent kinases, preventing them from phosphorylating the retinoblastoma protein (Rb) and thus inhibiting S phase entry during the cell division cycle [Serrano et al., *Nature*, 366:704–707 (1993)]. A second product of this locus, p19$^{ARF}$ encoded in part by an alternative reading frame of INK4a exon-2, is completely unrelated in its primary structure to p16$^{INK4a}$ and induces both G1 and G2 phase arrest in rodent fibroblasts [Quelle et al., *Cell*, 83:993–1000 (1995b)) in a p53-dependent manner [Kamijo et al., *Cell*, 91:641–659 (1997)]. Thus, both p16$^{INK4a}$ and p19$^{ARF}$ act as potent tumor suppressors by targeting Rb and p53 function, respectively.

Establishment of mouse embryo libroblasts (MEFs) as continuously growing cell lines is usually accompanied by either ARF or p53 loss-of-function, implying that the two proteins act epistatically in a single pathway [Kamijo et al., *Cell*. 91:641–659 (1997); Zindy et al., *Oncogene*, 15:203–211 (1997)]. The p53 protein is a transcription factor [Kern et al., *Science*, 256:827–830 (1992)] that induces several known target genes, including the cyclin-dependent kinase inhibitor p21$^{Cip1}$/Waf1 [El-Deiry et al., *Cell*, 75:817–825 (1993); Harper et al., *Cell* 75:805–816 (1993); Xiong et al., *Nature*, 366:701–704 (1993)] and mdm2 [Barak et al., *EMBO J.*, 12:461–468 (1993); Wu et al., *Gene. Dev.*, 7:1126–1132 (1993)]. In turn, mdm2 acts in a feedback loop to catalyze p53 ubiquitination and degradation, limiting the p53 response [Haupt et al., *Nature*, 387:296–299 (1997); Kabbutat et al., *Nature*, 387:299–303; Honda et al., *FEBS Lets.*, 420:25–27 (1997)]. The ARF protein can physically interact in binary or ternary complexes with p53 and mdm2, and its overexpression induces p53 stabilization and activates p53-dependent transcription [Pomerantz et al., *Cell*, 92:713–723 (1998); Zhang et al., *Cell* 92:725–734 (1998); Example 9. above]. Although the levels of p19$^{ARF}$ expressed in normal MEFs are relatively low, an unexplained feature is that p19$^{ARF}$ expression is significantly elevated in p53-null fibroblasts [Quelle et al., *Cell*, 83:993–1000 (1995b)]. Conversely, reintroduction of p53 into p53-null cells returns the level of p19$^{ARF}$ to normal levels [Example 9, above]. Together, these data suggest that a feedback loop also acts to limit p19$^{ARF}$ expression once p53 is activated, and the ability of mdm2 to bind both p53 and p19$^{ARF}$ raises the possibility that mdm2 may be responsible for their joint downregulation.

The physiologic signals that induce ARF remain unknown. ARF is dispensable for p53 activation in response to ionizing or ultraviolet radiation [Kamijo et al., *Cell* 91:641–659 (1997)], suggesting that it does not function in a DNA damage signaling pathway. Observations that ARF-null MEFs are immortal and can be transformed by oncogenic Ras alleles without a requirement for collaborating oncogenes such as MYC and adenovirus E1A [Kamijo et al., Cell, 91641–659 (1997)] led us to consider the possibility that MYC and E1A might regulate p19$^{ARF}$ function. Either of these oncogenes are capable of immortalizing primary rodent fibroblasts [Land et al., Nature, 304:596–602 (1983); Ruley, Nature, 304:602–606 (1983)]. Whether induced by enforced MYC or E1A expression, chemical carcinogens, or by loss of p53 or ARF function, establishment and immortalization enable MEFs to be transformed into tumor cells by oncogenic Ras genes alone [Land et al., Nature 304:596–602 (1983); Newbold and Overall, Nature, 304:648–651 (1983); Ruley, Nature, 304:602–606(1983); Ruley, In Cancer Cells 2, Woude, Levin, Topp & Watson eds., Cold Spring Harbor Press, pp. 258–268 (1990); Hicks et al., Mol. Cell Biol., 11:1344–1352 (1991); Lin et al., Mol. Cell Riot, 15:4536–4544 (1995); Serrano et al., Cell, 85:27–37(1996); Kamijo et al., 91:641–659 (1997)]. MYC and E1A seem to inactivate cellular responses that are normally required for Ras-mediated inhibition, of cell proliferation, thereby converting lies into a growth-promoting gene [Franza et al., Cell, 44:409–418 (1986); Hicks et al., Mol. Cell Biol., 11:1344–1352 (1991); Hirakawa and Ruley, Proc. Natl. Acad. Sci. USA, 85:1519–1523 (1991)].

Given their apparent immortalizing functions, it seems paradoxical that MYC and E1A are also potent inducers of apoptosis [Askew et al., Oncogene, 6:1915–1922 (1991); White et al., J. Virol., 65:2968–2978 (1991); Evan et al., Cell, 69:119–128 (1992); Rao et al., Proc. Natl. Acad. Sci. USA, 89:7742–7746 (1992)]. The sensitivity of rodent fibroblasts to MYC- or E1A-induced apoptosis correlates directly with the levels of oncoprotein expression and is greatly potentiated by depriving cells of extracellular survival factors [Evan et al., Cell, 69:119–128(1992); [Lowe and Ruley, Genes Dev., 7:535–545 (1993)]. Both MYC and E1A can induce p53 stabilization and trigger p53-dependent transcription [Lowe and Ruley, Genes Dev., 7:535–545 (1993); Hermeking and Eick, Science, 265:2091–2093 (1994); Wagner et al., Genes Dev., 8:2817–2830 (1994)]. Several lines of evidence indicate that p53 mediates apoptosis by MYC and E1A in primary fibroblasts, with p53 loss rendering cells highly resistant to their deleterious effects [Debbas and White, Genes Dev.. 7:546–554 (1993); Lowe and Ruley, Genes Dev., 7:535–545 (1993); Hermeking and Eick, Science, 265:2091–2093 (1994); Wagner et al., Genes Dev., 8:2817–2830 (1994)]. In order for cells overexpressing MYC to grow, programmed cell death must be actively suppressed Askew et al., Oncogene, 6:1915–1922 (1991); Evan et al., Cell, 69:119–128 (1992); Hermeking and Eick, Science, 265:2091–2093 (1994); Wagner et al., Genes Dev., 8:2817–2830 (1994)]. Therefore, MYC overexpression should provide a strong selective pressure for events that dismantle apoptotic signaling pathways.

Materials and Methods

Cell culture: MEFs from day 14.5 embryos (wild-type, ARF-null, p53-null, p21-null) or day 13.5 embryos (Rb-null) were explanted and maintained on a 3T9 protocol (9×10$^5$ cells transferred at 3 day intervals) [Kamijo et al., Cell, 91:641–659 (1997)] and propagated in Dulbeeco's modified Eagle's medium (DMEM) plus 10% fetal bovine serum, 2 mM glutamine, 0.1 mM nonessential amino acids, 55 uM 2-mercaptoethanol, and 10 μg per ml gentamycin (Grand Island, N.Y.). ARF-null cells were established by standard procedures. MEFs from p53-null cells were derived from mice purchased from Jackson laboratories. Timed p21-null and Rb-null pregnant females were generously provided by Stephen Elledge (Baylor College of Medicine) and Tyler Jacks (MIT), respectively. Where indicated, cultured MEFs at passage 5 were switched to defined, serum-free medium containing insulin, transferring, and bovine serum albumin as the only added proteins [Roussel and Sherr, Proc. Natl. Acad. Sci. USA, 86:7924–7927 (1989)]. At the same time, cells infected for 48 hours with the indicated reboviruses were diluted and plated at 2×10$^4$ cells per 60 mm diameter dish in 4 ml complete medium. The following day, fresh medium containing or lacking serum was added, and cells from replicate cultures were counted every day thereafter. Viability was determined by trypan blue exclusion, and DNA fragmentation was monitored using a terminal deoxynucleotidyl transferase (FACS TUNEL) assay [Gorczya et al., Cancer Res., 53:1945–1951 (1993)] and by measurement of subdiploid (<2N) DNA content of propidium iodide-stained nuclei [Askew et al., Oncogene, 6:1915–1922 (1991)]. Where indicated, cells grown for 10–14 days post-infection in complete serum-containing medium were diluted as above and their kinetics of proliferation and survival in serum-free medium were re-assessed.

Cells bemizygous for a functional ARF allele were infected with MYC retrovirus, and four days post-infection were transferred into serum-free medium for two days. Survivors were plated in complete medium at limiting dilution in 96-well microtiter plates, and 26 clones derived from single cells were expanded and assayed for p19$^{ARF}$ and p53 protein as shown in FIG. 24B. Cells lacking p19$^{ARF}$ were confirmed by Southern blotting to have segregated the residual wild-type allele. The presence of mutant and wild-type p53 was confirmed by immunoprecipitation of metabolically labeled cell lysates with conformation-specific antibodies (see below).

Virus injection: Human kidney 293T cells were from Dr. David Baltimore. A helper ecotropic retrovirus plasmid defective in psi-2 packaging sequences, and pSRα vectors containing human c-myc [Roussel et al., Proc. Natl. Acad. Sci. USA, 92:6837–6841 (1995)] and CDS [Quelle et al., Cell, 83:993–1000 (1995b)] were provided by Dr. Charles Sawyers (UCLA). The human E2F1 cDNA provided by Dr. Scoff Hiebert (Vanderbilt University, Nashville Tenn.) or oncogenic Ha-ras (va112) cDNA from Dr. Michael M. White (Southwestern Med. Ctr., Dallas Tex.) were cloned into the same vector in place of c-myc. A MYC-™ retroviral vector containing a linked gene for puromycin-resistance was provided by Drs. Dean Flesher and J. Michael Bishop (UCSF). The ER™ moiety is unable to bind estrogen yet retains its affinity for the synthetic ligand, 4-hydroxytamoxifen [Littlewood et al., Nucleic Acids Res., 23:1686–1690 (1995)]. The cDNA cassette encoding MYC-ER™ was also expressed in the pSRα vector and MEFs infected with this retrovirus yielded similar results to those shown in FIGS. 21 and 22B. Viruses produced by cotransfection of 293T cells with vector and helper virus plasmids [Roussel et al., Proc. Natl. Acad. Sci. USA, 92:6837–6841 (1995)] were harvested every six hours 24–72 hours after transfection. Pooled, filtered supernatants (three successive additions of 2 ml at 4 hour intervals) were used to infret naive primary MEF strains (2×10$^5$ cells plated per 100 mm diameter dishes) in the presence of 10 μg/ml polybrene (Sigma, St. Louis Mo.). At 12 hours post-infection, 10 ml fresh medium was added, and medium was changed 24 hours later. Cells infected with MYC-ER™ virus were selected in 2 μg/ml puromycin for 48 hours prior to treatment of surviving cells with 1 μM 4-hydroxytanoxifen for times indicated in the figures.

RNA and Protein expression: Total RNA was electrophoretically separated in gels containing formaldehyde (20

μg per lane), blotted to nitrocellulose, and detected using [$^{32}$P]-labeled probes specific for exons 1α (INK4a) and 1β (ARF) of the mouse ARF-INK4a locus [Quelle et al., Cell, 83:993–1000(1995b); Zindy et al., Oncogene, 15:203–211 (1997)]. Proteins were detected by direct immunoblotting. Frozen cell pellets (~2 mg protein) were lysed on ice in Tween-20 lysis buffer (50 mM HEPES, pH 7.5, 150 mM NaCl, 1 mM EDTA, 2.5 mM EGTA, 0.1% Tween-20, 1 mM PMSF, 0.4 U/ml aprotinin, 1 mM NaF, 10 mM β-glycerophosphate and 0.1 mM Na orthovanadate), sonicated 2×7 sec (Virtis VirSonic 475, 12–14% power), and left on ice for 30 minutes. Debris was removed by sedimentation at 4EC in a microcentrifuge (5 min at 15,000 rpm), and protein was quantitated using a BCA kit (Pierce, Rockford Ill.). Samples (200 μg protein per lane) electrophoretically separated on denaturing polyacrylamide gels containing sodium dodecyl sulfate (SDS) were transferred to nitrocellulose membranes (MSI, Westboro Mass.). Filters were washed in TBS-Tween (10 mM Tris HCl, pH 7.4, 150mM NaCl, 0.1% Tween-20) and blocked in the same solution with 10% W/v nonfat dry milk. Filters were then exposed for 1–2 hr at room temperature to either 0.2 ug/ml affinity purified rabbit antibody to the mouse p19$^{ARF}$ C-terminus [Quelle et al., Cell 83:993–1000(1995b)] or p16$^{INK4a}$ C-terminus [Quelle et al., Oncogene, 11:635–645 (1995a)]; rabbit antiserum to E2E-1 (from Scott Hiebert); or monoclonal antibodies directed to p53 (Ab-7, Calbiochem La Jolla Calif.), mdm2 (2A10 provided by Gerard Zambetti, St. Jude Children's Rsch. Hosp.), p21$^{Cip1}$ (F-5, Santa Cruz Biochemicals, Santa Cruz Calif.), human MYC (06340, Upstate Bio. Inc) or p21$^{ras}$ (rat mAb 259, Santa Cruz Biochemicals). Those filters exposed to affinity-purified rabbit antibodies to p19$^{ARF}$ were washed for 45 minutes in TBS-Tweet and incubated 45 minutes with a 1/2000 dilution of donkey antibodies to rabbit IgG (Amersham) in TBS-Tween containing 5% milk. All filters were then rewashed as above and antibody binding sites were visualized by enhanced chemiluminescence using appropriate second antibody conjugates or horse radish peroxidase conjugated protein A (for p16$^{INK4a}$) as per the manufacturer's instructions (ECL kit, Amersham). For discrimination of mutant and wild-type forms of p53, cells were metabolically labeled with [$^{35}$S]-methionine, lysed, and cleared lysates were precipitated with antibodies that detect either mutant or wild type forms of the protein [Gannon et al., EMBO J., 9:1595–1602 (1990); Yewdell et al., J. Virol., 59:444–452 (1986)] as described previously [Kamijo et al., Cell, 91:641–659 (1997)].

Results

ARF is induced by explanting MEFs into culture: ARF is not detectably expressed during mouse embryogenesis, and disruption of the gene has no effect on development [Zindy et al., Oncogene, 15:203–211 (1997); Kamijo et al., Cell, 91:641–659 (1997)]. However, when MEFs were explanted into culture and cells were serially transferred on a three-day schedule (3T9 protocol), p19$^{ARF}$ was induced at early passages and increased steadily thereafter (FIG. 19. wild-type MEFs). Its accumulation inversely correlates with the rate of MEF cell proliferation, which gradually slows and eventually ceases as cells reach replicative "crisis" (passages 17–20 on this protocol) [Kamijo et al., Cell, 91:641–659 (1997)]. Expression of p19$^{ARF}$ in p53-null MEFs was elevated and temporally advanced as compared to that in wild-type cells (FIG. 19), consistent with the ability of ARF and p53 to regulate each other's levels and activities (see Introduction). In contrast, the loss of p21$^{Cip1}$, a p53-responsive gene product that negatively regulates progression through the cell cycle [El-Deity et al., Cell, 75:817–825 (1993); Harper et al., Cell, 75:805–816 (1993); Xiong et al., Nature, 366:701–704 (1993)], did not affect ARF levels (FIG. 19).

Although expression of p19$^{ARF}$ in MEFs could connote a role in replicative senescence, the basis for its accumulation was puzzling. One clue was provided by observations that Rh-null MEFs greatly overexpressed p19$^{ARF}$ (FIG. 19), possibly reflecting a propensity of Rb-regulated E2F transcription factors to influence ARF gene expression. Indeed, previous survey of INK4a responses to various E2F family members noted that the level of ARF mRNA rose in response to infection of REF52 cells by adenoviruses encoding E2F-1 and, to a lesser extent, F2F-2, but not those specifying E2Fs 3, 4, or 5 [DeGregori et al., Proc. Natl. Acad. Sci. USA, 94:7245–7250 (1997)]. Secondly, the ability of ARF-null MEFs to grow continuously and to be transformed by Ras alone mimics the effects of MYC and E1A on normal MEFs [Land et al., Nature, 304:596–602 (1983); Ruley, Nature, 304:602–606 (1983)]. This led us to the idea that some immortalizing function of MYC might be dispensable in ARF-null cells. The underlying hypothesis is that ARF normally functions to safeguard cells against sustained and potentially oncogenic hyperproliferative signals (as opposed to DNA damage), thereby explaining why its loss strongly predisposes to tumor development.

Induction of ARF by MYC: The effects of ectopic MYC, Ha-ras (Val-12) and E2F-1 on ARF gene expression were examined by infecting early passage (p5) MEFs with retrovirus vectors expressing these genes, or with a control vector expressing the T cell co-receptor CD8. Wild-type ARF-null, and p53-null cells were infected three times at four hour intervals with high titer replication-defective viruses. By 48 hours after infection, more than 95% of MEFs infected with the control virus expressed cell surface CD8, as determined by fluorescence-activated flow cytometry (FACS) using a cognate antibody, indicating that virtually all cells were produced infected.

Patterns of various RNAs and proteins expressed 48 hours after infection are illustrated in FIGS. 20A and 20B, respectively. When wild-type MEFs were infected with MYC virus, induction of ARF mRNA was observed without significant changes in the levels of INK4a transcripts (FIG. 20A, lanes 1 and 2). This correlated with increased expression of p19$^{ARF}$ protein without an observable change in p16$^{INK4a}$ (FIG. 20B lane 2 versus 1). Thus, MYC selectively induced ARF expression within the first two days after infection. Ectopic MYC expression led to two-fold increases in p53 mRNA levels (FIG. 20A, lanes 1 and 2) [Roy et al., Mol. Cell. Biol., 14:7805–7815 (1994); Hermeking and Eick, Science, 265:2091–2093 (1994)] and to 8–10 fold increases in p53 protein (FIG. 20B, lanes 1 and 2), resulting from p53 stabilization. This was accompanied by accumulation of the p53-responsive gene products, mdm2 (FIG. 20B, lane 2), and p21$^{Cip1}$ (see FIG. 21, below). By contrast, effects of MYC overexpression was not observed for the levels of the Bcl-2 or Bax proteins. Infection of wild-type MEFs with a retrovirus vector encoding oncogenic Ha-ras did not affect expression of p19$^{ARF}$, p53, or mdm2, although a slight increase in p16$^{INK4a}$ levels by 48 hours post-infection were observed (FIG. 20B, lane 3). Virtually all wild-type MEFs infected with E2F-1 virus died by apoptosis within 48 hours after infection [Qin et al., Proc. Natl. Acad. Sci. USA, 91:10918–19022(1994); Shan and Lee, Mol. Cell. Biol., 14:8166–8173 (1994); Wu and Levine, Proc. Natl. Acad. Sci. USA, 91:3602–3606(1994)], preventing the assaying of the p19$^{ARF}$ protein levels under these conditions.

To assess whether MYC's effects on p53 were ARF-dependent, ARF-null MEFs were infected with MYC retrovirus. Here, the introduction of MYC also increased expression of p53 mRNA (FIG. 20A lanes 3 and 4) and both p53 and mdm2 proteins (FIG. 20B, lanes 4 and 5), indicating that the ability of MYC to induce p53 was, at least in part, ARF-independent. Again, oncogenic Ras had no such effects (FIG. 20B, lane 6). As reported previously, $p16^{INK4a}$ levels are elevated in ARF-null cells [Kamijo et al., Cell, 91:641–659 (1997)], and in this setting, neither Ha-ras nor MYC appeared to regulate the protein (FIG. 20B, lanes 5 and 6).

Although p53-null express relatively high basal levels of $p19^{ARF}$ their infection by MYC retrovirus further augmented the levels of ARF mRNA (FIG. 20A, lanes 5 versus 6) and protein (FIG. 20B, lane 9 versus 8). In four such experiments using p53-null MEFs, enforced MYC expression reproducibly elevated $p19^{ARF}$ levels 1.5 to 3 fold, implying that MYC can induce ARF via a p53-independent pathway. In contrast, mdm2 (FIG. 20B, lane 9) and $p21^{Cip1}$ (shown in FIG. 21, see below) were not induced in p53-null cells, indicating that their tip-regulation by MYC was strictly p53-dependent. Interestingly, ARF-null cells, like p53-null cells [Qin et al., Proc. Natl. Acad. Sci. USA. 91:10918–19022 (1994); Shan and Lee, Mol. Cell. Biol., 14:8166–8173 (1994); Wu and Levine, Proc. Natl. Acad. Sci. USA, 91 :3602–3606 (1994)], were partially resistant to killing by E2F-1, and therefore E2F-1 overexpression on a per protein basis (FIG. 20B, lanes 7 and 10) could be documented. Like MYC, E2 F-1 induced both p53 and mdm2 (lane 7), and mdm2 induction was p53-dependent (lane 10). Importantly E2F-1 induced $p19^{ARF}$ in $p^{53}$-null cells to a level somewhat higher than that seen in MYC-infected cells (lanes 10 versus 9), while the amounts of $p16^{INK4a}$ were diminished (lanes 7 and 10). Thus, E2F-1, like MYC, induced both $p19^{ARF}$ and p53, and triggered mdm2 expression in a p53-dependent manner.

To determine the kinetics of the MYC response, MEFs were infected with a retrovirus vector encoding MYC fused to the 4-hydroxytamoxifen (4-hT)-responsive domain of the estrogen receptor (ER™) [Littlewood et al., Nucleic Acids Res., 23:1686–1690 (1995)] together with a linked gene encoding resistance to puromycin. Following selection of infected cells for two days with puromycin under conditions where all uninfected MEFs are killed. 4-hT was added to the medium and cells were assayed for $p19^{ARF}$ and p53 protein expression as MYC activity was induced. FIG. 21 shows a representative experiment comparing wild-type, ARF-null, and p53-null cells. Ectopic Myc-ER™ protein levels were equivalent in the three cell lines. In wild-type MEFs, 1.8 fold induction of $p19^{ARF}$ was observed within 3 hours of 4 hT treatment, rising to 8.5 fold above the basal level by 24 hours (FIG. 21, lanes 1–5). Induction of p53 was more protracted with a significant elevation (1.8 fold) occurring six hours after addition of 4-hT and reaching a maximum (3-fold above basal levels) by 12 hours of treatment. Both mdm2 and $p21^{Cip1}$ were induced with kinetics similar to that of p53 (lanes 1–5), but as expected, were not induced in p53-null cells (lanes 11–15). In these experiments, the constitutively high levels of $p19^{ARF}$ expressed in p53-null cells were not further increased upon 4-hT treatment (lanes 11–15).

In ARF-null cells expressing MYC-ER™, p53 levels rose only two-fold during the same induction period, in agreement with the concept that p53 induction is partially ARF-dependent (FIG. 21, lanes 6–10). In accord with these findings, induction of the p53-responsive mdm2 protein was attenuated (lanes 6–10). Basal levels of $p21^{Cip1}$ are significantly reduced in ARF-null cells (lane 6; see Kamijo et al, [Cell, 91:641–659 (1997)]), and, surprisingly, no induction of $p21^{Cip1}$ was seen in response to 4-hT treatment (lanes 6–10). These differences in p53 response between wild-type and ARF-null MEFs were observed in independent experiments using two different MYC-ER™ containing vectors (see Methods). Therefore MYC rapidly induced $p19^{ARF}$, but in its absence, p53, mdm2, and $p21^{Cip1}$ induction were all significantly impaired. Taken together, the above data indicate that: (i) MYC induces ARF via p53- and mdm2-independent pathways; (ii) MYC likely up-regulates p53 through both ARF-dependent and independent pathways: and (iii) MYC induction of mdm2 and $p21^{Cip1}$ is strictly dependent upon p53.

ARF loss attenuates MYC-induced apoptosis: Apoptosis induced by MYC in fibroblasts deprived of serum survival factors [Evan et al., Cell, 69:119–128 (1992)] depends upon p53 [Hermeking and Eick, Science, 265:2091–2093 (1994); Wagner et al., Genes Dev., 8:2817–2830 (1994)]. Since MYC increased the levels of both $p19^{ARF}$ and p53, MYC's ability to trigger apoptosis might also be ARF-dependent. Cells in which the biochemical consequences of MYC overexpression had been documented two days post-infection (FIG. 20) were expanded in culture for two additional days and then shifted into chemically defined medium containing insulin, transferrin, and bovine serum albumin as the only exogenously added proteins. Under serum-free conditions, MYC-infected wild-type MEFs rapidly underwent apoptosis as defined by propidium iodide staining for subdiploid DNA content, visualization of nuclear condensation and blebbing in Hoescht 33342-stained cells, determination of membrane integrity by vital dye exclusion, and TUNEL FACS analysis (FIG. 22A). Similarly, a majority of wild-type MEFs that had been infected with MYC-ER™ virus and induced with 4-hT for 24 hours (FIG. 21) died by apoptosis within a day after transfer to serum-free medium (FIG. 22B, closed symbols). Previously uninduced cells that were shifted into serum-free medium containing 4-hT for 24 hours also died (FIG. 22B, open symbols). In each ease, p53-null cells were highly resistant to MYC-induced apoptosis, whereas the apoptotic response of ARF-null cells was less compromised (FIGS. 22A and 22B).

To explore longer term effects, cells infected for four days with MYC- or control CD8 vectors were propagated in either serum-containing or serum-free medium, and their growth rates were determined (FIG. 23). Early passage (p5) wild-type MEFs infected with control CD8 virus proliferated in medium containing serum (FIG. 23A, closed circles), yet underwent only one population doubling in seven days when serum was removed (FIG. 23A, open circles). More than 85% of serum-deprived cells remained viable and arrested in the G1 phase of the cell cycle. However, as first reported by others [Evan et al., Cell, 69:119–128 (1992)], MYC-infected MEFs harvested four days after infection proliferated less well in the presence of serum (FIG. 23A, closed squares) and had a considerably higher apoptotic index (10–15% TUNNEL-positive), so that their rate of growth was in part counterbalanced by cell death. When they were shifted to serum-free medium, cells ectopically expressing MYC underwent apoptosis rapidly (FIG. 23A, open squares). After only 24 hours, the majority were already dead (FIGS. 22A and 23), and by 4 days, no viable cells remained.

Early passage (p5) ARF-null and p53-null MEFs grew somewhat more rapidly than their wild-type counterparts in the presence of serum (FIGS. 23B and 23C, closed circles), but still exited the cell cycle when deprived of serum (FIGS. 23B and 23C, open circles). Although MYC-infected ARF-null cells transferred to serum-free medium initially underwent apoptosis, a significant fraction survived and continued to proliferate (FIG. 23B, open squares). By 14 days after infection, these cells were completely resistant to MYC-induced apoptosis and grew as rapidly in serum-free medium as did uninfected cells propagated in the presence of serum (FIG. 23B, open triangles). Cells lacking p53 were even more resistant to MYC-induced apoptosis, undergoing less cell death than ARF-null cells in the first few days after infection (FIG. 23C). All resistant populations continued to ectopically express MYC protein (see FIG. 24, below), confirming that they had been infected. Hence, the effects of MYC on apoptosis were significantly attenuated in the absence of ARF or p53 function, and after a few days of selection in serum-free medium, MYC ultimately acted as a pure growth promoter.

Although ARF-null and p53-null cells were relatively resistant to MYC-induced apoptosis, their response was biphasic. Significant fractions were killed in the first few days after MYC virus infection and serum withdrawal, after which resistant cells grew out. Acute phase killing was more severe in ARF-null than in p53-null cells (FIGS. 23B and 23C, open squares), consistent with MYC's ability to target p53 through an ARF-independent pathway (see above). In addition, very high levels of MYC were achieved in the first 1–3 days after infection but declined as infected MEFs were propagated, and were reduced by almost 80% by the time that cells became completely resistant to apoptosis (~day 14) (but see FIG. 24 below). Acutely elevated levels of MYC also killed a fraction of p53-null cells (FIG. 22A), accounting for their initial growth lag in serum-free medium (FIG. 23C, open squares). A critical issue is whether MYC overexpression could have selected for additional genetic changes that obviated a requirement for ARF function. To test this possibility, the ARF gene was introduced into surviving ARF-null MYC overexpressors that had acquired the ability to proliferate in serum-free medium. Reinfection of these cells with an ARF but not control CD8 retrovirus resensitized them to apoptosis in serum-free medium (42% viability in ARF-infected cells versus >90% in CD8-infected cells at 24 hours post-infection).

Therefore, resistance to apoptosis was a direct consequence of ARF loss and was not due to mechanisms that bypass ARF function.

MYC-induced apoptosis selects for cells that lose either p53 or ARF function: Since MYC overexpression in wild-type MEFs induces apoptosis and slows their overall proliferative rate in serum-containing medium (FIG. 23A, closed symbols), it appears that continued passage of these cells might select for resistant, more rapidly proliferating variants that spontaneously lose ARF or p53 function. MYC virus-infected wild-type strains maintained in serum-containing medium and studied 7–10 days after infection initially remained sensitive to apoptosis when deprived of serum. By this time, the cells synthesized very high levels of p19$^{ARF}$ (FIG. 24A, lanes 2 and 3) equivalent to those seen in p53-null cells (lane 9). To distinguish wild-type from mutant p53, cells were metabolically labeled with [$^{35}$S]-methionine for two hours, and lysates were precipitated using conformation-specific antibodies [Yewdell et al. *J. Virol.*, 59:444–452(1986); Gannon et al., *EMBO J.*, 9:1595–1602 (1990)]. MYC infection increased the rate of wild-type p53 synthesis (FIG. 24A, lanes 2 and 3 versus 1), consistent with induction of p53 mRNA (FIG. 20A). Because of its longer half-life, the steady state levels of p53 in MYC-infected versus CD8 virus-infected cells, as judged by immunoblotting, differed even more significantly (FIG. 20B). At this time after infection, no mutant forms of p53 were detected (lanes 2 and 3).

By 14–21 days after infection wild-type MEFs infected with MYC virus and maintained in medium containing serum no longer underwent apoptosis when transferred to serum-free medium and continued to proliferate as established cell lines. Emerging variants were readily identified by their much smaller size (1.11 pL versus 3.3 pL mean corpuscular volume), accelerated growth rate, and their ability to proliferate in serum-free medium. Four such independently derived cell lines expressed mutant, dominant-negative forms of p53 in addition to the wild-type form of the protein (FIG. 24A, lanes 4 and 5 show results with two such lines). By contrast, MYC-infected ARF-null cell lines growing in serum-free conditions expressed only wild-type p53 (FIG. 24A, lanes 7 and 8). Therefore, MYC-induced immortalization of wild-type cells selected for p53 loss-of-function, but such selection was obviated in cells lacking ARF.

In general, ARF-null cells tolerated higher levels of ectopic MYC protein than did wild-type MEFs that had acquired p53 mutations in the course of infection (compare MYC levels in lanes 7 and 8 with those in lanes 4 and 5). Moreover, wild-type MEFs that were initially sensitive to MYC-induced apoptosis expressed higher levels of MYC than did resistant variants (compare MYC levels in lanes 2 and 3 versus 4 and 5). These results are consistent with the idea that high levels of MYC are selected against by apoptosis until resistant variants emerge.

In continuing studies of spontaneously immortalized wild-type MEFs that emerged from crisis on a 3T9 protocol, it was determined that 23 of 28 individually derived cell lines had sustained p53 mutations, whereas the remainder exhibited bi-allelic loss of ARF. In principle, bi-allelic ARF loss might also occur during MYC-induced establishment, but this should again be a less frequent event than p53 mutation, involving two-hit versus one-hit kinetics [Zindy et al., *Oncogene*, 15:203–211 (1997); Kamijo et al., *Cell*, 91:641–659 (1997)]. Moreover, because MYC virus-infected populations are polyclonal, attempts to demonstrate bi-allelic ARF loss in a subset of cells would be occluded by the presence of other cells in the population containing mutant p53 and expressing high levels of p19$^{ARF}$. To determine whether ARF-loss can also occur in response to enforced MYC expression, MEFs hemizygous for a wild-type ARF allele were infected with MYC virus, propagated in serum-free medium for two days, and then shifted back into medium containing serum. Surviving cells were subcloned by limiting dilution, expanded, and then assayed for p19$^{ARF}$ expression and for the presence of wild-type and mutant p53. Eleven of 26 clones exhibited p53 mutations, whereas the other 15 lacked detectable p19$^{ARF}$. FIG. 24B shows results with 13 representative clones designated A to M. Mutant p53 was expressed at high levels (clones A-E and I) compared to those in uninfected wild-type (wt) MEFs. As expected, clones with mutant p53 also expressed higher levels of p19$^{ARF}$ than wild-type cells. In contrast, ARF-null variants (clones F-H and J-M) expressed low levels of wild-type p53. Southern blotting confirmed the loss of the wild-type ARF allele in the latter cases. Therefore, immortalization of wild-type MEFs by MYC leads to either ARF or p53 loss and confers resistance to MYC-induced apoptosis.

Discussion

Signaling to ARF and p53: Cells protect themselves from mutant cancer genes (i.e., mutated oncogenes or loss of tumor suppressors) through compensatory mechanisms that arrest cell growth or induce cell suicide [reviewed in Sherr, Science, 274:1672–1677 (1996); Weinberg, Cell, 88:573–575 (1997)]. Expression of activated Ras in primary MEFs inhibits cell growth [Serrano et al., Cell, 88:593–602 (1997)], whereas overexpression of MYC in these same cells triggers apoptosis, a process further aggravated by withdrawal of serum survival factors [Evan et al., Cell, 69:119–128 (1992)]. Yet, introduction of MYC and Ras together into primary rodent embryo fibroblasts elicits cell transformation [Land et al., Nature, 304:596–602 (1983)]. MYC must somehow block Ras-mediated inhibition of cell proliferation, while conversely, Ras may play a role in attenuating the apoptotic function of MYC [Weinberg, Cell, 88:573–575 (1997)].

One hypothesis is that cultured cells achieve replicative immortality by inactivating their $p16^{INK4a}$ or p53 genes [reviewed in Weinberg, Cell, 88:573–575 (1997)]. To some extent, this idea was based on the ability of MEFs from INK4a/ARF-null mice to grow continuously after explantation into culture and to be transformed by oncogenic Ras alone [Serrano et al., Cell, 85:27–37 (1996); Serrano et al., Cell, 88:593–602 (1997)]. Yet, MEFs from mice lacking ARF alone exhibit the immortalized features previously attributed to disruption of INK4a, implying that loss of $p19^{ARF}$ in lieu of $p16^{INK4a}$ enables oncogenic Ras alleles to transform these cells. Given that Ras positively regulates the synthesis of D-type cyclins and their assembly with CDK4 [Cheng et al., Proc. Natl. Acad. Sci. USA, 95:1091–1096 (1998), and references therein], a role for $p16^{INK4a}$ in antagonizing these growth promoting activities of Ras would be expected (see FIG. 25 for schematic). Pomerantz et al., [Cell, 92:713–723 (1998)] recently demonstrated that overexpression of $p19^{ARF}$ in rat embryo fibroblasts transformed by Myc plus Ras was significantly more potent than $p16^{INK4a}$ in suppressing transformation. Moreover, they found that $p19^{ARF}$, but not $p16^{INK4a}$, suppressed transformation by E1A plus Ras in a p53-dependent manner, consistent with the idea that $p19^{ARF}$ acts downstream of Rb (and E2F-1) in countering oncogenic signaling (FIG. 25). Therefore either $p19^{ARF}$ or p53 inactivation provides an immortalizing function that mimics certain actions of Myc and E1A and renders primary MEFs more susceptible to Ras-induced transformation. Clearly, this model does not preclude a requirement for other growth promoting functions of MYC and E1A in immortalizing wild-type cells.

Overexpressed MYC car signal through $p19^{ARF}$ and p53 to trigger apoptosis, although its effects can be overridden by serum survival factors (FIG. 25). Overexpression of MYC induces the accumulation of $p19^{ARF}$, at least in part by increasing ARF gene expression. Induction of $p19^{ARF}$ synthesis by a conditionally active MYC-ER™ fusion protein occurred within 3 hours of 4-hydroxytamoxifen treatment and temporally preceded p53 accumulation and p53-dependent expression of mdm2 and $p21^{Cip1}$. Although MYC can induce p53 through an ARF-independent pathway, its induction of p53 and p53-responsive gene products is significantly compromised in ARF-null cells. For unexplained reasons, greater attenuation of the $p21^{Cip1}$ response than that of mdm2 in ARF-null cells was observed, implying that not all p53-responsive genes are equally affected by ARF loss. In contrast, other signals that induce p53, such as DNA damage by radiation, are effective in the complete absence of ARF [Kamijo et al., Cell, 91:651–659 (1997)]. Therefore, MYC signals to p53 at least in part through an ARF-dependent pathway, which is distinct from that triggered by DNA damage.

ARF and MYC-induced apoptosis: Because enforced expression of ARF itself arrests wild-type MEFs but does not kill them [Quelle et al., Cell, 83:993–1000 (1995)], a function of MYC other than ARF induction is required to trigger apoptosis. Nonetheless, the loss of either ARF or p53 confers significant resistance to MYC-induced cell death, and these effects of ARF, like its ability to induce cell cycle arrest, are p53-dependent. In cultures of wild-type MEFs acutely infected with MYC retrovirus, a significant proportion of the cells underwent apoptosis even when grown in the presence of serum. In the face of MYC overexpression, there was a strong selective advantage for cells that sustained p53 mutations, and once such variants emerged, these soon predominated and were able to continuously proliferate in chemically defined medium lacking serum. Results using MYC-infected MEFs containing a single functional ARF allele demonstrated that ARF loss, rather than p53 mutation, could also lead to establishment, in agreement with previous observations made with cells that had undergone spontaneous immortalization [Kamijo et al., Cell, 91:641–659 (1997)]. As in the latter cases, loss of ARF or p53 function appeared to be mutually exclusive events, indicating that ARF loss can relieve MYC-induced selective pressure for p53 mutation.

A conceptual dilemma is posed by observations that ARF-null cells infected with MYC virus were initially sensitive to apoptosis when shifted into serum-free medium, although significantly less so than wild-type MEFs. After several days in serum-free medium, apoptosis was no longer detected, and the MYC virus-infected, ARF-null cells again grew rapidly. This raised the possibility that MYC overexpression selected for additional cryptic genetic changes that rendered the cells resistant to apoptosis. However, when cells that had resumed proliferation in serum-free medium were infected with an ARF virus, they promptly died, implying that attenuation of apoptosis was a direct consequence of ARF loss. The high levels of MYC expression achieved acutely after virus infection were able to kill cells through an ARF-independent pathway, likely involving p53 directly. MYC levels fell as infected MEFs were propagated, and because both ARF-null and p53-null cells tolerate higher levels of MYC than wild-type cells, they appear to become resistant to apoptosis without further selection.

ARF function in tumor surveillance: Other immortalizing oncogenes, such as adenovirus E1A, can act like MYC in triggering apoptosis in an ARF-dependent manner. Among its many effects, E1A releases E2Fs 1, 2, and 3 from Rb constraint; E2F-1 can selectively induce ARF gene [DeGregori et al., Proc. Natl. Acad. Sci. USA, 94:7245–7250 (1997)] and protein expression, and trigger apoptosis in a p53-dependent manner [Wu and Levine, Proc. Natl. Acad. Sci. USA, 91:3602–3606 (1994); Qin et al., Proc. Natl. Acad. Sci. USA, 91:10918–19022 (1994); Shan and Lee, Mol. Cell. Biol., 14:8166–8173 (1994); Kowalik et al., J. Virol., 69:2491–2500 (1995)]. In agreement with these findings, MEFs lacking Rb exhibited relatively high levels of $p19^{ARF}$ expression, and E1A mutants that are unable to interact with Rb were handicapped in their ability to induce $p19^{ARF}$. Because Rb-null MEFs undergo replicative senescence in culture, high $p19^{ARF}$ levels should sensitize them to apoptosis as long as p53 function is intact. Similarly, in an in vivo mouse model using the developing murine lens, Rb-deficiency triggers apoptosis in a largely p53-dependent manner [Morgenbesser et al., Nature, 371:72–74 (1994)]. Lenses from animals lacking exon-2 of the INK4a gene, and hence likely disrupted for both INK4a and ARF function, exhibited less apoptosis than wild-type lenses but more than that observed in a p53-null background [Pomerantz et al., *Cell*, 92:713–723 (1998)].

Unlike ARF, p53 also integrates signals emanating from DNA-damage response pathways. Cancer cells are generally considered to have conserved normal p53 function if they retain wild-type p53 and exhibit an intact p53-dependent DNA damage checkpoint response. However, if such cells lack ARF, they are still compromised in their p53 response, because they would fail to respond to hyperproliferative signals induced by oncogenes such as MYC. The fact that hyperproliferative signals and DNA damage pathways can collaborate to induce p53 suggests that cells sustaining oncogenic stimulation would initially be more susceptible than their normal counterparts to chemotherapeutic drugs and to radiotherapeutic regimens that induce DNA damage. Loss of ARF would disable this synergy, making tumor cells more resistant to treatment and ultimately selecting for p53 loss in the face of higher dose therapy. ARF function may have evolved to harness the apoptotic machinery precisely for the purpose of preventing abnormal cell growth in response to oncogenic signals. This would explain why its loss is such a common event in many different forms of cancer.

What is claimed is:

1. A method at inducing cell cycle arrest in a eukaryotic cell comprising administering to said cell an ARF-p19 polypeptide, wherein said ARF-p19 polypeptide (a) has an amino acid sequence that is comprised of at least about 20% arginine residues;

(b) induces cell cycle arrest when overexpressed in eukaryotic cells; and (c) is encoded by a first reading frame that asyntactically overlaps a second reading frame, wherein said second reading frame encodes a polypeptide that inhibits one or more D-type cyclin-dependent kinases.

2. The method of claim 1, wherein said ARF-p19 polypeptide is the murine ARF-p19 polypeptide having the amino acid sequence of SEQ ID NO:2.

3. The method of claim 1, wherein said ARF-p19 polypeptide is the human ARF-p19 polypeptide having the amino acid sequence of SEQ ID NO: 4.

4. A method of inducing cell cycle arrest in a eukaryotic cell comprising administering to said cell an expression vector construct comprising a nucleic acid sequence encoding an ARF-p19 polypeptide, wherein said ARF-p19 polypeptide (a) has an amino acid sequence that is composed of at least about 20% arginine residues;

(b) induces cell cycle arrest when overexpressed in eukaryotic cells; and (c) is encoded by a first reading frame that asyntactically overlaps a second reading frame, wherein said second reading frame encodes a polypeptide that inhibits one or more D-types cyclin-dependent kinase.

5. The method of claim 4, wherein said nucleic acid has the nucleotide sequence of SEQ ID NO:1 and encodes murine ARF-p19 polypeptide.

6. The method of claim 4, wherein said nucleic acid which has the nucleotide sequence of SEQ ID NO:3 and encodes the human ARF-p19 polypeptide.

7. A method of preventing abnormal cell growth in a cell, wherein said method comprises administering an effective amount of am ARF-p19 polypeptide or an active fragment of an ARF-p19 polypeptide, wherein said ARF-p19 polypeptide (a) has an amino acid sequence that is composed of at least about 20% arginine residues;

(b) induces cell cycle arrest when overexpressed in eukaryotic cells; and (c) is encoded by a first reading frame that asyntactically overlaps a second reading frame, wherein said second reading frame encodes a polypeptide that inhibits one or more D-type cyclin-dependent kinases, and wherein said active fragment of ARF-p19 polypeptide has the ability to act as a tumor suppressor.

8. The method of claim 7, wherein said ARF-p19 polypeptide is the murine ARF-p19 polypeptide having the amino acid sequence of SEQ ID No:2.

9. The method of claim 7, wherein said ARF-p19 polypeptide is the human ARF-p19 polypeptide having the amino acid sequence of SEQ ID No:4.

10. The method of claim 7, wherein said active fragment of ARF-p19 polypeptide comprises between 10 and 62 contiguous amino acid residues of the amino acid residues 1 to 64 of the murine ARF-p19 polypeptide having the amino acid sequence of SEQ ID NO:2.

11. The method of claim 7, wherein said active fragment of ARF-p19 polypeptide comprises between 10 and 62 contiguous amino acid residues of the amino acid residues 1 to 65 of the human ARF-p19 polypeptide having the amino acid sequence of SEQ ID NO:4.

12. The method of claim 7, wherein said cell is:

(a) responding to a hyperproliferative signal; and (b) contains p53.

13. A method of preventing abnormal cell growth in a cell, wherein said method comprises administering to said cell an expression vector construct comprising a nucleic acid sequence encoding an ARF-p19 polypeptide or an active fragment of ARF-p19 polypeptide, wherein said ARF-p19 polypeptide (a) has an amino acid sequence that is composed of at least about 20% arginine residues;

(b) induces cell cycle arrest when overexpressed in eukaryotic cells; and (c) is encoded by a first reading frame that asyntactically overlaps a second reading frame, wherein said second reading frame encodes a polypeptide that inhibits one or more D-type cyclin-dependent kinases, and wherein said active fragment of ARF-p19 polypeptide has the ability to act as a tumor suppressor, and wherein said ARF-p19 polypeptide or said active fragment of ARF-p19 polypeptide is expressed.

14. The method of claim 13, wherein said nucleic acid has the nucleotide sequence of SEQ ID NO:1 and encodes murine ARF-p19 polypeptide.

15. The method of claim 13, wherein said nucleic acid has the nucleotide sequence of SEQ ID NO:3 and encodes the human ARF-p19 polypeptide.

16. The method of claim 13, wherein said active fragment of ARF-p19 polypeptide comprises between 10 and 62 contiguous amino acid residues of the amino acid residues 1 to 64 of the murine ARF-p19 polypeptide having the amino acid sequence of SEQ ID NO:2.

17. The method of claim 13, wherein said active fragment of ARF-19 polypeptide comprises between 10 and 62 contiguous amino acid residues of the amino acid residues 1 to 65 of the human ARF-p19 polypeptide having the amino acid sequence of SEQ ID NO:4.

18. The method of claim 13, wherein said cell is:

(a) responding to a hyperproliferative signal; and (b) contains p53.

* * * * *

UNITED STATES PATENT AND TRADEMARK OFFICE
CERTIFICATE OF CORRECTION

PATENT NO. : 6,586,203 B1
DATED : July 1, 2003
INVENTOR(S) : Sherr et al.

It is certified that error appears in the above-identified patent and that said Letters Patent is hereby corrected as shown below:

Column 1,
Line 3, "DCK" should read -- CDK --.

Column 92,
Line 64, "comprised" should read -- composed --.

Column 93,
Line 23, "kinase" should read -- kinases --;
Line 32, "am" should read -- an --.

Column 94,
Line 45, "ARF-19" should read -- ARF-p19 --.

Signed and Sealed this

Twenty-eighth Day of October, 2003

JAMES E. ROGAN
*Director of the United States Patent and Trademark Office*

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
        (A) LENGTH: 713 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 43..548

(ix) FEATURE:
        (A) NAME/KEY: CDS
        (B) LOCATION: 43..551

(xi) SEQUENCE DESCRIPTION: SEQ ID NO: 1:

```
GTCACAGTGA GGCCGCCGCT GAGGGAGTAC AGCAGCGGGA GC ATG GGT CGC AGG        54
                                              Met Gly Arg Arg
                                               1

TTC TTG GTG ACT GTG AGG ATT CAG CGC GCG GGC CGC CCA CTC CAA GAG      102
Phe Leu Val Thr Val Arg Ile Gln Arg Ala Gly Arg Pro Leu Gln Glu
 5                  10                  15                  20

AGG GTT TTC TTG GTG AAG TTC GTG CGA TCC CGG AGA CCC AGG ACA GCG      150
Arg Val Phe Leu Val Lys Phe Val Arg Ser Arg Arg Pro Arg Thr Ala
                    25                  30                  35

AGC TGC GCT CTG GCT TTC GTG AAC ATG TTG TTG AGG CTA GAG AGG ATC      198
Ser Cys Ala Leu Ala Phe Val Asn Met Leu Leu Arg Leu Glu Arg Ile
                40                  45                  50

TTG AGA AGA GGG CCG CAC CGG AAT CCT GGA CCA GGT GAT GAT GAT GGG      246
Leu Arg Arg Gly Pro His Arg Asn Pro Gly Pro Gly Asp Asp Asp Gly
            55                  60                  65

CAA CGT TCA CGT AGC AGC TCT TCT GCT CAA CTA CGG TGC AGA TTC GAA      294
Gln Arg Ser Arg Ser Ser Ser Ser Ala Gln Leu Arg Cys Arg Phe Glu
    70                  75                  80

CTG CGA GGA CCC CAC TAC CTT CTC CCG CCC GGT GCA CGA CGC AGC GCG      342
Leu Arg Gly Pro His Tyr Leu Leu Pro Pro Gly Ala Arg Arg Ser Ala
85                  90                  95                 100

GGA AGG CTT CCT GGA CAC GCT GGT GGT GCT GCA CGG GTC AGG GGC TCG      390
Gly Arg Leu Pro Gly His Ala Gly Gly Ala Ala Arg Val Arg Gly Ser
                105                 110                 115

GCT GGA TGT GCG CGA TGC CTG GGG TCG CCT GCC GCT CGA CTT GGC CCA      438
Ala Gly Cys Ala Arg Cys Leu Gly Ser Pro Ala Ala Arg Leu Gly Pro
            120                 125                 130
```

```
AGA GCG GGG ACA TCA AGA CAT CGT GCG ATA TTT GCG TTC CGC TGG GTG      486
Arg Ala Gly Thr Ser Arg His Arg Ala Ile Phe Ala Phe Arg Trp Val
            135                 140                 145

CTC TTT GTG TTC CGC TGG GTG GTC TTT GTG TAC CGC TGG GAA CGT CGC      534
Leu Phe Val Phe Arg Trp Val Val Phe Val Tyr Arg Trp Glu Arg Arg
150                 155                 160

CCA GAC CGA CGG GCA TAG CTTCAGCTC AAGCACGCCC AGGGCCCTGG              581
Pro Asp Arg Arg Ala *
165

AACTTCGCGG CCAATCCCAA GAGCAGAGCT AAATCCGGCC TCAGCCCGCC TTTTTCTTCT    641

TAGCTTCACT TCTAGCGATG CTAGCGTGTC TAGCATGTGG CTTTAAAAAA TACATAATAA    701

TGCTTTTTTT TT                                                        713

(2) INFORMATION FOR SEQ ID NO: 2:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Arg Arg Phe Leu Val Thr Val Arg Ile Gln Arg Ala Gly Arg
1               5                   10                  15

Pro Leu Gln Glu Arg Val Phe Leu Val Lys Phe Val Arg Ser Arg Arg
                20                  25                  30

Pro Arg Thr Ala Ser Cys Ala Leu Ala Phe Val Asn Met Leu Leu Arg
            35                  40                  45

Leu Glu Arg Ile Leu Arg Arg Gly Pro His Arg Asn Pro Gly Pro Gly
        50                  55                  60

Asp Asp Asp Gly Gln Arg Ser Arg Ser Ser Ser Ala Gln Leu Arg
65                  70                  75                  80

Cys Arg Phe Glu Leu Arg Gly Pro His Tyr Leu Leu Pro Pro Gly Asp
                85                  90                  95

Arg Arg Ser Ala Gly Arg Leu Pro Gly His Ala Gly Ala Ala Arg
                100                 105                 110

Val Arg Gly Ser Ala Gly Cys Ala Arg Cys Leu Gly Ser Pro Ala Ala
            115                 120                 125

Arg Leu Gly Pro Arg Ala Gly Thr Ser Arg His Arg Ala Ile Phe Ala
        130                 135                 140

Phe Arg Trp Val Leu Phe Val Phe Arg Trp Val Val Phe Val Tyr Arg
145                 150                 155                 160

Trp Glu Arg Arg Pro Asp Arg Arg Ala
                165

(2) INFORMATION FOR SEQ ID NO: 3:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 142..540
```

(xi) SEQUENCE DESCRIPTION: SEQ ID NO: 3:

```
CGCGCCTGCG GGGCGGAGAT GGGCAGGGGG CGGTGCGTGG GTCCCAGTCT GCAGTTAAGG        60

GGGCAGGAGT GGCGCTGCTC ACCTCTGGTG CCAAAGGGCG GCGCAGCGGC TGCCGAGCTC       120

GGCCCTGGAG GCGGCGAGAA C ATG GTG CGC AGG TTC TTG GTG ACC CTC CGG        171
                        Met Val Arg Arg Phe Leu Val Thr Leu Arg
                         1               5                  10

ATT CGG CGC GCG TGC GGC CCG CCG CGA GTG AGG GTT TTC GTG GTT CAC        219
Ile Arg Arg Ala Cys Gly Pro Pro Arg Val Arg Val Phe Val Val His
             15                  20                  25

ATC CCG CGG CTC ACG GGG GAG TGG GCA GCG CCA GGG GCG CCC GCC GCT        267
Ile Pro Arg Leu Thr Gly Glu Trp Ala Ala Pro Gly Ala Pro Ala Ala
             30                  35                  40

GTG GCC CTC GTG CTG ATG CTA CTG AGG AGC CAG CGT CTA GGG CAG CAG        315
Val Ala Leu Val Leu Met Leu Leu Arg Ser Gln Arg Leu Gly Gln Gln
             45                  50                  55

CCG CTT CCT AGA AGA CCA GGT CAT GAT GAT GGG CAG CGC CCG AGT GGC        363
Pro Leu Pro Arg Arg Pro Gly His Asp Asp Gly Gln Arg Pro Ser Gly
 60                  65                  70

GGA GCT GCT GCT GCT CCA CGG CGC GGA GCC CAA CTG CGC CGA CCC CGC        411
Gly Ala Ala Ala Ala Pro Arg Arg Gly Ala Gln Leu Arg Arg Pro Arg
 75                  80                  85                  90

CAC TCT CAC CCG ACC CGT GCA CGA CGC TGC CCG GGA GGG CTT CCT GGA        459
His Ser His Pro Thr Arg Ala Arg Arg Cys Pro Gly Gly Leu Pro Gly
                 95                 100                 105

CAC GCT GGT GGT GCT GCA CCG GGC CGG GGC GCG GCT GGA CGT GCG CGA        507
His Ala Gly Gly Ala Ala Pro Gly Arg Gly Ala Ala Gly Arg Ala Arg
                110                 115                 120

TGC CTG GGG CCG TCT GCC CGT GGA CCT GGC TGA                            540
Cys Leu Gly Pro Ser Ala Arg Gly Pro Gly *
            125                 130
```

(2) INFORMATION FOR SEQ ID NO: 4:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Val Arg Arg Phe Leu Val Thr Leu Arg Ile Arg Arg Ala Cys Gly
 1               5                  10                  15

Pro Pro Arg Val Arg Val Phe Val Val His Ile Pro Arg Leu Thr Gly
             20                  25                  30

Glu Trp Ala Ala Pro Gly Ala Pro Ala Ala Val Ala Leu Val Leu Met
             35                  40                  45

Leu Leu Arg Ser Gln Arg Leu Gly Gln Gln Pro Leu Pro Arg Arg Pro
 50                  55                  60

Gly His Asp Asp Gly Gln Arg Pro Ser Gly Gly Ala Ala Ala Ala Pro
 65                  70                  75                  80

Arg Arg Gly Ala Gln Leu Arg Arg Pro Arg His Ser His Pro Thr Arg
                 85                  90                  95

Ala Arg Arg Cys Pro Gly Gly Leu Pro Gly His Ala Gly Gly Ala Ala
                100                 105                 110

Pro Gly Arg Gly Ala Ala Gly Arg Ala Arg Cys Leu Gly Pro Ser Ala
            115                 120                 125

Arg Gly Pro Gly
```

130

(2) INFORMATION FOR SEQ ID NO: 5:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Met Met Gly Asn Val His Val Ala Ala Leu Leu Leu Asn Tyr Gly
 1               5                  10                  15

Ala Asp Ser Asn Cys Glu Asp Pro Thr Thr Phe Ser Arg Pro Val His
            20                  25                  30

Asp Ala Ala Arg Glu Gly Phe Leu Asp Thr Leu Val Val Leu His Gly
        35                  40                  45

Ser Gly Ala Arg Leu Asp Val Arg Asp Ala Trp Gly Arg Leu Pro Leu
    50                  55                  60

Asp Leu Ala Gln Glu Arg Gly His Gln Asp Ile Val Arg Tyr Leu Arg
65                  70                  75                  80

Ser Ala Gly Cys Ser Leu Cys Ser Ala Gly Trp Ser Leu Cys Thr Ala
                85                  90                  95

Gly Asn Val Ala Gln Thr Asp Gly His Ser Phe Ser Ser Ser Thr Pro
            100                 105                 110

Arg Ala Leu Glu Leu Arg Gly Gln Ser Gln Glu Gln Ser
        115                 120                 125
```

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 6:

GCAAAGCTTG AGGCCGGATT TAGCTCTGCT C                                     31

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 7:

AGGGATCCTT GGTCACTGTG AGGATTC                                         27

(2) INFORMATION FOR SEQ ID NO: 8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear -continued (ii) MOLECULE TYPE: other nucleic acid
        (A) DESCRIPTION: /desc = "Synthetic DNA"

(xi) SEQUENCE DESCRIPTION: SEQ ID NO: 8:

CGGGATCCGC TGCAGACAGA CTGGCCAG                                          28

(2) INFORMATION FOR SEQ ID NO: 9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 9:

CGTCTAGAGC GTGTCCAGGA AGCCTTCC                                          28

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 10:

Val Phe Val Tyr Arg Trp Glu Arg Arg Pro Asp Arg Arg Ala
1               5                   10

(2) INFORMATION FOR SEQ ID NO: 11:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 11:

CGGGATCCGA ATTCAGCCAT GGGTTACCCA TACGACGTCC CAGACTACGC TACCGGTCGC       60

AGGTTCTTGG TCAC                                                         74

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 12:

GCCCGCGCGC TGAATCCTCA                                                   20